(12) United States Patent
Frey et al.

(10) Patent No.: US 8,465,478 B2
(45) Date of Patent: Jun. 18, 2013

(54) SYSTEM AND METHOD FOR PERFORMING LADAR ASSISTED PROCEDURES ON THE LENS OF AN EYE

(75) Inventors: Rudolph W. Frey, Maitland, FL (US); Gary P. Gray, Orlando, FL (US); Neil Zepkin, Oveideo, FL (US)

(73) Assignee: LensAR, Inc., Orlando, FL (US)

( * ) Notice: Subject to any disclaimer, the term of this patent is extended or adjusted under 35 U.S.C. 154(b) by 170 days.

(21) Appl. No.: 12/843,685

(22) Filed: Jul. 26, 2010

(65) Prior Publication Data

US 2011/0022036 A1    Jan. 27, 2011

Related U.S. Application Data

(60) Provisional application No. 61/228,506, filed on Jul. 24, 2009.

(51) Int. Cl.
*A61B 18/20* (2006.01)

(52) U.S. Cl.
USPC ............................... 606/4; 606/105; 606/10

(58) Field of Classification Search
USPC ................. 219/121.6, 121.61, 121.62; 606/4, 606/5, 6, 10, 11, 12
See application file for complete search history.

(56) References Cited

U.S. PATENT DOCUMENTS

| | | |
|---|---|---|
| 3,074,407 A | 1/1963 | Moon et al. |
| 3,971,382 A | 7/1976 | Krasnov |
| 3,982,541 A | 9/1976 | L'Esperance, Jr. |
| 4,024,852 A | 5/1977 | L'Esperance et al. |
| 4,263,893 A | 4/1981 | Pavlak et al. |
| 4,309,998 A | 1/1982 | Aron nee Rosa et al. |
| 4,334,736 A | 6/1982 | Herbert |
| 4,381,007 A | 4/1983 | Doss |
| 4,394,144 A | 7/1983 | Aoki |
| 4,461,294 A | 7/1984 | Baron |
| 4,477,159 A | 10/1984 | Mizuno et al. |
| 4,502,816 A | 3/1985 | Creter, Jr. et al. |
| 4,517,980 A | 5/1985 | Tagnon |

(Continued)

FOREIGN PATENT DOCUMENTS

| | | |
|---|---|---|
| CA | 2553963 A1 | 8/2005 |
| CA | 2680072 A1 | 9/2008 |

(Continued)

OTHER PUBLICATIONS

Written Opinion of the International Searching Authority, PCT/ISA/237, prepared for International Application PCT/US10/43255 (Sep. 16, 2010).*

(Continued)

*Primary Examiner* — David N Spector
(74) *Attorney, Agent, or Firm* — Brinks Hofer Gilson & Lione

(57) ABSTRACT

There is provided a system, apparatus and methods for developing laser systems that can create a precise predetermined jigsaw capsulotomy. The systems, apparatus and methods further provide laser systems that can use a single laser as a therapeutic laser and as laser radar and that reduce the patient-to-patient variability and doctor-to-doctor variability associated with hand held apparatus for performing capsulorhexis and capsulotomies. There is further provided a precise predetermined jigsaw shot pattern and shaped capsulotomy that is based at least in part on the shape of an IOL and in particular an accommodating IOL.

25 Claims, 16 Drawing Sheets

U.S. PATENT DOCUMENTS

| | | |
|---|---|---|
| 4,537,193 A | 8/1985 | Tanner |
| 4,538,608 A | 9/1985 | L'Esperance, Jr. |
| 4,554,917 A | 11/1985 | Tagnon |
| 4,561,436 A | 12/1985 | Munnerlyn |
| 4,565,197 A | 1/1986 | Daly |
| 4,573,778 A | 3/1986 | Shapiro |
| 4,576,160 A | 3/1986 | Tanaka |
| 4,579,430 A | 4/1986 | Bille |
| 4,580,559 A | 4/1986 | L'Esperance |
| 4,582,405 A | 4/1986 | Muller et al. |
| 4,583,539 A | 4/1986 | Karlin et al. |
| 4,588,505 A | 5/1986 | Walley et al. |
| 4,601,037 A | 7/1986 | McDonald |
| 4,601,288 A | 7/1986 | Myers |
| 4,607,622 A | 8/1986 | Fritch et al. |
| 4,628,416 A | 12/1986 | Dewey |
| 4,633,866 A | 1/1987 | Peyman et al. |
| 4,638,801 A | 1/1987 | Daly et al. |
| 4,644,948 A | 2/1987 | Lang et al. |
| 4,648,400 A | 3/1987 | Schneider et al. |
| 4,657,013 A | 4/1987 | Hoerenz et al. |
| 4,665,913 A | 5/1987 | L'Esperance, Jr. |
| 4,669,466 A | 6/1987 | L'Esperance, Jr. |
| 4,669,839 A | 6/1987 | Muchel |
| 4,682,595 A | 7/1987 | Hoerenz et al. |
| 4,686,979 A | 8/1987 | Gruen et al. |
| 4,686,992 A | 8/1987 | Dewey et al. |
| 4,702,245 A | 10/1987 | Schroder et al. |
| 4,702,576 A | 10/1987 | Magnante |
| 4,711,540 A | 12/1987 | Yoshino et al. |
| 4,711,541 A | 12/1987 | Yoshino et al. |
| 4,712,543 A | 12/1987 | Baron |
| 4,715,703 A | 12/1987 | Cornsweet et al. |
| 4,718,418 A | 1/1988 | L'Esperance, Jr. |
| 4,719,912 A | 1/1988 | Weinberg |
| 4,721,379 A | 1/1988 | L'Esperance |
| 4,724,522 A | 2/1988 | Belgorod |
| 4,729,372 A | 3/1988 | L'Esperance, Jr. |
| 4,729,373 A | 3/1988 | Peyman |
| 4,732,148 A | 3/1988 | L'Esperance, Jr. |
| 4,732,460 A | 3/1988 | Kele et al. |
| 4,736,744 A | 4/1988 | Koike et al. |
| 4,741,612 A | 5/1988 | Birngruber et al. |
| 4,744,362 A | 5/1988 | Gründler |
| 4,758,081 A | 7/1988 | Barnes |
| 4,765,336 A | 8/1988 | Blaha et al. |
| 4,770,162 A | 9/1988 | L'Esperance et al. |
| 4,770,172 A | 9/1988 | L'Esperance, Jr. |
| 4,770,486 A | 9/1988 | Wang et al. |
| 4,772,116 A | 9/1988 | Schroder et al. |
| 4,773,414 A | 9/1988 | L'Esperance, Jr. |
| 4,775,361 A | 10/1988 | Jacques et al. |
| 4,776,687 A | 10/1988 | Nakanishi et al. |
| 4,798,204 A | 1/1989 | L'Esperance, Jr. |
| 4,820,264 A | 4/1989 | Matsui et al. |
| 4,830,483 A | 5/1989 | Kohayakawa et al. |
| 4,832,043 A | 5/1989 | Ichihashi |
| 4,837,857 A | 6/1989 | Scheller et al. |
| 4,838,266 A | 6/1989 | Koziol et al. |
| 4,840,175 A | 6/1989 | Peyman |
| 4,846,172 A | 7/1989 | Berlin |
| 4,848,340 A | 7/1989 | Bille et al. |
| 4,854,693 A | 8/1989 | Ichihashi et al. |
| 4,856,513 A | 8/1989 | Muller |
| 4,862,888 A | 9/1989 | Yessik |
| 4,863,261 A | 9/1989 | Flammer |
| 4,865,029 A | 9/1989 | Pankratov |
| 4,865,441 A | 9/1989 | Reis |
| 4,866,243 A | 9/1989 | Sakane et al. |
| 4,870,952 A | 10/1989 | Martinez |
| 4,881,808 A | 11/1989 | Bille et al. |
| 4,883,351 A | 11/1989 | Weiss |
| 4,884,884 A | 12/1989 | Reis |
| 4,887,019 A | 12/1989 | Reis et al. |
| 4,887,592 A | 12/1989 | Loertscher |
| 4,891,043 A | 1/1990 | Zeimer et al. |
| 4,900,143 A | 2/1990 | Bessler et al. |
| 4,900,145 A | 2/1990 | Akiyama |
| 4,901,718 A | 2/1990 | Bille et al. |
| 4,902,124 A | 2/1990 | Roy, Sr. et al. |
| 4,903,695 A | 2/1990 | Warner et al. |
| 4,905,711 A | 3/1990 | Bennett et al. |
| 4,907,586 A | 3/1990 | Bille et al. |
| 4,911,160 A | 3/1990 | Thyzel |
| 4,911,711 A | 3/1990 | Telfair et al. |
| 4,917,486 A | 4/1990 | Raven et al. |
| 4,931,053 A | 6/1990 | L'Esperance, Jr. |
| 4,941,093 A | 7/1990 | Marshall et al. |
| 4,951,663 A | 8/1990 | L'Esperance, Jr. |
| 4,953,969 A | 9/1990 | Fedorov |
| 4,966,577 A | 10/1990 | Crosson et al. |
| 4,972,836 A | 11/1990 | Schenck et al. |
| 4,973,330 A | 11/1990 | Azema et al. |
| 4,976,709 A | 12/1990 | Sand |
| 4,988,348 A | 1/1991 | Bille |
| 4,994,058 A | 2/1991 | Raven et al. |
| 5,000,561 A | 3/1991 | Lawniczak et al. |
| 5,000,751 A | 3/1991 | Schroder et al. |
| 5,002,571 A | 3/1991 | O'Donnell, Jr. et al. |
| 5,013,311 A | 5/1991 | Nouri |
| 5,019,074 A | 5/1991 | Muller |
| 5,041,134 A | 8/1991 | O'Donnell |
| 5,048,946 A | 9/1991 | Sklar et al. |
| 5,049,147 A | 9/1991 | Danon |
| 5,054,907 A | 10/1991 | Sklar et al. |
| 5,057,102 A | 10/1991 | Tomioka et al. |
| 5,067,951 A | 11/1991 | Greve |
| 5,090,798 A | 2/1992 | Kohayakawa |
| 5,092,863 A | 3/1992 | Schanzlin |
| 5,094,521 A | 3/1992 | Jolson et al. |
| 5,098,426 A | 3/1992 | Sklar et al. |
| 5,102,409 A | 4/1992 | Balgorod |
| 5,108,388 A | 4/1992 | Trokel |
| 5,108,412 A | 4/1992 | Krumeich et al. |
| 5,112,328 A | 5/1992 | Taboada et al. |
| 5,116,114 A | 5/1992 | Nakamura et al. |
| 5,122,135 A | 6/1992 | Durr et al. |
| 5,123,902 A | 6/1992 | Muller et al. |
| 5,128,509 A | 7/1992 | Black et al. |
| 5,133,708 A | 7/1992 | Smith |
| 5,137,530 A | 8/1992 | Sand |
| 5,141,506 A | 8/1992 | York |
| 5,147,349 A | 9/1992 | Johnson et al. |
| 5,147,352 A | 9/1992 | Azema et al. |
| 5,152,055 A | 10/1992 | L'Esperance, III et al. |
| 5,152,759 A | 10/1992 | Parel et al. |
| 5,163,934 A | 11/1992 | Munnerlyn |
| 5,171,242 A | 12/1992 | Dewey et al. |
| 5,174,021 A | 12/1992 | L'Esperance, III et al. |
| 5,178,635 A | 1/1993 | Gwon et al. |
| 5,188,631 A | 2/1993 | L'Esperance, Jr. |
| 5,194,948 A | 3/1993 | L'Esperance, III et al. |
| 5,196,006 A | 3/1993 | Klopotek et al. |
| 5,196,027 A | 3/1993 | Thompson et al. |
| 5,201,730 A | 4/1993 | Easley et al. |
| 5,202,708 A | 4/1993 | Sasaki et al. |
| 5,203,353 A | 4/1993 | Easley et al. |
| 5,207,668 A | 5/1993 | L'Esperance, Jr. |
| 5,213,092 A | 5/1993 | Uram |
| 5,215,104 A | 6/1993 | Steinert |
| 5,217,459 A | 6/1993 | Kamerling |
| 5,219,343 A | 6/1993 | L'Esperance, Jr. |
| 5,219,344 A | 6/1993 | Yoder, Jr. |
| 5,222,981 A | 6/1993 | Werblin |
| 5,224,942 A | 7/1993 | Beuchat et al. |
| 5,226,903 A | 7/1993 | Mizuno |
| 5,246,435 A | 9/1993 | Billie et al. |
| 5,246,436 A | 9/1993 | Rowe |
| 5,257,988 A | 11/1993 | L'Esperance, Jr. |
| 5,258,025 A | 11/1993 | Fedorov et al. |
| 5,263,950 A | 11/1993 | L'Esperance, Jr. |
| 5,263,951 A | 11/1993 | Spears et al. |
| 5,275,593 A | 1/1994 | Easley et al. |
| 5,277,911 A | 1/1994 | Viegas et al. |
| 5,279,298 A | 1/1994 | Flower |
| 5,279,611 A | 1/1994 | McDonnell et al. |
| 5,281,211 A | 1/1994 | Parel et al. |

| | | | | | | |
|---|---|---|---|---|---|---|
| 5,282,798 | A | 2/1994 | Bruse et al. | 5,527,774 A | 6/1996 | Girard |
| 5,284,477 | A | 2/1994 | Hanna et al. | 5,529,076 A | 6/1996 | Schachar |
| 5,288,293 | A | 2/1994 | O'Donnell, Jr. | 5,533,997 A | 7/1996 | Ruiz |
| 5,290,272 | A | 3/1994 | Burstein et al. | 5,548,352 A | 8/1996 | Dewey |
| 5,295,989 | A | 3/1994 | Nakamura | 5,549,597 A | 8/1996 | Shimmick et al. |
| 5,300,020 | A | 4/1994 | L'Esperance, Jr. | 5,556,395 A | 9/1996 | Shimmick et al. |
| 5,300,061 | A | 4/1994 | Easley et al. | 5,573,544 A | 11/1996 | Simon et al. |
| 5,300,062 | A | 4/1994 | Ueno | 5,594,753 A | 1/1997 | Frey et al. |
| 5,300,063 | A | 4/1994 | Tano et al. | 5,607,472 A | 3/1997 | Thompson |
| 5,300,114 | A | 4/1994 | Gwon et al. | 5,616,139 A | 4/1997 | Okamoto |
| 5,304,168 | A | 4/1994 | Sun | 5,618,284 A | 4/1997 | Sand |
| 5,304,169 | A | 4/1994 | Sand | 5,620,435 A | 4/1997 | Belkin et al. |
| 5,311,224 | A | 5/1994 | Enomoto | 5,627,162 A | 5/1997 | Gwon et al. |
| 5,312,320 | A | 5/1994 | L'Esperance, Jr. | 5,632,742 A | 5/1997 | Frey et al. |
| 5,312,393 | A | 5/1994 | Mastel | 5,651,782 A | 7/1997 | Simon et al. |
| 5,314,422 | A | 5/1994 | Nizzola | 5,656,186 A | 8/1997 | Mourou et al. |
| 5,318,047 | A | 6/1994 | Davenport et al. | 5,684,560 A | 11/1997 | Roffman et al. |
| 5,318,560 | A | 6/1994 | Blount et al. | 5,699,142 A | 12/1997 | Lee et al. |
| 5,323,788 | A | 6/1994 | Silvestrini et al. | 5,709,868 A | 1/1998 | Perricone |
| 5,324,281 | A | 6/1994 | Muller | 5,722,952 A | 3/1998 | Schachar |
| 5,325,134 | A | 6/1994 | Kohayakawa | 5,722,970 A | 3/1998 | Colvard et al. |
| 5,334,190 | A | 8/1994 | Seiler | 5,731,909 A | 3/1998 | Schachar |
| 5,336,215 | A | 8/1994 | Hsueh et al. | 5,738,677 A | 4/1998 | Colvard et al. |
| 5,336,216 | A | 8/1994 | Dewey | 5,752,950 A | 5/1998 | Frey et al. |
| 5,342,351 | A | 8/1994 | Blaha et al. | 5,773,472 A | 6/1998 | Stjernschantz et al. |
| 5,342,370 | A | 8/1994 | Simon et al. | 5,828,686 A | 10/1998 | Frey et al. |
| 5,345,948 | A | 9/1994 | O'Donnell, Jr. | 5,843,184 A | 12/1998 | Cionni |
| 5,346,491 | A | 9/1994 | Oertli | 5,849,006 A | 12/1998 | Frey et al. |
| 5,347,329 | A | 9/1994 | Ota | 5,886,768 A | 3/1999 | Knopp et al. |
| 5,348,551 | A | 9/1994 | Spears et al. | 5,907,908 A | 6/1999 | Cunanan et al. |
| 5,350,374 | A | 9/1994 | Smith | 5,912,915 A | 6/1999 | Reed et al. |
| 5,354,331 | A | 10/1994 | Schachar | 5,919,186 A | 7/1999 | Bath |
| 5,355,181 | A | 10/1994 | Ashizaki et al. | 5,980,513 A | 11/1999 | Frey et al. |
| 5,356,407 | A | 10/1994 | Easley et al. | 5,984,916 A | 11/1999 | Lai |
| 5,356,409 | A | 10/1994 | Nizzola | 5,993,441 A | 11/1999 | Muller et al. |
| 5,360,424 | A | 11/1994 | Klopotek | 6,007,578 A | 12/1999 | Schachar |
| 5,364,388 | A | 11/1994 | Koziol | 6,013,101 A | 1/2000 | Israel |
| 5,364,390 | A | 11/1994 | Taboada et al. | 6,019,472 A | 2/2000 | Koester et al. |
| 5,368,590 | A | 11/1994 | Itoh | 6,022,088 A | 2/2000 | Metzler |
| 5,370,641 | A | 12/1994 | O'Donnell, Jr. | 6,027,494 A | 2/2000 | Frey |
| 5,372,595 | A | 12/1994 | Gaasterland et al. | 6,050,687 A | 4/2000 | Billie et al. |
| 5,374,265 | A | 12/1994 | Sand | 6,055,259 A | 4/2000 | Frey et al. |
| 5,376,086 | A | 12/1994 | Khoobehi et al. | 6,059,772 A | 5/2000 | Hsia et al. |
| 5,391,165 | A | 2/1995 | Fountain et al. | 6,070,981 A | 6/2000 | Mihashi et al. |
| 5,395,356 | A | 3/1995 | King et al. | 6,099,522 A | 8/2000 | Knopp et al. |
| 5,403,307 | A | 4/1995 | Zelman | 6,114,651 A | 9/2000 | Schluter et al. |
| 5,408,484 | A | 4/1995 | Weimel | 6,132,424 A | 10/2000 | Tang |
| 5,411,501 | A | 5/1995 | Klopotek | 6,186,148 B1 | 2/2001 | Okada |
| 5,412,561 | A | 5/1995 | Rosenshein et al. | 6,190,375 B1 | 2/2001 | Frey |
| 5,413,555 | A | 5/1995 | McMahan | 6,197,018 B1 | 3/2001 | O'Donnell |
| 5,423,798 | A | 6/1995 | Crow | 6,197,056 B1 | 3/2001 | Schachar |
| 5,423,800 | A | 6/1995 | Ren et al. | 6,252,595 B1 | 6/2001 | Birmingham et al. |
| 5,423,801 | A | 6/1995 | Marshall et al. | 6,254,595 B1 | 7/2001 | Juhasz et al. |
| 5,425,727 | A | 6/1995 | Koziol | 6,261,220 B1 | 7/2001 | Frey et al. |
| 5,425,729 | A | 6/1995 | Ishida et al. | 6,271,914 B1 | 8/2001 | Frey et al. |
| 5,425,730 | A | 6/1995 | Luloh | 6,271,915 B1 | 8/2001 | Frey et al. |
| 5,437,657 | A | 8/1995 | Epstein | 6,275,718 B1 | 8/2001 | Lempert |
| 5,437,658 | A | 8/1995 | Muller et al. | 6,280,435 B1 | 8/2001 | Odrich et al. |
| 5,439,462 | A | 8/1995 | Bille et al. | 6,280,468 B1 | 8/2001 | Schachar |
| 5,441,496 | A | 8/1995 | Easley et al. | 6,299,640 B1 | 10/2001 | Schachar |
| 5,441,511 | A | 8/1995 | hanna | 6,302,877 B1 | 10/2001 | Ruiz |
| 5,442,412 | A | 8/1995 | Frey et al. | 6,302,879 B1 | 10/2001 | Frey et al. |
| 5,442,487 | A | 8/1995 | Mizuno | 6,312,422 B1 | 11/2001 | Duback |
| 5,445,633 | A | 8/1995 | Nakamura et al. | 6,312,424 B1 | 11/2001 | Largent |
| 5,460,627 | A | 10/1995 | O'Donnell, Jr. | 6,313,165 B1 | 11/2001 | Grunberger et al. |
| 5,461,212 | A | 10/1995 | Seiler et al. | 6,315,773 B1 | 11/2001 | Frey et al. |
| 5,462,739 | A | 10/1995 | Dan et al. | 6,319,274 B1 | 11/2001 | Shadduck |
| 5,465,737 | A | 11/1995 | Schachar | 6,322,545 B1 | 11/2001 | Schachar |
| 5,470,329 | A | 11/1995 | Sumiya | 6,322,556 B1 | 11/2001 | Gwon et al. |
| 5,474,548 | A | 12/1995 | Knopp et al. | 6,324,191 B1 | 11/2001 | Horvath |
| 5,476,511 | A | 12/1995 | Gwon et al. | 6,325,791 B1 | 12/2001 | Shimoji |
| 5,480,396 | A | 1/1996 | Simon et al. | 6,328,732 B1 | 12/2001 | Donitzky et al. |
| 5,484,432 | A | 1/1996 | Sand | 6,344,040 B1 | 2/2002 | Juhasz et al. |
| 5,489,299 | A | 2/1996 | Schachar | 6,373,571 B1 | 4/2002 | Juhasz et al. |
| 5,503,165 | A | 4/1996 | Schachar | D459,806 S | 7/2002 | Webb |
| 5,507,740 | A | 4/1996 | O'Donnell, Jr. | D459,807 S | 7/2002 | Webb |
| 5,514,124 | A | 5/1996 | Alpins | 6,413,262 B2 | 7/2002 | Saishin et al. |
| 5,514,125 | A | 5/1996 | Lasser et al. | D462,442 S | 9/2002 | Webb |
| 5,520,679 | A | 5/1996 | Lin | D462,443 S | 9/2002 | Webb |

| | | | | | |
|---|---|---|---|---|---|
| 6,451,008 B1 | 9/2002 | Frey et al. | 2004/0156014 A1 | 8/2004 | Piers et al. |
| 6,460,997 B1 | 10/2002 | Frey et al. | 2004/0199149 A1 | 10/2004 | Myers et al. |
| 6,467,906 B1 | 10/2002 | Alpins | 2004/0199150 A1 | 10/2004 | Lai |
| 6,493,151 B2 | 12/2002 | Schachar | 2004/0243111 A1 | 12/2004 | Bendett et al. |
| 6,494,910 B1 | 12/2002 | Ganem et al. | 2004/0249403 A1 | 12/2004 | Loomas et al. |
| 6,497,483 B2 | 12/2002 | Frey et al. | 2005/0107773 A1 | 5/2005 | Bergt et al. |
| 6,530,917 B1 | 3/2003 | Seiler et al. | 2005/0107775 A1 | 5/2005 | Huang et al. |
| 6,544,254 B1 | 4/2003 | Bath | 2005/0165387 A1 | 7/2005 | Lubatschowski et al. |
| 6,547,394 B2 | 4/2003 | Doherty | 2005/0197655 A1 | 9/2005 | Telfair et al. |
| 6,554,825 B1 | 4/2003 | Murray et al. | 2005/0203492 A1 | 9/2005 | Nguyen et al. |
| 6,585,726 B2 | 7/2003 | Frey et al. | 2005/0243276 A1 | 11/2005 | Van Heugten et al. |
| 6,588,902 B2 | 7/2003 | Isogai | 2005/0270486 A1 | 12/2005 | Teiwes et al. |
| 6,610,686 B1 | 8/2003 | Enrico et al. | 2006/0058682 A1 | 3/2006 | Miller et al. |
| 6,623,476 B2 | 9/2003 | Juhasz et al. | 2006/0192921 A1 | 8/2006 | Loesel et al. |
| 6,626,445 B2 | 9/2003 | Murphy et al. | 2006/0195076 A1 | 8/2006 | Blumenkranz et al. |
| 6,626,893 B2 | 9/2003 | Frey et al. | 2006/0215111 A1 | 9/2006 | Mihashi |
| 6,626,894 B2 | 9/2003 | Frey et al. | 2006/0259022 A1 | 11/2006 | Lin |
| 6,626,895 B2 | 9/2003 | Frey et al. | 2007/0078447 A1 | 4/2007 | Weinacht et al. |
| 6,626,896 B2 | 9/2003 | Frey et al. | 2007/0084694 A1 | 4/2007 | Doherty et al. |
| 6,626,897 B2 | 9/2003 | Frey et al. | 2007/0093795 A1 | 4/2007 | Melcher et al. |
| 6,626,898 B2 | 9/2003 | Frey et al. | 2007/0093796 A1 | 4/2007 | Raksi et al. |
| 6,648,877 B1 | 11/2003 | Juhasz et al. | 2007/0129693 A1 | 6/2007 | Hunter et al. |
| 6,669,342 B2 | 12/2003 | Liebermann et al. | 2007/0173794 A1 * | 7/2007 | Frey et al. ......................... 606/5 |
| 6,676,653 B2 | 1/2004 | Juhasz et al. | 2007/0173795 A1 | 7/2007 | Frey et al. |
| 6,693,927 B1 | 2/2004 | Horvath et al. | 2007/0185475 A1 | 8/2007 | Frey et al. |
| 6,702,853 B1 * | 3/2004 | Peyman ....................... 623/6.39 | 2007/0265603 A1 | 11/2007 | Pinelli |
| 6,726,679 B1 | 4/2004 | Dick et al. | 2008/0071254 A1 | 3/2008 | Lummis et al. |
| 6,849,091 B1 | 2/2005 | Cumming | 2008/0111972 A1 | 5/2008 | Barth et al. |
| 6,863,667 B2 | 3/2005 | Webb et al. | 2008/0114386 A1 | 5/2008 | Iliakis et al. |
| 6,905,641 B2 | 6/2005 | Platt et al. | 2008/0186551 A1 | 8/2008 | Hanft et al. |
| 6,923,955 B2 | 8/2005 | Till et al. | 2008/0281303 A1 | 11/2008 | Culbertson et al. |
| 6,962,583 B2 | 11/2005 | Kadziauskas et al. | 2008/0281413 A1 | 11/2008 | Culbertson et al. |
| 7,044,568 B2 | 5/2006 | Olivera et al. | 2008/0312685 A1 | 12/2008 | Newcott et al. |
| 7,077,838 B2 | 7/2006 | Wong | 2009/0069794 A1 | 3/2009 | Kurtz |
| 7,182,759 B2 | 2/2007 | Kadziauskas et al. | 2009/0088734 A1 | 4/2009 | Mordaunt |
| 7,188,949 B2 | 3/2007 | Bandhauer et al. | 2009/0126870 A1 | 5/2009 | Zadoyan et al. |
| 7,220,255 B2 | 5/2007 | Lai | 2009/0131921 A1 | 5/2009 | Kurtz |
| 7,252,662 B2 | 8/2007 | McArdle et al. | 2009/0137988 A1 | 5/2009 | Kurtz |
| 7,264,355 B2 | 9/2007 | Rathjen | 2009/0137991 A1 | 5/2009 | Kurtz |
| RE40,002 E | 1/2008 | Lin | 2009/0137993 A1 | 5/2009 | Kurtz |
| RE40,184 E | 3/2008 | Lin | 2009/0161065 A1 | 6/2009 | Smith, III et al. |
| 7,338,167 B2 | 3/2008 | Zelvin et al. | 2009/0171327 A1 | 7/2009 | Kurtz et al. |
| 7,357,504 B2 | 4/2008 | Fischer et al. | 2009/0177189 A1 | 7/2009 | Raksi |
| 7,364,575 B2 | 4/2008 | Van Saarloos | 2009/0187178 A1 | 7/2009 | Muller et al. |
| 7,390,089 B2 | 6/2008 | Loesel et al. | 2009/0244482 A1 | 10/2009 | Elsner et al. |
| RE40,420 E | 7/2008 | Dick et al. | 2009/0281530 A1 | 11/2009 | Korn |
| 7,402,159 B2 | 7/2008 | Loesel et al. | 2010/0002837 A1 | 1/2010 | Gertner et al. |
| 7,467,871 B2 | 12/2008 | Lawhorn et al. | 2010/0004641 A1 | 1/2010 | Frey et al. |
| 7,540,613 B2 | 6/2009 | Severns | 2010/0004643 A1 | 1/2010 | Frey et al. |
| 7,655,002 B2 | 2/2010 | Myers | 2010/0022994 A1 | 1/2010 | Frey et al. |
| 7,717,908 B2 | 5/2010 | Ruiz et al. | 2010/0022995 A1 | 1/2010 | Frey et al. |
| 7,766,903 B2 | 8/2010 | Blumenkranz et al. | 2010/0022996 A1 | 1/2010 | Frey et al. |
| 7,836,894 B2 | 11/2010 | Brinkmann et al. | 2010/0042079 A1 | 2/2010 | Frey et al. |
| 7,959,289 B2 | 6/2011 | Cattin-Liebl | 2010/0060855 A1 | 3/2010 | Graether |
| 8,085,408 B2 | 12/2011 | Everett et al. | 2010/0114079 A1 | 5/2010 | Myers et al. |
| 8,262,553 B2 | 9/2012 | Weston et al. | 2010/0256614 A1 | 10/2010 | Donitzky et al. |
| 8,262,646 B2 * | 9/2012 | Frey et al. ......................... 606/4 | 2010/0256615 A1 | 10/2010 | Blumenkranz et al. |
| 2001/0029363 A1 | 10/2001 | Lin | 2010/0274228 A1 | 10/2010 | Mrochen et al. |
| 2002/0004658 A1 | 1/2002 | Munnerlyn et al. | 2010/0292676 A1 | 11/2010 | Larsen |
| 2002/0025311 A1 | 2/2002 | Till | 2010/0292678 A1 | 11/2010 | Frey et al. |
| 2002/0029053 A1 | 3/2002 | Gordon | 2010/0312231 A1 | 12/2010 | Singh |
| 2002/0049450 A1 | 4/2002 | Myers | 2010/0324542 A1 | 12/2010 | Kurtz |
| 2002/0103478 A1 | 8/2002 | Gwon et al. | 2010/0331829 A1 | 12/2010 | Bor et al. |
| 2002/0110549 A1 | 8/2002 | Till | 2011/0022035 A1 | 1/2011 | Porter et al. |
| 2002/0138139 A1 | 9/2002 | Till | 2011/0028950 A1 | 2/2011 | Raksi et al. |
| 2002/0140903 A1 | 10/2002 | Schachar | 2011/0092965 A1 | 4/2011 | Slatkine |
| 2002/0159028 A1 | 10/2002 | Masaki | 2011/0118712 A1 | 5/2011 | Lubatschowski et al. |
| 2003/0050629 A1 | 3/2003 | Kadziauskas et al. | 2011/0137301 A1 | 6/2011 | Bartoli |
| 2003/0055412 A1 | 3/2003 | Lieberman et al. | 2011/0149240 A1 | 6/2011 | Alpins |
| 2003/0076477 A1 | 4/2003 | Matsumoto | 2011/0160710 A1 | 6/2011 | Frey et al. |
| 2003/0109926 A1 | 6/2003 | Portney | 2011/0160711 A1 | 6/2011 | Naranjo-Tackman et al. |
| 2003/0135272 A1 | 7/2003 | Brady et al. | 2011/0166557 A1 | 7/2011 | Naranjo-Tackman et al. |
| 2003/0139737 A1 | 7/2003 | Lin | 2011/0184395 A1 | 7/2011 | Schuele et al. |
| 2003/0212387 A1 | 11/2003 | Kurtz et al. | 2011/0187995 A1 | 8/2011 | Frey et al. |
| 2003/0220630 A1 | 11/2003 | Lin et al. | 2011/0190739 A1 | 8/2011 | Frey et al. |
| 2004/0054359 A1 | 3/2004 | Ruiz et al. | 2011/0190740 A1 | 8/2011 | Frey et al. |
| 2004/0059321 A1 | 3/2004 | Knopp et al. | 2011/0292340 A1 | 12/2011 | Shimizu et al. |
| 2004/0070761 A1 | 4/2004 | Horvath et al. | 2012/0016350 A1 | 1/2012 | Myers et al. |
| 2004/0143244 A1 | 7/2004 | Grey et al. | 2012/0182522 A1 | 7/2012 | Frey et al. |

| | | | |
|---|---|---|---|
| 2012/0265181 A1 | 10/2012 | Frey | |
| 2012/0271286 A1 | 10/2012 | Curatu et al. | |
| 2012/0296321 A1 | 11/2012 | Frey et al. | |
| 2012/0330290 A1 | 12/2012 | Gray et al. | |

FOREIGN PATENT DOCUMENTS

| | | | |
|---|---|---|---|
| EP | 0 397 962 A1 | 11/1990 | |
| EP | 0 933 060 A1 | 8/1999 | |
| EP | 1 970 034 A1 | 9/2008 | |
| FR | 2 497 087 A1 | 7/1982 | |
| JP | 5-115437 A | 5/1993 | |
| WO | WO 91/19539 A1 | 12/1991 | |
| WO | WO 01/13838 A1 | 3/2001 | |
| WO | WO 03/002010 A1 | 1/2003 | |
| WO | WO 2005/070358 A1 | 8/2005 | |
| WO | WO 2012/051490 A1 | 4/2012 | |

OTHER PUBLICATIONS

International Search Report, PCT/ISA/210, prepared for International Application PCT/US10/43255 (Sep. 16, 2010).*

Kasthurirangan, Sanjeev et al., "Amplitude dependent accommodative dynamics in humans", *Vision Research*, vol. 43, 2003, pp. 2945-2956.

Kasthurirangan, Sanjeev, "Influence of Amplitude and Starting Point on Accommodative Dynamics in Humans", *IOVS*, vol. 46, No. 9, Sep. 2005, pp. 3463-3472.

Kaufman, Paul L., M.D., "Accommodation and Presbyopia: Neuromuscular and Biophysical Aspects", *Adler's Physiology of the Eye*, date unknown but prior to Jul. 2009, pp. 391-411.

Keeney, Arthur H., M.D., "Intralenticular Foreign Bodies", *Arch Ophthal.*, vol. 86, Nov. 1971, pp. 499-501.

König, Karsten et al., "Are Femtosecond Lasers Safe for Ophthalmic Applications?", *Fraunhofer Institute of Biomedical Technologies*, undated but prior to Jul. 2009, pp. 1-16.

König, Karsten et al., "Cornea surgery with nanojoule femtosecond laser pulses", *Proc. of SPIE*, vol. 5688, 2005, pp. 288-293.

König, Karsten et al., "First in vivo animal studies on intraocular nanosurgery and multiphoton tomography with low-energy 80 MHz near infrared femtosecond laser pulses", *Proc. of SPIE*, vol. 5314, 2004, pp. 262-269.

Koopmans, Steven a. et al., "Polymer Refilling of Presbyopic Human Lenses in Vitro Restores the Ability to Undergo Accommodative Changes", *IOVS*, vol. 44, No. 1, Jan. 2003, pp. 250-257.

Koretz, Jane F. et al., "A Model for Accommodation in the Young Human Eye: The Effects of Lens Elastic Anisotropy on The Mechanism", *Vision Res.*, vol. 23, No. 12, 1983, pp. 1679-1686.

Koretz, Jane F. et al., "Accommodation and Presbyopia in The Human Eye—Aging of the Anterior Segment", *Vision Res.*, vol. 29, No. 12, 1989, pp. 1685-1692.

Koretz, Jane F. et al., "Accommodation and Presbyopia in the Human Eye—Changes in the Anterior Segment and Crystalline Lens With Focus", *IOVS*, vol. 38, No. 3, Mar. 1997, pp. 569-578.

Koretz, Jane F. et al., "Analysis of Human Crystalline Lens Curvature as a Function of Accommodative State and Age", *Vision Res.*, vol. 24, No. 10, 1984, pp. 1141-1151.

Koretz, Jane F. et al., "How the Human Eye Focuses", *Scientific American*, Jul. 1988, pp. 92-99.

Koretz, Jane F. et al., "Model of the Accommodative Mechanism in The Human Eye", *Vis. Res.*, vol. 22, 1982, pp. 917-927.

Koretz, Jane F. et al., "Scheimpflug and high-resolution magnetic resonance imaging of the anterior segment: a comparative study", *J. Opt. Soc. Am. A*, vol. 21, No. 3, Mar. 2004, pp. 346-354.

Koretz, Jane F. et al., "The Zones of Discontinuity in the Human Lens: Development and Distribution with Age", *Vision Res.*, vol. 34, No. 22, 1994, pp. 2955-2962.

Krag, Susanne et al., "Biomechanical Characteristics of the Human Anterior Lens Capsule in Relation to Age", *Investigative Ophthalmology & Visual Science*, vol. 38, No. 2, Feb. 1997, pp. 357-362.

Krag, Susanne, "Biomechanical measurements of the lens capsule", *Scandinavian University Theses*, 1999, 3 pgs.

Krag, Susanne et al., "Mechanical Properties of the Human Posterior Lens Capsule", *IOVS*, vol. 44, No. 2, 2003, pp. 691-696.

Krauss, Joel et al., "Laser Interactions With the Cornea", *Survey of Ophthalmology* A20, vol. 31, No. 1, Jul./Aug. 1986, pp. 37-53.

Kronemyer, Bob, "Accommodating IOL? Impossible, Recent Study Seems to Say". *Ocular Surgery News*, http://www.slackmc.com, Sep. 15, 1996, 2 pgs.

Krueger, Ronald R. et al., "Experimental Increase in Accommodative Potential after Neodymium: Yttrium-Aluminum-Garnet Laser Photodisruption of Paired Cadaver Lenses", *Ophthalmology*, vol. 108, No. 11, 2001, pp. 2122-2129.

Krueger, Ronald R. et al., "First safety study of femtosecond laser photodisruption in animal lenses: Tissue morphology and cataractogenesis", *J Cataract Refract Surg*, vol. 31, Dec. 2005, pp. 2386-2394.

Krueger, Ronald R., M.D., et al., "Nonmechanical Microkeratomes Using Laser and Water Jet Technology", Publisher unknown, date unknown but prior to Jul. 2009, pp. 1-33.

Krueger, R.R., "Surf's Up—Catch a wave with a waterjet", *Jrn. Ref. Surg.*, vol. 14, No. 3, May/Jun. 1998, pp. 280-281.

Krueger, Ronald R., M.D. et al., "Ultrastructure of Picosecond Laser Intrastromal Photodisruption", *Journal of Refractive Surgery*, vol. 12, Jul./Aug. 1996, pp. 607-612.

Kuizenga, Dirk J., "FM-Laser Operation of the Nd:YAG Laser", *IEEE Journal of Quantum Electronics*, vol. 6, No. 11, 1970, pp. 673-677.

Kurapkienė, S. et al., "The relationship of ultrasonic and mechanical properties of human nuclear cataract. A pilot study", *Ultragarsas*, vol. 54, No. 1, 2005, pp. 39-43.

Kurtz, Ron et al., "Femtosecond Laser Corneal Refractive Surgery", *Proc. of SPIE*, vol. 3591, 1999, pp. 209-219.

Kurtz, Ron et al., "Ophthalmic Applications of Femtosecond Lasers", *Proc. f Spie*, vol. 3616, 1999, pp. 51-65.

Kurtz, Ron M. et al., "Optimal Laser Parameters for Intrastromal Corneal Surgery", *Proc. of SPIE*, vol. 3255, 1998, pp. 56-66.

Kurtz, Ron M., MD, et al., "Photo-disruption in the Human Cornea as a Function of Laser Pulse Width", *Journal of Refractive Surgery*, vol. 13, Nov./Dec. 1997, pp. 653-658.

Kuszak, J. R. et al., "A Quantitative Analysis of Sutural Contributions to Variability in Back Vertex Distance and Transmittance in Rabbit Lenses as a Function of Development, Growth, and Age", *Optometry and Vision Science*, vol. 79, No. 3, Mar. 2002, pp. 193-204.

Kuszak, J. R. et al., "Anatomy of Aged and Senile Cataractous Lenses", from "Biochemistry of The Crystalline Lens", undated but prior to Jul. 2009, pp. 564-575.

Kuszak, J. R. et al., "Biochemistry of the Crystalline Lens; Anatomy of Aged and Senile Cataractous Lenses", pp. 564-575.

Kuszak, J. R. et al., "Development of lens sutures", *Int. J. Dev. Biol.*, vol. 48, 2004, pp. 889-902.

Kuszak, J. R. et al., "Electron Microscope Observations of the Crystalline Lens", *Microscopy Research and Technique*, 1996, vol. 33, pp. 441-479.

Kuszak, J. R. et al., "Fibre cell organization in crystalline lenses", *Experimental Eye Research*, vol. 78, 2004, pp. 673-687.

Kuszak, J. et al., "Gap Junctions of Chick Lens Fiber Cells", *Exp. Eye Res.*, vol. 27, 1978, pp. 495-498.

Kuszak, J. R. et al., "Lens Optical Quality and Lens Sutures", *Investigative Ophthalmology & Visual Science*, vol. 32, No. 7, Jun. 1991, pp. 2123-2129.

Kuszak, J. R. et al., "Lens Optical Quality is a Direct Function of Lens Sutural Architecture", *Investigative Ophthalmology & Visual Science*, vol. 32, No. 7, Jun. 1991, pp. 2119-2129.

Kuszak, J. R. et al., "Quantitative Analysis of Animal Model Lens Anatomy: Accommodative Range is Related to Fiber Structure and Organization", undated but prior to Jul. 2009, 26 pgs.

Kuszak, J. R. et al., "Suppression of Post-Vitrectomy Lens Changes in the Rabbit by Novel Benzopyranyl Esters and Amides", *Exp. Eye Res.*, vol. 75, 2002, pp. 459-473.

Kuszak, Jr et al., "The interrelationship of lens anatomy and optical quality II Primate Lenses", *Exp. Eye Res.*, vol. 59, 1994, pp. 521-535.

Kuszak, J. R. et al., "The Relationship Between Rabbit Lens Optical Quality and Sutural Anatomy after Vitrectomy", *Exp. Eye Res.*, vol. 71, 2000, pp. 267-281.

Kuszak Jer R. et al., "The Structure of the Vertebrate Lens", Chapter 4, undated but prior to Jul. 2009, pp. 71-118.

Kuszak, J. et al., "The Surface Morphology of Embryonic and Adult Chick Lens-Fiber Cells", *The American Journal of Anatomy*, vol. 159, 1982, pp. 395-410.

Kuszak, J. R. et al., "The Use of an Ex Vivo Mechanical Stretching Apparatus To Examine Fiber Ultrastructure During Accommodation", undated but prior to Jul. 2009, 1 pg.

Kuwabara, Toichiro, et al., "Electron Microscopic Study of Galactose-Induced Cataract", *Investigative Ophthalmology*, vol. 8, No. 2, Apr. 1969, pp. 133-149.

L'Esperance, Jr. "Ophthalmic Lasers Photocoagulation, Photoradiation and Surgery", $2^{nd}$ Edition, The C.V. Mosby Company, copyright 1983, pp. 529-538.

Lerman, Sidney, et al., "A Method for Detecting 8-Methoxypsoralen in the Ocular Lens", *Science*, vol. 197, Sep. 23, 1977, 1287-1288.

Lerman, Sidney, et al., "Photosensitization of the lens by 8-methoxypsoralen", *Invent. Ophthalmol. Visual Sci.*, vol. 16, No. 11, Nov. 1977, pp. 1065-1068.

Lerman, Sidney, M.D., "Photosensitizing Drugs and Their Possible Role in Enhancing Ocular Toxicity", *Ophthalmology*, vol. 93, No. 3, Mar. 1986, pp. 304-318.

Lerman, Sidney, et al., "Psoralen-long-wave Ultraviolet Therapy and Human Cataractogenesis", *Invent. Ophthalmol. Visual Sci.*, vol. 23, No. 6, Dec. 1982, pp. 801-804.

Lerman, Sidney, et al., "Spectroscopic Evaluation and Classification of the Normal, Aging, and Cataractous Lens", *Ophthl. Res.*, vol. 8, 1976, pp. 335-353.

Lim, Seung Jeong, M.D. et al., "Analysis of zonular-free zone and lens size in relation to axial length of eye with age", *J Cataract Refract Surg*, vol. 24, Mar. 1998, pp. 390-396.

Liu, Xinbing et al., "In vivo plasma-mediated ablation as a function of laser pulse width", *SPIE*, vol. 2975, 1997, pp. 282-288.

Loerscher, Hanspeter et al., "Noncontact Trephination of the Cornea Using a Pulsed Hydrogen Floride Laser", *American Journal of Ophthalmology*, vol. 104, Nov. 1987, pp. 471-475.

Loesel, Frieder H. et al., "Laser-Induced Optical Breakdown on Hard and Soft Tissues and Its Dependence on the Pulse Duration: Experiment and Model", *IEEE Journal of Quantum Electronics*, vol. 32, No. 10, Oct. 1996, pp. 1717-1722.

Lou, Marjorie F., et al., "Protein-Thiol Mixed Disulfides in Human Lens", published by Academic Press Limited, 1992, pp. 889-896.

Lubatschowski, Holger, "Surgical Laser System for the Treatment of Presbyopia", $7^{th}$ *Biotech in Europe Investor Forum*, Switzerland, Oct. 2-3, 2007, 9 pgs.

Lutze, Margaret et al., "Lenses of Diabetic Patients "Yellow" at an Accelerated Rate Similar to Older Normals", *Investigative Ophthalmology & Visual Science*, vol. 32, No. 1, Jan. 1991, pp. 194-199.

Maguen, Ezra, et al., "Excimer Laser Ablation of the Human Lens at 308 nm with a Fiber Delivery System", *J. Cataract Refract Surg.*, vol. 15, Jul. 1989, pp. 409-414.

Manns, Fabrice et al., "Radius of Curvature and Aspericity of the Anterior and Posterior Surface of Human Cadaver Crystalline Lenses", *Experimental Eye Research*, 2004, vol. 78, pp. 39-51.

Marion, II, John E. et al., "Medical Applications of Ultra-Short Pulse Lasers", *Proc. of SPIE*, vol. 3616, 1999, pp. 42-50.

Masters, B.R., "Three-dimensional Microscopic Tomographic Imaging of the Cataract in a Human Lens in Vivo", *Optics Express 332*, vol. 3, No. 9, Oct. 1998, pp. 332-338.

Mathias, R.T. et al., "Physiological Properties of the Normal Lens", *Physiological Reviews*, vol. 77, No. 1, Jan. 1997, pp. 21-50.

McBrien, N. A et al., "Experimental Myopia in a Diurnal Mammal (Sciurus Carolinesis) with No Accommodative Ability", *J. Physiol.*, vol. 469, 1993, pp. 427-441.

McCourt, M. E et al., Refractive State, Depth of Focus, and Accommodation of the Eye of the California ground squirrel (Spermophiliu Beecheyi), *Vision Res*, vol. 24, No. 10, 1984, pp. 1261-1266.

McDonald, Marguerita B., et al., "Central Photorefractive Keratectomy for Myopia, The Blind Eye Study", *Arch Ophthalmol*, vol. 108, Jun. 1990, pp. 799-808.

Michael, Ralph et al., "Refractive Index of Lens Fiber Membranes in Different Parts of the Crystalline Lens", *Proceedings of SPIE*, vol. 4611, 2002, pp. 159-164.

Moffat, B.A. et al., "Age-Related Changes in Refractive Index Distribution and Power of the Human Lens as Measured by Magnetic Resonance Micro-Imaging in Vitro", *Vision Research*, vol. 42, 2002, pp. 1683-1693.

Mutti, Donald O., et al., "A Video Technique for Phakometry of the Human Crystalline Lens", *Investigative Ophthalmology & Visual Science*, vol. 33, No. 5, Apr. 1992, pp. 1771-1781.

Myers, Raymond I. et al., "Feasibility of Using Lasers To Retard Cataract Development in the Ocular Lens by Restoring Lens Movement"; undated but prior to Jul. 2009, pp. 1-22.

Myers, Raymond I. et al., "Novel Approaches to Correction of Presbyopia With Laser Modification of the Crystalline Lens", *Journal of Refractive Surgery*, vol. 14, Mar./Apr. 1998; pp. 136-139.

Nanevicz, Tania M., et al., "Excimer Laser Ablation of the Lens", *Arch Ophthamol*, vol. 104, Dec. 1986, pp. 1825-1829.

Neev, Joseph, "Ultrashort Pulse Lasers: A New Tool for Biomedical Applications", *SPIE*, vol. 3255; pp. 2-7.

Nichamin, Louis D., "Treating astigmatism at the time of cataract surgery", *Current Opinion in Ophthalmology*, 2003, vol. 14, p. 35-38.

Oberheide, Uwe et al., "Therapy Monitoring of Laser Cyclophotocoagulation", *Proceedings of SPIE*, vol. 4611, 2002, pp. 48-53.

O'Donnell, Colleen B., et al., "Ablation Smoothness as a Function of Excimer Laser Delivery System", *J. Cataract Refract Surg.*, vol. 22, Jul./Aug. 1996, pp. 682-685.

O'Donnell, Colleen B., et al., "Surface Roughness in PMMA is Linearly Related to the Amount of Excimer Laser Ablation", *Journal of Refractive Surgery*, vol. 12, Jan./Feb. 1996, pp. 171-174.

Oriowo, Olanrewaju Matthew, "A Study of Ultraviolet Radiation Effects on Procine Crystalline Lens and Development of a New Assay Methodology for UV Cataractogenesis Investigation", *A Thesis Presented to the University of Waterloo*, 2000, pp. i-xix and 1-218.

Ostrin, Lisa A. et al., "Effects of Pirenzepine on Pupil Size and Accommodation in Rhesus Monkeys", *Investigative Ophthalmology & Visual Science*, Oct. 2004, vol. 45, No. 10, pp. 3620-3628.

Ostrin, Lisa A. et al., "The Effects of Phenylephrine on Pupil Diameter and Accommodation in Rhesus Monkeys"; *Investigative Ophthalmology & Visual Science*, 2004, vol. 45, No. 1, pp. 215-221.

Ostrin, Lisa A. et al., "Comparisons Between Pharmacologically and Edinger-Westphal-Stimulated Accommodation in Rhesus Monkeys", *Investigative Ophthalmology & Visual Science*, 2005, vol. 46, No. 2, pp. 609-617.

Parel, Jean-Marie et al., "Intraocular Implants for the Surgical Correction of Presbyopia"; *In Ophthalmic Technologies X*, Proceedings of SPIE, vol. 3908, 2000, pp. 115-122.

Patel, C.K. et al., "The Ageing Lens", *Association of Optometrists, City University, London*; undated, www.optometry.co.uk; pp. 27-31.

Pau, Hans et al., "The increasing sclerosis of the human lens with age and its relevance to accommodation and presbyopia", *Graefe's Arch Clin Exp. Ophthalmol.*, (1991) vol. 229, pp. 294-296.

Payne, Peter A. et al., "Ophthalmic Applications of Laser-Generated Ultrasound"; *SPIE*, vol. 3908, 2000, pp. 13-22.

Peterson, Jennifer A. et al., "Intraocular Pressure Measurement in Cynomolgus Monkeys, Tono-Pen Versus Manometry", *Investigative Ophthalmology & Visual Science*, 1996, vol. 37, No. 6, pp. 1197-1199.

Prokofeva, G. I et al., "Effects of Low-Intensity Infrared Laser Irradiation on the Eye, (An Experimental Study)", *Vestn. Oftalmol.*, vol. 112, No. 1, 1996, pp. 31-32, with English Abstract, 5 pgs.

Puliafito, Carmen A., M.D. et al., "High-Speed Photography of Excimer Laser Ablatio of the Cornea", *Arch Ophthalmol*, vol. 105, Sep. 1987, pp. 1255-1259.

Qian, Wen et al., "3 Year Simvastatin Treatment and Lens Nuclear Back Scattering"; *J Ophthalmol*, vol. 84, 2000, pp. 512-516.

Qian, Wen et al., "Universal Opacity Standard for Scheimpflug Photography", *Ophthalmic Res*, 2000, vol. 32, pp. 292-298.

Rafferty, Nancy et al., "Lens Wound Healing and Cataractogenesis in a Pigmented Eye", *Exp. Eye Res.* (1984) 38, 267-277.

Riley, Michael V., et al., "The Effects of UV-B Irradiation on the Corneal Endothelium", *Eye Research Institute of Oakland University*, 1987, pp. 1021-1033.

Ripken, T. et al., "FEM Simulation of the Human Lens Compared to Ex-Vivo Porcine Lens Cutting Pattern: A Possible Treatment of Presbyopia"; undated, 11 pgs.
Ripken T. et al., "First in-vivo studies of Presbyopia treatment with ultrashort laser pulses", *Proc. Spie 5142*, vol. 137, 2003, p. p.
Ripken, T. et al., "Fs-laser Induced Elasticity Changes to Improve Presbyopic Lens Accommodation", undated, 10 pgs.
Ripken T. et al., "Investigations for the correction of Presbyopia by fs-laser induced cuts", *Proc. SPIE 5314*, vol. 27, 2004, 9 pgs.
Rockwell, B.A. et al., "Safe Use of Ultra-short Lasers"; *SPIE*, vol. 3616, 1999, pp. 32-39.
Roesner, C.A.D. et al., "Light-Matter Interactions on the Femtosecond Time Scale", *Department of Physics and Division of Engineering and Applied Sciences, Harvard University*; undated, pp. 1-27.
Rol, Pascal et al., "An Optomechanical Eye Model for Observation of Lens Photoablation"; *SPIE*, 1997, vol. 2971, pp. 171-174.
Sacks, Zachary S. et al., "Laser Spot Size as a Function of Tissue Depth and Laser Wavelength in Human Sclera", *SPIE*, 1998, vol. 3255, pp. 67-76.
Scammon, Richard J. et al., "Simulations of Shock Waves and Cavitation Bubbles Produced in Water by Picosecond and Nanosecond Laser Pulses", *SPIE*, 1998, vol. 3254, pp. 264-275.
Schachar, Ronald A. MD, PhD., et al., "A Revolutionary Variable Focus Lens", *Annals of Ophthalmology*, vol. 28, No. 1, Jan./Feb. 1996, pp. 11-18.
Schachar, Ronald A., M.D., "Cause and Treatment of Presbyopia With a Method for Increasing the Amplitude of Accommodation", *Annals of Ophthalmol*, 1992; 24:445-452.
Schachar, Ronald A., M.D. et al., "Experimental Destruction of Cataractous Lenses by Laser", *Ophthalmic Surgery*, Surgical Forum, pp. 506-509.
Schachar, Ronald A., M.D. et al., "Experimental Support for Schachar's Hypothesis of Accommodation", *Ann Ophthalmol*, 1993; 25: 404-409.
Schachar, Ronald A., MD, PhD, "Histology of the Ciliary Muscle-Zonular Connections", *Annals of Ophthalmology*, vol. 28, No. 2, Mar./Apr. 1996, 70-79.
Schachar, Ronald A. MD et al., "Mechanism of Human Accommodation as Analyzed by Nonlinear Finite Element Analysis", *Ann Ophthalmol*; 2001; vol. 33, No. 2, pp. 103-112.
Schachar, Ronald A., MD, PhD, "Pathophysiology of Accommodation and Presbyopia, Understanding the Clinical Implications", *J. Florida M.A.*, vol. 81, No. 4, Apr. 1994, pp. 268-271.
Schaeffel, Frank, "Kappa and Hirschberg Ratio Measured With an Automated Video Gaze Tracker", *Optometry and Vision Science*, 2002, vol. 79, No. 5, pp. 329-334.
Schaffer, Chris B. et al., "Dynamics of Femtosecond Laser-Induced Breakdown in Water From Femtoseconds to Microseconds", *Optics Express*, 2002, vol. 10, No. 3, pp. 196-203.
Schaffer, Chris B. et al., "Morphology of Femtosecond Laser-Induced Structural Changes in Bulk Transparent Materials", *Applied Physics Letters*, vol. 84, No. 9, 2004, pp. 1441-1443.
Shen, Nan, et al., "Ablation of Cytoskeletal Filaments and Mitochondria in Live Cells Using a Femtosecond Laser Nanoscissor", *MCB*, 2005, vol. 2, No. 1, pp. 17-25.
Shen, Nan; "Photodisruption in Biological Tissues Using Femtosecond Laser Pulses", *A Thesis Presented to the Department of Physics, Harvard University*, 2003, pp. 1-125.
Shen, Nan, et al., "Photodisruption in Biological Tissues and Single Cells Using Femtosecond Laser Pulses", undated, 2 pgs.
Shen, Nan, et al., "Surface and Bulk Photodisruption in Turbid Tissue Using Femtosecond Laser Pulses", *Department of Physics and Division of Engineering and Applied Sciences, Harvard University*, undated, pp. 1-24.
Sher, Neal A., MD, "Hyperopic Refractive Surgery", *Current Opinion in Ophthalmology*, 2001, vol. 12, pp. 304-308.
Sivak, Jacob G., "Through the Lens Clearly: Phylogeny and Development, The Proctor Lecture", *Ophthalmology & Visual Science*, 2004, vol. 45, No. 3, pp. 740-747.
Sliney, D. H et al., "Medical Lasers and Their Safe Use", *Springer Verlag*, New York, 1993, pp. 42-50.
Slingsby, Christine, "Lens Crystallin Crystal Structures", undated article. 3 pgs.
Söderberg, Per G., et al., "Angular Dependence of the Intensity of Back Scattered Light From Human Lenses With Nuclear Cataract, Implications for Measurement", *SPIE*, 2000, vol. 3908, pp. 34-37.
Söderberg, Per G., et al., "External Standard for Measurements with the Scheimpflug Slitlamp Microscope", *SPIE*, 1997, vol. 2971, pp. 8-13.
Solomon, Ira Seth, M.D., "Aqueous Humor Dynamics", undated, 17 pgs.
Spector, Abraham, "Aging of the Lens and Cataract Formation", *Aging and Human Visual Function*, pp. 27-43.
Srinivasan, R., "Ablation of Polymers and Biological Tissue by Ultraviolet Lasers", Oct. 1986, pp. 932-935.
Srinivasan R. et al., "Excimer Laser Surgery of the Cornea", *American Journal of Ophthalmology*, vol. 96, 1993, pp. 710-715.
Stitzel, Joel D., et al., "A Nonlinear Finite Element Model of the Eye With Experimental Validation for the Prediction of Globe Rupture", *Stapp Car Crash Journal*, 2002, vol. 45, 24 pgs.
Stitzel, Joel D., et al., "Blunt Trauma of the Aging Eye", *Arch Ophthalmol*, 2005, vol. 123, pp. 789-794.
Strauss, Moshe, et al., "Two-Dimensional Rayleigh Model of Vapor Bubble Evolution", *SPIE*, 1999, vol. 3601, pp. 212-224.
Strenk, Susan A., et al, "Age-Related Changes in Human Ciliary Muscle and Lens: A Magnetic Resonance Imaging Study", *Investigative Ophthalmology & Visual Science*, 1999, vol. 40, No. 6, pp. 1162-1169.
Strenk, Susan A. et al., "Magnetic Resonance Imaging Study of the Effects of Age and Accommodation on the Human Lens Cross-Sectional Area", *IOVS*, 2004, Vo. 45, No. 2, pp. 539-545.
Strenk, Susan A., et al, "The Mechanism of Presbyopia", *Progress in Retinal and Eye Research*, 2004 vol. 11, pp. 1-15.
Sweeney, Matthew H.J., et al., "Movement of Cysteine in Intact Monkey Lenses: The Major Site of Entry is the Germinative Region", *Experimental Eye Research*, 2003, vol. 77. pp. 245-251.
Swegmark, Gunnar, "Studies With Impedance Cyclography on Human Ocular Accommodation At Different Ages", *ACTA Ophthalmologica*, vol. 47, 1969, pp. 1186-1206.
Taboada, J., et al., "Optically Coupled Technique for Photorefractive Surgery of the Cornea", *Optics Letters*, vol. 15, No. 9, May 1, 1990, pp. 458-460.
Taboada, J. et al., "Response of the Corneal Epithelium to KrF Excimer Laser Pulses", *Health Physics*, vol. 30, 1981, pp. 677-683.
Tahi, Hassan, et al., "Restoring Accommodation: Surgical Technique and Preliminary Evaluation in Rabbits", *SPIE*, 1999, vol. 3591, pp. 267-269.
Tamm, Svenja, et al., "Age-Related Changes of the Human Ciliary Muscle. A Quantitative Morphometric Study", *Mechanisms of Aging and Development*, vol. 62, 1992, pp. 209-221.
Tang, Daxin; "Influence of Age, Diabetes, and Cataract on Calcium, Lipid-Calcium, and Protein-Calcium Relationships in Human Lenses", *Investigative Ophthalmology & Visual Science*, 2003, vol. 44, No. 5, pp. 2059-2066.
Taylor, Virginia L. et al., "Morphology of the Normal Human Lens", *Investigative Ophthalmology & Visual Science*, Jun. 1996, vol. 37, No. 7, pp. 1396-1410.
Topilow, Harvey W., M.D., "Vitreous Changes in Retinal Branch Vein Occlusion", *Arch Ophthalmol*, vol. 105, Sep. 1987.
Trokel, Stephen L., M.D., et al., "Excimer Laser Surgery of the Cornea", *American Journal of Ophthalmology*, vol. 96, No. 6, Dec. 1983, 710-715.
Tsai, Philbert S., "All-Optical, In-Situ Histology of Neuronal Tissue with Femtosecond Laser Pulses", *Imaging in Neuroscience and Development*, CSHL Press, undated, 12 pgs.
Tsubota, Kazuo, "Application of Erbium: YAG Laser in Ocular Ablation", *Ophthalmologica*, 1990, 200:pp. 117-122.
Van Alphen, G.W.H.M. et al., "Elasticity of Tissues Involved in Accommodation", *Vision Res.*, vol. 31, No. 7/8, 1991, pp. 1417-1438.
Venugopalan, V. et al., "The Thermodynamic Response of Soft Biological Tissues to Ultraviolet Laser Irradiation", *Biophysical Journal*, vol. 60, Oct. 1995, pp. 1258-1271.

Vilupuru, Abhiram S., "Optical and Biometric Relationships of the Isolated Pig Crystalline Lens", *Ophthal. Physiol. Opt.*, 2001, vol. 21, No. 4, pp. 296-311.

Vilupuru, Abhiram S., "Spatially Variant Changes In Lens Power During Ocular Accommodation In A Rhesus Monkey Eye", *Journal of Vision*, 2004, vol. 4, pp. 299-309.

Vogel, Alfred et al., "Factors Determining the Refractive Effects of Intrastromal Photorefractive Keratectomy with the Picosecond Laser", *J. Cataract Refract Surg.*, vol. 23, Nov. 1997, pp. 1301-1310.

Vogel, Alfred et al., "Interaction of Laser-Produced Cavitation Bubbles With an Elastic Tissue Model", *SPIE*, 2001, vol. 4257, pp. 167-177.

Vogel, Alfred et al., "Intraocular Photodisruption With Picosecond and Nanosecond laser Pulses: Tissue Effects in Cornea, Lens and Retina", *Investigative Ophthalmology & Visual Science*, Jun. 1994, No. 7, vol. 35, pp. 3032-3044.

Vogel, Alfred et al., "Kinetics of Phase Transitions in Pulsed IR Laser Ablation of Biological Tissues", *SPIE*, 2003, vol. 4961, pp. 66-74.

Vogel, Alfred et al., "Laser-Induced Breakdown in the Eye At Pulse Durations From 80 ns to 100 fs", *SPIE*, 1998, vol. 3255, pp. 34-49.

Vogel, Alfred et al., "Numerical Simulation of Optical Breakdown for Cellular Surgery At Nanosecond to Femtosecond Time Scales", *SPIE*, 2001, vol. 4433, pp. 70-80.

Vrensen, G. F. J. M., "Aging of the human eye lens—A morphological point of view", *Comp. Biochem. Physiol.*, vol. 111A, 1995. pp. 519-553.

Waring III, George O., M.D., "Presbyopia and Accommodative Intraocular Lenses—the Next Frontier in Refractive Surgery?", *Refractive & Corneal Surgery*, vol. 8, Nov./Dec. 1992, pp. 421-423.

Weale, Robert D., SC., "Presbyopia Toward the End of the 20th Century", *Survey of Opthalmology*, vol. 34, No. 1, Jul.-Aug. 1989, pp. 15-29.

Werblin, Theodore P., M.D., "Should We Consider Clear Lens Extraction for Routine Refractive Surgery?", *Refractive & Corneal Surgery*, vol. 8, Nov./Dec. 1992, pp. 480-481.

Werner, Liliana, MD, et al., "Capsular Bag Opacification After Experimental Implantation of a New Accommodating Intraocular Lens in Rabbit Eyes", *J Cataract Refract Surg.*, 2004, vol. 30, pp. 1114-1123.

Werner, Liliana, MD. et al., "Posterior Capsule Opacification in Rabbit Eyes Implanted With 1-Piece and 3-Piece Hydrophobic Acrylic Intraocular Lenses", *J Cataract Refract Surg*, 2005, vol. 31, pp. 805-811.

Wyatt, Harry J., "Application of a Simple Mechanical Model of Accommodation to the Aging Eye", *Eye Res.*, vol. 33, No. 5/6, 1993, pp. 731-738.

Ziebarth, Nöel, et al; "Non-contact Optical Measurement of Lens Capsule Thickness During Simulated Accommodation", *SPIE*, 2005, vol. 5688, pp. 19-25.

Zuclich, Joseph a. et al., "A comparison of laser-induced retinal damage from infrared wavelengths to that from visible wavelengths", *Lasers and Light*, vol. 8, No. 1, 1997, pp. 1529.

Zuclich, Joseph a. et al., "In Situ Measurements of Lens Fluorescence and its Interference With Visual Function", *Investigative Ophthalmology & Visual Science*, vol. 33, No. 2, 1993, pp. 410-415.

Zuclich, Joseph, "In Vivo Measurements of Optical Properties of the Ocular Lens", Reprinted from Proceedings of Ultraviolet Radiation Hazards, Jan. 26-27, 1994, *SPIE-The International Society for Optical Engineering*, Vo. 2134B Ultraviolet Radiation Hazards, 1994, pp. 99-112.

Zuclich, J.A., et al., "Ocular Effects of Penetrating IR Laser Wavelengths", Reprinted from Proceedings of Laser-Tissue Interaction VI, Feb. 6-9, 1995, *SPIE-The International Society for Optical Engineering*, vol. 2391, 1995, pp. 111-125.

Zuclich, Joseph A., et al., "Rapid Noninvasive Optical Characterization of the Human Lens", *Lasers in the Life Sciences*, 6(1), 1994, pp. 39-53.

Zuclich, Joseph A., "Research on the Ocular Effects of Laser Radiation", Published by *Technology Incorporated: Life Sciences Division*, publication date unknown, 59 pgs.

Zuclich, Joseph A., "Ultraviolet-Induced Photochemical Damage in Ocular Tissues", *Health Physics*, vol. 56, No. 5, May 1989, pp. 671-681.

Zuclich, Joseph A., "Workshop on Long-Term Visual Health Risks of Optical Radiation—Thermal Cataracts Induced by UV Laser Radiation", *Workshop Report, Cataract Working Group*, publisher unknown, publication date unknown, 13 pgs.

Agrahari, S. et al., "The Potential of Photodisruption Laser Treatment of the Crystalline Lens to Rupture the Lens Capsule", *ARVO Abstract No.* 07-A-6800, 2006, 1 pg.

Faraggi, E. et al., "Stress confinement, shock wave formation and laser induced damage", Conference 5695: Optical Interactions with Tissue and Cells XVI, *Photonics West*, undated, 1 pg.

Fisher, R F, "The ciliary body in accommodation", *Trans Ophthalmol. Soc. UK*, 1989, vol. 105, 1 pg.

Fisher, RF. "The mechanics of accommodation in relation to presbyopia", *Eye*, 1988, vol. 2, 1 pg.

Frey, R. W. et al., "Modification of Lens Mechanics of Human Cadaver and Porcine Lenses Using Photodisruption Laser to Change Lens Power and Increase Flexibility", *ARVO Abstract No.* 07-A-06652, 2006, 1 pg.

Garner, LF et al., "Changes in equivalent and gradient refractive index of the crystalline lens with accommodation", *Optom Vis. Sci.*, 1997, vol. 74, 1 pg.

Garner LF et al., "Changes in ocular dimensions and refraction with accommodation", *Ophthalmic Physiol. Opt.*, 1997, vol. 17, 1 pg.

Gray, G. et al., "Constructions of a Computer Mesh Model of the Anatomical Human Crystalline Lens Fiber Ultrastructure", *ARVO Abstract*, 2006, 1 pg.

Helsterkamp, A. et al., "Nanosurgery in live cells using ultrashort laser pulses", Conference 5695: Optical Interactions with Tissue and Cells XVI, *Photonics West*, undated, 1 pg.

Kuszak, J.R., "Progressively More Complex Star Sutures Formed in Primate Lenses During Periods of Development, Growth and Aging Are Related to Accommodation", *Abstracts Online*, obtained from the Internet on Apr. 19, 2006 at: http://www.abstractsonline.com/viewer/viewAbstractPrintFriendly.asp?CKey={C8FDF5D . . . 4/19/06, I page.

Kuszak, J. R. et al., "Results From a Finite Element Model Analysis of the Accommodative Process Based on the Human Crystalline Lens Fiber Ultrastructure", *ARVO Abstract*, 2006, 1 pg.

McBrien NA et al., "Experimental myopia in a diurnal mammal (Sciurus carolinensis) with no accommodative ability", *J Physiol.*, 1993, vol. 469, 1 pg.

McCourt ME et al., "Refractive state, depth of focus and accommodation of the eye of the California ground squirrel (Spermophilus beecheyi)", *Vision Res.*, 1984, vol. 24, 1 pg.

Oberheide, U. et al., "Flexibility Increase of Human Donor Lenses After Femosecond Laser Treatment (fs-Lentotomy)", *ARVO Abstract No.* 3833/B571, 2007, 2 pgs.

Olmstead, T. et al., "The Use of an Off Axis Slit Laser Camera System for Determining Photodisruptive Laser Placement in Lenses", *ARVO Abstract No.* 07-A-6567, 2006, 1 pg.

Rafferty, NS. et al., "Comparative study of actin filament patterns in lens epithelial cells, Are these determined by the mechanisms of lens accommodation?", *Curr Eye Res.*, 1989, vol. 8, 1 pg.

Roa, Ch. Mohan et al., "Level of Reduced Nucleotides and Lens Photodamage", *National Eye Institute*, undated, 1 pg.

Subramaniam, H. et al., "Finite Element Analysis of the Accommodative Process in the Whole Globe", *ARVO Abstract No.* 07-A-6249, 2006, 1 pg.

Van Alphen GW et al., "Elasticity of tissues involved in accommodation", *Vision Res.*, 1991, vol. 31, 1 pg.

Wang, B. et al., "In-vivo animal studies on intraocular nanosurgery with low-energy 80 MHZ near infrared femtosecond laser pulses", Conference 5695: Optical Interactions with Tissue and Cells XVI, *Photonics West*, undated, 1 pg.

Yeilding, R. H. et al., "Lens Culture System for Long Term Study of Porcine Lenses Pre and Post Laser Photodisruption Treatment", *ARVO Abstract No.* 01-A-6495, 2006, 1 pg.

Zepkin, N. et al., "Measurement of Temperature Rise in Porcine Crystalline Lenses from a Photodisruption Laser", *ARVO Abstract No.* 07-A-6709, 2006, 1 pg.

Zoltoski, R. K. et al., "Reverse Engineering of Human Lenses", *ARVO Abstract No.* 2018/B159, 2007, 2 pgs.

Avro, "Statement for the Use of Animals in Ophthalmic and Visual Research", *The Association for Research in Vision and Ophthalmology*, copyright © 2002, obtained from the Internet on Jan. 15, 2005 at: http://www.avro.org/AboutAvro/animalst.asp, 3 pgs.

Gattass, Rafael et al., "Femtosecond laser micromaching Applications in Technology and Biology", Photonics West conference Jan. 2005, 78 pgs.

Hermans, E. et al., "Estimating the External Force Acting on the Human Eye Lens During Accommodation Using Finite Elements Modeling", presentation on Accommodation & Presbyopia, May 2005, 1 pg.

Kuszak et al., "Light, scanning and electron micrographs have lead to the following interpretations of secondary fiber formation", 2004, 16 pgs.

Lubatschowski, H. et al., "Treatment of Presbyopia by Cutting the Cystaline Lens: A Comparison of FEM Simulation and Ex vivo Studies", *Lazer Zentrum Hannover e.V.*, Publication date unknown, 22 pgs.

Mazur, Eric, "An Introduction to Femtosecond Laser Science", Photonics West conference Jan. 2005, 291 pgs.

Nebel, Achim et al., "Fast Micromachining using Picosecond Lasers", Photonics West conference Jan. 2005, 37 pgs.

OSN SuperSite, "Increase in lens stiffness with age may cause presbyopia, study suggests", 2005, 1 pg.

"Presbyopia—preconditions", *Laser Zentrum Hannover*, undated, 11 pgs.

"Principles of Ultrafast Laser Surgery Femtosecond Laser-Tissue Interaction", copyright © Center for Ultrafast Optical Sciences, Un. of Michigan, undated, 3 pgs.

Roundy, Carlos—"Propagation factor qualifies leaser bean performance", *Laser World Focus*, undated, 3 pgs.

Shen, J. et al. "Measurement of the Lens Capsule Contraction Force in the Radial Direction", presentation on Accommodation & Presbyopia, May 2005, 1 pg.

Figure 4.2—Optical constants for a "standard eye", publication unknown, undated, 1 pg.

Picture of an eye obtained from the Internet on Mar. 28, 2005 at: http://www.opt.uh.edu/research/aglasser/aao/gonioani.gif, 1 pg.

Pictures of eyes, date and publisher unknown, 5 pgs.

Loesel paper graphs, date and publisher unknown, 2 pgs.

U.S. Appl. No. 11/337,127, filed Jan. 20, 2006, Frey et al.
U.S. Appl. No. 11/414,819, filed May 1, 2006, Frey et al.
U.S. Appl. No. 12/217,285, filed Jul. 2, 2008, Frey et al.
U.S. Appl. No. 12/217,295, filed Jul. 2, 2008, Frey et al.
U.S. Appl. No. 12/509,021, filed Jul. 24, 2009, Frey et al.
U.S. Appl. No. 12/509,211, filed Jul. 24, 2009, Frey et al.
U.S. Appl. No. 12/509,412, filed Jul. 24, 2009, Frey et al.
U.S. Appl. No. 12/685,850, filed Jan. 12, 2010, Myers et al.
U.S. Appl. No. 12/831,845, filed Jul. 7, 2010, Naranjo-Tackman et al.
U.S. Appl. No. 12/831,859, filed Jul. 7, 2010, Naranjo-Tackman et al.
U.S. Appl. No. 12/840,818, filed Jul. 21, 2010, Porter et al.
U.S. Appl. No. 12/842,870, filed Jul. 23, 2010, Frey et al.
U.S. Appl. No. 29/377,018, filed Oct. 15, 2010, Bott et al.
U.S. Appl. No. 29/377,054, filed Oct. 15, 2010, Bott et al.
U.S. Appl. No. 13/016,593, filed Jan. 28, 2011, Frey et al.
U.S. Appl. No. 13/017,499, filed Jan. 31, 2011, Frey et al.
U.S. Appl. No. 13/017,702, filed Jan. 31, 2011, Frey et al.
U.S. Appl. No. 13/243,406, filed Sep. 23, 2011, Myers et al.
U.S. Appl. No. 13/273,653, filed Oct. 14, 2011, Frey et al.
U.S. Appl. No. 13/427,130, filed Mar. 22, 2012, Frey.
U.S. Appl. No. 13/427,149, filed Mar. 22, 2012, Frey et al.
U.S. Appl. No. 13/427,319, filed Mar. 22, 2012, Grey et al.
U.S. Appl. No. 13/435,103, filed Mar. 30, 2012, Curatu et al.
U.S. Appl. No. 13/681,004, filed Nov. 19, 2012, Frey et al.

FDA PMA P030002 titled "crystalens™ Model AT-45 Accomodating Posterior Chamber Intraocular Lens (OIO)", dated Nov. 14, 2003, 16 pgs.

FDA PMA P040020 titled "AcrySof® ResSTOR® Apodized Diffractive Optic Posterior Chamber Intraocular Lenses, Models MA60d3 and SA60D3", dated Mar. 21, 2005, 29 pgs.

International Search Report and Written Opinion for related application No. PCT/US2010/043255, dated Sep. 16, 2010, 10 pgs.

Unpublished U.S. Appl. No. 13/681,004, filed Nov. 19, 2012 (57 pgs).

Author unknown, "Statement of the Use of Animals in Opthalmic and Visual Research", The Association for Research in Vision and Opthalmology, Obtained from the Internet at: http//www.arvo.org/aboutavro as of Nov. 18, 2010, 3 pgs.

Akchurin, Garif et al., "Evaluation of the degree of turbidity if cataract lens and its correlation with retinal visual acuity", *SPIE*, vol. 3591, Jan. 1999, pp. 74-81.

Al-Ghoul, K. J. et al., "Distribution and Type of Morphological Damage in Human Nuclear Age-Related Cataracts", *Department of Cell Biology and Anatomy, University of North Carolina and Duke University Eye Center*, 1996, pp. 237-251.

Al-Ghoul, Kristin J. et al., "Structural Evidence of Human Nuclear Fiber Compaction as a Function of Ageing and Cataractogenesis", *Exp. Eye Res.*, vol. 72, 2001, pp. 199-214.

Alio, et al., "Crystalline Lens Optical Dysfunction through Aging", *Ophthalmology*, vol. 112, No. 11, Nov. 2005, pp. 2022-2029.

Amann, Josef et al., "Increased Endothelial Cell Density in the Paracentral and Peripheral Regions of the Human Cornea", *American Journal of Ophthalmology*, vol. 135, No. 5, May 2003, pp. 584-590.

Amendt, M. Strauss et al., "Modeling of bubble dynamics in relation to medical applications", *Proc. of SPIE*, vol. 2975, 1997, pp. 362-373.

Ansari, Rafat R. et al., "Measuring lens opacity: combining quasi-elastic light scattering with Scheimpflug imaging system", *Proc. of SPIE*, vol. 3246, 1998, pp. 35-42.

Anschutz, Till, M.D., "Laser Correction of Hyperopia and Presbyopia", vol. 34, No. 4, 1994, pp. 107-137.

Apple, David J. et al., "Preparation and Study of Human Eyes Obtained Postmortem with the Miyake Posterior Photographic Technique", *Ophthalmology*, vol. 97, No. 6, Jun. 1990, pp. 810-816.

Armstrong, Larry "A cataract Breakthrough May Be on the Way", *Business Week*, Mar. 23, 1998, pp. 90-92.

Aston, Adam, "Why Settle for 20/20?", *Business Week*, Mar. 17, 2003, pp. 95-96.

Azzam, Naiel et al., "Long-term lens organ culture system to determine age-related effects of UV irradiation on the eye lens", *Experimental Eye Research*, vol. 79, 2004, pp. 903-911.

Back, Arthur P. et al., "Correction of Presbyopia with Contact Lenses: Comparative Success Rates with Three Systems", *Optometry & Vision Science*, 1989, vol. 66, No. 8, pp. 518-525.

Balaram, Mini et al., Noncontact Specular Microscopy of Human Lens Epithelium, *IOVS*, vol. 41, No. 2, Feb. 2000, pp. 474-481.

Barak, Adiel et al., "Anterior capsulotomy using the $CO_2$ laser", *Proc. of SPIE*, vol. 3246, 1998, pp. 196-198.

Bath, Patricia E. et al., "Endocapsular Excimer Laser Phakoablation Through a 1-mm Incision", *Opthalmic Laser Therapy*, vol. 2, No. 4, 1987, pp. 245-249.

Beers, A. P. A. et al. "Age-Related Changes in the Accommodation Mechanism", *Optometry and Vision Science*, 1996, vol. 73, No. 4, pp. 235-242.

Beers, A. P. A. et al., "In Vivo Determination of the Biomechanical Properties of the Component Elements of the Accommodation Mechanism", *Vision Res.*, vol. 34, 1994, pp. 2897-2905.

Bellows, John G., M.D. et al., "B. Cataracta Complicata", *Traumatic Cataract*, undated but prior to Jul. 2009, pp. 270-272.

Ben-Sira, I. et al., "Clinical method for measurement of light back scattering from the in vivo human lens", *Invest. Ophthalmol. Vis. Sci.*, vol. 19, No. 4 (Reports), Apr. 1980, pp. 435-437.

Benjamin, William J., "Bo rish's Clinical Refraction", W.B. Saunders, publishers, copyright 1998, p. 110.

Bettelheim, Frederick A. et al., "Syneretic Response of Aging Normal Human Lens to Pressure", *Investigative Ophthalmology & Visual Science*, vol. 44, No. 1, Jan. 2003, pp. 258-263.

Bigler, Emmanuel, "Depth of field and Scheimpflug's rule: a "minimalist" geometrical approach", published unknown, 2002, pp. 1-17.

Billie, J. F. et al., "3D Imaging of the Human Eye Using the laser Tomographic Scanner Lts", publisher unknown, undated but prior to Jul. 2009, 2 pgs.

Bito, L.Z. et al., "Age-dependent loss of accommodative amplitude in rhesus monkeys: an animal model for presbyopia", *Invest. Ophthalmol. Vis. Sci.*, vol. 23, No. 1, Jul. 1982, pp. 23-31.

Bliss, E. S., "Pulse Duration Dependence of laser Damage Mechamisms", *Opto-Electronics*, vol. 3, 1971, pp. 99-108.

Bor, Zs. PhD., et al., "Plume Emission, Shock Wave and Surface Wave Formation During Excimer Laser Ablation of the Cornea", *Supplement to Retroactive & Corneal Surgery*, vol. 9, Mar./Apr. 1993, pp. S111-S115.

Borja, David et al., "Crystalline Lens MTF Measurement During Simulated Accommodation", *Proc. of SPIE*, 2005, vol. 5688, pp. 26-32.

Borkman, Raymond F. et al., "Evidence for a Free Radical Mechanism in Aging and u.v.-Irradiated Ocular Lenses", *Exp. Eye Res.*, 1977, vol. 25, pp. 303-309.

Braham, Lewis, "Eye Surgery: It's Getting Sharper", *Business Week*, Oct. 18, 2004, pp. 142-143.

Breitenfeld, P. et al., "Finite Element Method-Simulation of the Human Lens During Accommodation", publiasher unknown, vol. 5863, 2005, 9 pgs.

Breitling, Detlef et al., "Fundamental aspects in machining of metals with short and ultrashort laser pulses", *Proc. of Spie*, vol. 5339, 2004, pp. 1-15.

Brian, G. et al., "Cataract Blindness—Challenges for the $21^{st}$ Century", *Bulletin of the World Health Organization*, vol. 79, No. 3, 2001, pp. 249-256.

Bron, A.J., "The Ageing Lens", *Opthalmologics*, vol. 214, 2000, pp. 86-104.

Brown, Nicholas, "Dating the onset of cataract", *Transactions of the Ophthalmological Society of the United Kingdom*, vol. 96, 1976, pp. 18-23.

Brown, Nicholas "The Change in Lens Curvature with Age", *Exp. Eye Res.* (1974), vol. 19, pp. 175-183.

Brown, Nicholas "The Change in Shape and Internal Form of the Lens of the Eye on Accommodation", *Exp. Eye Res.* (1973) vol. 15, pp. 441-459.

Burd, H.J. et al., "Can reliable values of Young's modulus be deduced from Fisher's (1971) spinning lens measurements?", *Vision Research*, vol. unknown, 2005, pp. 1-15.

Burd, H.J. et al., "Numerical modeling of the accommodating lens", *Vision Research*, vol. 42, 2002, pp. 2235-2251.

Campbell, Melanie C. W., "Measurement of Refractive Index in an Intact Crystalline Lens", *Vision Research*, vol. 24, No. 5, 1984, pp. 409-415.

Carey, James et al., "Propagation and Characterization of Ultrashort Laser Pulses", Harvard University, 2003, pp. 1-30.

Chaker, M. et al., "Interaction of a 1 psec laser pulse with solid matter", *Phys. Fluids B 3*, vol. 1, Jan. 1991, pp. 167-175, plus cover page.

Charles, M. W. et al., "Dimensions of the Human Eye Relevant to Radiation Protection", *Phys. Med. Biol.*, 1975, vol. 20, No. 2, © 1975, pp. 202-218.

Chen, Wei-Li et al., Ultrasound Biomicroscopic Findings in Rabbit Eyes Undergoing Scleral Suction during Lamellar Refractive Surgery, *IOVS*, vol. 43, No. 12, Dec. 2002, pp. 3665-3672.

Chien, C. Y. et al., "Production of a high-density and high-temperature plasma with an intense high-contrast subpicosecond laser", *Optics Letters*, vol. 18, No. 18, Sep. 15, 1993, pp. 1535-1537.

Claflin, E. S. et al., "Configuring an electrostatic membrane mirror by least-squares fitting with analytically derived influence functions", *J. Opt. Soc. Am. A.*, vol. 3, No. 11, 1986, pp. 1833-1839.

Coleman, D. Jackson et al., "Presbyopia, Accommodation, and the Mature Catenary", *Ophthalmology*, vol. 108, No. 9, Sep. 2001, pp. 1544-1551.

Cook, Christopher A. et al., "Aging of the Human Crystalline Lens and Anterior Segment", *Vision Res.*, 1994, vol. 34, No. 22, pp. 2945-2954.

Corkum, P. B. et al., "Thermal Response of Metals to Ultrashort-Pulse Laser Excitation", *Physical Review Letters*, vol. 61, No. 25, Dec. 19, 1988, pp. 2886-2889.

Costagliola, Ciro et al., "ArF 193 nm Excimer Laser Corneal Surgery as a Possible Risk Factor in Cataractogenesis", *Exp. Eye Res.*, 1994, vol. 58, pp. 453-457.

Cotlier, Edward, M.D., "The Lens", *Adler's Physiology of the Eye*, copyright 2003, pp. 268-290.

Crawford, Kathryn S. et al., "The Role of the Iris in Accommodation of Rhesus Monkeys", *Investigative Ophthalmology & Visual Science*, vol. 31, No. 10, Oct. 1990, pp. 2185-2190.

Croft, Mary Ann et al., "Accommodation and Presbyopia", publisher unknown, vol. 41, 2001, pp. 33-46.

Croft, Mary Ann et al., "Accommodation and Presbyopia: The Ciliary Neuromuscular View", *Opthalmol Clin N Am*, vol. 19, 2006, pp. 13-24.

Croft, Mary Ann et al., Accommodative Ciliary Body and Lens Function in Rhesus Monkeys, I: Normal Lens, Zonule and Ciliary Process Configuration in the lridectomized Eye, *IOVS*, vol. 47, No. 3, Mar. 2006, pp. 1076-1086.

Croft, Mary Ann et al., "The Zonula, Lens, and Circumlental Space in the Normal Iridectomized Rhesus Monkey Eye", *IOVS*, vol. 47, No. 3, Mar. 2006, pp. 1087-1095.

Cromie, William J., "Laser Makes History's Fastest Holes", *The Harvard University Gazette*, 1999, obtained at: http://www.news.harvard.edu/gazette/1999/10.07/laser.html, 6 pags.

Czygan, G. et al., "Mechanical testing of isolated senile human eye lens nuclei", *Med. Eng. Phys.*, vol. 18, No. 5, 1996, pp. 345-349.

Datta, Debajyoti, "Tissue Surgery and Subcellular Photodisruption with Femtosecond Laser Pulses", *Thesis for Dept. of Physics, Harvard University*, May 2002, pp. 1-74.

Dausinger, Friedrich et al., "Micro-machining with ultrashort laser pulses: From basic understanding to technical applications", publisher unknown, undated but prior to Jul. 2009, pp. 1-10.

Dholakia, Sheena A. et al., "Prospective evaluation of phacoemulsification in adults younger than 50 years", *J Cataract Refract Surg*, vol. 31, 2005, pp. 1327-1333.

Douven, Lucien F.A. et al., "Characterization of Mechanical Behaviour of Human Skin in Vivo", *Proc. of SPIE*, vol. 3914, 2000, pp. 618-629.

Du, D. et al., "Laser-induced breakdown by impact ionization in $SiO_2$ with pulse widths from 7 ns to 150 fs", *Appl. Phys. Lett.*, vol. 64, No. 23, Jun. 6, 1994, pp. 3071-3073.

Ehrmann, Klaus et al., "Evaluation of porcine crystalline lenses in comparison with molded polymer gel lenses with an improved ex vivo accommodation simulator", *Proc. of SPIE*, vol. 5688, 2005, pp. 240-251.

Ehrmann, Klaus et al., "Ex Vivo Accommodation Simulator II—Concept and Preliminary Results", *Proc. of SPIE*, vol. 5314, 2004, pp. 48-58.

Eisner, Georg, "Eye Surgery—An Introduction to operative technique", Springer-Verlag, Berlin, 1980, pp. 14-19.

El-Osta, Austen A.R. et al., "In vitro model for the study of human posterior capsule opacification", *J Cataract Refract Surg*, vol. 29, 2003, pp. 1593-1600.

Erpelding, Todd N. et al., "Bubble-Based Acoustic Radiation Force for Monitoring Intraocular Lens Elasticity", *IEEE Intl Ultrasonics Symposium*, vol. unknown, 2004, pp. 732-735.

Fagerholm, Per P.P., "The Response of the Lens to Trauma", *Trans. Ophtal. Soc. U. K.*, 1982, vol. 102, p. 369-374.

Farnsworth, P.N. et al., "Anterior Zonular Shifts with Age", *Exp. Eye Res.*, vol. 28, 1979, pp. 291-297.

Findl, Oliver et al., "Laserinterferometric Assessment of Pilocarpine-Induced Movement of an Accommodating Intraocular Lens—A Randomized Trial", *Ophthalmology*, vol. 111, No. 8, Aug. 2004, pp. 1515-1521.

Fisher, R.F. et al., "Changes in lens fibres after damage to the lens capsule", publisher unknown, undated but prior to Jul. 2009, 4 pgs.

Fisher, R.F., "Presbyopia and the Changes With Age in the Human Crystalline Lens", *J. Physiol.*, vol. 228, 1973, pp. 765-779.

Fisher, R. F., "The Ciliary Body in Accommodation", *Trans. Opthalmol. Soc. U.K.*, vol. 105, 1986, pp. 208-219.

Fisher, R.F., "The Force of Contraction of the Human Ciliary Muscle During Accommodation", *J. Physiol.*, vol. 270, 1977, pp. 51-74.

Fisher, R. F. et al., "The elastic constants and ultrastructural organization of a basement membrane (lens capsule)", *Proc. R. Soc. Lond. B.*, vol. 193, 1976, pp. 335-358.

Fisher, R.F., "The Elastic Constants of the Human Lens", *J. Physiol.*, vol. 212, 1971, pp. 147-180.

Fisher, R.F., "Elastic Constants of the Human Lens Capsule", *J. Physiol.*, vol. 201, 1969, pp. 1-19.

Fisher, R. F., "The Mechanics of Accommodation in Relation to Presbyopia", *Eye*, vol. 2, 1988, pp. 646-649.

Fleck, Brian W. et al., "Q-switched Nd:YAG laser disruption of rabbit lens nucleus", *Laser and Light in Ophthalmology*, 1990, vol. 3. No. 3, pp. 227-232.

Foster, C. Stephen et al., "Smolin and Thoft's The Cornea: Scientific Foundations and Clinical Practice", *The New England Journal of Medicine*, vol. 353 No. 23, 2005, pp. 2519- 2520.

Fujimoto, James et al., "Biomedical Optics", Photonics West, *Proc. of SPIE*, vol. unknown, 2005, pp. 23-70.

Garner, LF et al., "Changes in Equivalent and Gradient Refractive Index of the Crystalline Lens with Accommodation", *Optom, Vis. Sci.*, vol. 74, No. 2, Feb. 1997, pp. 114-119.

Garner, LF et al., "Changes in Ocular Dimensions and Refraction with Accommodation", *Ophthal. Physiol. Opt.*, vol. 17, No. 1, 1997, pp. 12-17.

Garner, Margaret H. et al., "Selective oxidation of cysteine and methionine in normal and senile cataractous lenses", *Proc. Natl. Acad. Sci. USA*, vol. 77, No. 3, Mar. 1980, pp. 1274-1277.

Gayen, Tapan K. et al., "Near-infrared laser welding of aortic and skin tissues and microscopic investigation of welding efficacy", *Proc. of SPIE*, vol. 4949, 2003, pp. 182-185.

Gershenzon, A. et al., "Clinical and Epidemiology—New software for lens retro-illumination digital image analysis", *Australian and New Zealand Journal of Ophthalmology*, 1999, vol. 27, pp. 170-172.

Giblin, Frank J. et al., "Nuclear Light Scattering, Disulfide Formation and Membrane Damage in Lenses of Older Guinea Pigs Treated with Hyperbaric Oxygen", *Exp. Eye Res.*, 1995, vol. 60, pp. 219-235.

Gills, James P., "Treating astigmatism at the time of cataract surgery", *Current Opinion in Ophthalmology*, 2002, vol. 13, p. 2-6.

Gimbel, Howard V. et al., "Intrastromal Photorefractive Keratectomy with the Nd:YLF Laser", publisher unknown, vol. 34, Iss. 4, 1994, pp. 139-145.

Glasser, Adrian et al., "Accommodative Changes in Lens Diameter in Rhesus Monkeys", *IOVS*, vol. 47, No. 1, Jan. 2006, pp. 278-286.

Glasser, A. et al., "Biometric, optical and physical changes in the isolated human crystalline lens with age in relation to presbyopia", *Vision Research*, vol. 39, 1999, pp. 1991-2015.

Glasser, Adrian et al., "On modeling the causes of presbyopia", *Vision Research*, vol. 41, 2001, pp. 3083-3087.

Glasser, A. et al., "On the potential causes of presbyopia", *Vision Research*, vol. 39, 1999, pp. 1267-1272.

Glasser, Adrian et al., "Presbyopia and the Optical Changes in the Human Crystalline Lens with Age", *Vision Res.*, vol. 38, No. 2, 1998, pp. 209-229.

Glasser, Adrian et al., "Ultrasound Biomicroscopy of the Aging Rhesus Monkey Ciliary Region", *Optometry and Vision Science*, vol. 78, No. 6, 2001, pp. 417-424.

Goodenough, Daniel A., "Lens gap junctions: a structural hypothesis for nonregulated low-resistance intercellular pathways", *Invest. Ophthalmol. Visual Sci.*, vol. 18, No. 11, Nov. 1979, pp. 1104-1122.

Grace, Jeffery M. et al., "Repetitively Pulsed Ruby Lasers As Light Sources for High-Speed Photography", *Optical Engineering*, vol. 37, No. 8, Aug. 1998, pp. 1-26.

Gwon, Arlene et al., "Focal laser photophacoablation of normal and cataractous lenses in rabbits: Preliminary report", *J Cataract Refract Surg*, vol. 21, May 1995, pp. 282-286.

Habib, Maged S. et al., "Myopic Intrastromal Photorefractive Keratectomy With the Neodymium-Yttrium Lithium Fluoride Picosecond Laser in the Cat Cornea", *Arch Ophthalmol.*, vol. 113, Apr. 1995, pp. 499-505.

Hahn, D.W., "Dynamics of Ablation Plume Particles Generated During Excimer Laser Corneal Ablation", *Lasers in Surgery and Medicine*, vol. 16, 1995, pp. 384-389.

Hamaoui, Marie et al., "Ex-vivo testing of crystalline lens substitutes: a pilot study", *Proc. of SPIE*, vol. 3908, 2000, pp. 123-130.

Hammer, Daniel X. et al., "Dual OCT/SLO Imager with Three-Dimensional Tracker", *Proc. of SPIE*, vol. 5688, 2005, pp. 33-44.

Hammer, Daniel et al., "Shielding Properties of Laser-Induced Breakdown in Water for Pulse Durations From 5 ns to 125 fs", *Applied Optics*, 1997, vol. 36, No. 22, pp. 5630-5640.

Hanson, S.R.A. et al., "The major in vivo modifications of the human water-insoluble lens crystallins are disulfide bonds, deamidation, methionine oxidation and backbone cleavage", *Exp. Eye Res.*, vol. 71, 2000, pp. 195-207.

Hara, Tsutomu, M.D. et al., "Complications associated with endocapsular balloon implantation rabbit eyes", *J Cataract Refract Surg*, vol. 20, Sep. 1994, pp. 507 and 512.

Harding, J. J., "Disulphide Cross-linked Protein of High Molecular Weight in Human Cataractous Lens", *Exp. Eye Res.* (1973), vol. 17, pp. 377-383.

Hartwick, Andrew T. E. et al., "Ephitelial activity of hexokinase and glucose-6-phosphate dehydrogenase in cultured bovine lenses recovering from pharmaceutical-induced optical damage", *Molecular Vision*, vol. 9, 2003, pp. 594-600.

Heisterkamp, Alexander et al., "Nonlinear effects inside corneal tissue after fs-photodisruption", *Proc. of SPIE*, vol. 4433, 2001, pp. 55-60.

Heisterkamp, Alexander et al., "Pulse energy dependence of subcellular dissection by femtosecond laser pulses", *Optics Express*, vol. 13, No. 10, May 2005, pp. 3690-3696.

Hemenger, Richard P. et al., "Change With Age of the Refractive Index Gradient of the Human Ocular Lens", *Investigative Ophthalmology & Visual Science*, Mar. 1995. vol. 36, No. 3. pp. 703-707.

Heys, Karl Robert et al., "Massive increase in the stiffness of the human lens nucleus with age: the basis for presbyopia?", *Molecular Vision*, vol. 10, 2004, pp. 956-963.

Ho, A. et al., "Feasibility of simultaneous correction of ametropia by varying gel refractive index with phaco-ersatz", *Proc. of SPIE*, vol. 4245, 2001, pp. 119-128.

Hoffman, Richard S. et al., "Refractive lens exchange as a refractive surgery modality", Copyright© 2004 Lippincott Williams & Wilkins, pp. 22-28.

Holzer, Mike P. et al., "Corneal flap complications in refractive surgery—Part 1: Development of an experimental animal model", *J Cataract Refract Surg*, vol. 29, Apr. 2003, pp. 795-802.

Holzer, Mike P. et al., "Corneal flap complications in refractive surgery—Part 2: Postoperative treatments of diffuse lamellar keratitis in an experimental animal model", *J Cataract Refract Surg*, vol. 29, Apr. 2003, pp. 803-807.

Horwitz, Joseph, "α-Crystallin can function as a molecular chaperone", *Proc. Natl. Acad. Sci. USA*, vol. 89. Nov. 1992, pp. 10449-10453.

Hu, Tian-Sheng et al., "Reversal of Galactose Cataract with Sorbinil in Rats", *Investigative Ophthalmology & Visual Science*, May 1983, vol. 24, pp. 640-644.

Huber, G. et al., "Room-temperature 2-μm HO:YAG and 3-μm ER:YAG Lasers", *Journal de Physique*, undated but prior to Jul. 2009, 3 pgs.

Hunter, David, "First, Gather the Data", *New England Journal of Medicine*, vol. 354, No. 4, Jan. 26, 2006, pp. 329-331.

Jacques, Paul F. et al., "Long-term vitamin C supplement use and prevalence of early age-related lens opacities", *Am J Clin Nutr*, 1997; 66, pp. 911-916.

Johannesson, Mattias, "Active Range Imaging 2", PhD-Thesis: SIMD architectures for Range and Radar Imaging, *Linkoping Studies in Science and Technology*, Dissertations No. 399, 2005, pp. 1-34.

Jones, C.E. et al., "Refractive index distribution and optical properties of the isolated human lens measured using magnetic resonance imaging (MRI)", *Vision Research*, vol. 45, 2005, pp. 2352-2366.

Juhasz, Tibor, Ph.D. et al., "Dynamics of Shock Waves and Cavitation Bubbles Generated by Picosecond Laser Pulses in Corneal Tissue and Water", *Lasers in Surgery and Medicine*, vol. 15, 1994, pp. 91-98.

Juhasz, T. et al., "Time resolved observations of shock waves and cavitatin bubbles generated by femtosecond laser pulses in corneal tissue and water", *Lasers in Surgery and Med*, vol. 19, 1996, pp. 23-31.

Juhasz, T. et al., "Time-resolved Studies of Plasma-Mediated Surface Ablation of Soft Biological Tissue with Near-Infrared Picosecond Laser Pulses", *SPIE*, vol. 2975, 1997, pp. 271-281.

Klem, D. E. et al., "The Interaction of Intense Femtosecond Laser Pulses with Solid Targets", paper prepared under the auspices of the U.S. Dept. Of Energy for the Short Wavelength V: Physics with Intense Laser Pulses Second Topical Meeting on Mar. 29-31, published Dece,ber 30, 1992, 1993 6 pgs.

Liu, X. et al., "Competition between Ponderomotive abd Thermal Forces in Short-Scale-Length Laser Plasmas", *Physical Review Letters*, vol. 69, No. 13, Sep. 28, 1992, pp. 1935-1938.

Müller, F. et al., "A Comparative Study of Deposition of Thin Films by Laser Induced PVD with Femtosecond and Nanosecond Laser Pulses", *SPIE*, vol. 1858, 1993, pp. 464-474.

Sauteret, C. et al., "Laser designers eye petawatt power", *Laser Focus World*, Oct. 1990, pp. 85-92 with cover page.

Soileau, M. J. et al., "Temporal Dependence of laser-Induced Breakdown in NaCI and SiO2", prepared for Dept. of Physics, North Texas State University, publication date unknown, 19 pgs.

Stuart, B. C. et al., "Laser-Induced Damage in Dielectrics with Nanosecond to Subpicosecond Pulses", *Physical Review Letters*, vol. 74, No. 12, Mar. 20, 1995, pp. 2248-2251.

Wilks, S. C. et al., "Absorption of ultra-Intense Laser Pulses", *Physical Review Letters*, vol. 69, No. 9, Aug. 31, 1992, pp. 1383-1386.

\* cited by examiner

SYSTEM AND METHOD FOR PERFORMING LADAR ASSISTED PROCEDURES ON THE LENS OF AN EYE

This application claims the benefit of priority under 35 U.S.C. §119(e)(1) of U.S. Provisional Application Ser. No. 61/228,506 titled System and Method for Performing a LADAR Assisted Capsulotomy, filed Jul. 24, 2009, the entire contents of which are incorporated herein by reference.

BACKGROUND OF THE INVENTION

The present invention relates to methods and systems for providing a laser to the natural human crystalline lens to address cataracts, opacifications in the lens, clear lens extraction, removal of natural lens material, use of lens replacement materials and combinations of these. The present invention additionally relates to systems and methods that provide predetermined, precise and reproducible laser shot patterns for creating cuts in the structures of the eye in predetermined and precise shapes that are reproducible from patient-to-patient and surgeon-to-surgeon.

In general, presbyopia is the loss of accommodative amplitude. In generally, cataracts are areas of opacification within the crystalline lens which are sufficient to interfere with vision. Other conditions, for which the present invention is directed, include but are not limited to the opacification of the crystalline lens.

Presbyopia most often presents as a near vision deficiency, the inability to read small print, especially in dim lighting after about 40-45 years of age. Presbyopia, or the loss of accommodative amplitude with age, relates to the eyes inability to change the shape of the natural crystalline lens, which allows a person to change focus between far and near, and occurs in essentially 100% of the population over age 45. Accommodative amplitude has been shown to decline with age steadily through the fifth decade of life.

Cataracts, or the condition when the natural crystalline lens becomes opaque and clouds vision, occurs in millions of people per year and are treated effectively with surgical techniques, such as ultrasonic phacoemulsification pioneered by Kelman 40 years ago. Although the techniques have been refined over the years, safety concerns from ocular trauma, especially to the corneal endothelium from the ultrasonic energy required to break up a hardened cataract is undesirable; especially for those with a compromised corneal endothelium, such as those with Fuchs Dystrophy. Moreover, the use of lasers in the treatment of cataracts has a further issue. Cataracts scatter light, including laser light, and thus, can prevent a laser treatment beam from having the desired tissue effect. Moreover, the light scattering effect of cataracts and other opacifications can make optically determining the position and shape of the lens difficult. Accordingly, as provided in detail in this specification herein improvements in the determination of the lens position and shape, as well as, in the delivery of lasers to lens tissues including the lens capsule, cataractous and opacified tissues are provided.

The established treatment for cataracts is the removal of the opacified human crystalline lens and its replacement with an intra ocular lens IOL. In general, IOLs consist of a small plastic lens with plastic side struts, called haptics, to hold the lens in place within the capsular bag inside the eye. Exemplary types of IOLs include monofocal lenses, multifocal IOLs, which provide the patient with multiple-focused vision at far and reading distance, and accommodative IOLs, which provide the patient with visual accommodation. The flexible nature of many IOLs enables them to be rolled and/or folded up for insertion into the capsule. Examples of IOLs are found in U.S. Pat. Nos. 7,188,949, 6,849,091, 5,699,142 and 5,607,472, the entire disclosures of each of which are incorporated herein by reference. Commercially available IOLs that, by way of example, may benefit from the present invention are CRYSTALENS and ACRYSOF RESTOR.

A schematic representation of the shape and general structure of an example of an accommodating IOL, along the lines of a CRYSTALENS, is provided in FIG. 2. This IOL has a lens structure 202, hinges 203 located adjacent to the lens structure 202 and haptics 204, which contact the lens capsule 201. The overall shape of this IOL would be non-geometric. As used herein the term "non-geometric shape" refers to shapes other than circles, ellipses, squares and rectangles. As used herein the term "geometric shape" refers to circles, ellipses, squares and rectangles.

The CRYSTALENS IOL was developed by Eyeonics and is presently provided by Bausch & Lomb. It is at least in part believed to be disclosed in U.S. Pat. No. 6,849,091. Further information regarding its structure and efficacy is provided by the Food and Drug Administration (FDA) PMA P030002 and related documents to that PMA file. The FDA approved indicated use for CRYSTALENS was in part: "The Crystalens™ Model AT-45 Accommodating IOL is intended for primary implantation in the capsular bag of the eye for visual correction of aphakia in adult patients in whom a cataractous lens has been removed and is intended to provide near, intermediate, and distance vision without spectacles. The Crystalens™ IOL provides approximately one diopter of monocular accommodation." (Nov. 14, 2003 PMA P030002 at Part 2, Summary of Safety and Effectiveness Data, ¶ INDICATIONS FOR USE).

Thus, the CRYSTALENS is an example of an FDA approved accommodating IOL. The term "FDA approved accommodating IOL" refers to any IOL that has obtained FDA approval having an indicated use that provides for accommodation, regardless whether such IOL is actually being employed for such an approved use.

The ACRYSOF RESTOR IOL is provided by Alcon and is at least in part believed to be disclosed in U.S. Pat. No. 5,669,142. Further information regarding its structure and efficacy is provided by FDA PMA P040020 and related documents to that PMA file. The FDA approved use for RESTOR was in part: "AcrySOF® ReSTOR®IOLs are indicated for the visual correction of aphakia secondary to removal of a cataractous lens in adult patients with and without presbyopia, who desire near, intermediate and distance vision with increased spectacle independence. The lens is intended to be placed in the capsular bag." (Apr. 24, 2004, PMA P040020, at Part 2, Summary of Safety and Effectiveness Data, ¶ INDICATIONS).

Thus, the RESTOR is an example of an FDA approved IOL for near, intermediate and distance vision. The term "FDA approved IOL for near, intermediate and distance vision" refers to any IOL that has obtained FDA approval having an indicated use that provides for near, intermediate and distance vision, regardless whether such IOL is actually being employed for such an approved use. The CRYSTALENS would also be an example of an FDA approved IOL for near, intermediate and distance vision. Moreover, the RESTOR and CRYSTALENS are examples of an FDA approved IOLs that reduce and/or eliminate the need for spectacles.

Once the initial incision has been made, the removal of the opacified natural crystalline lens and replacement with a lens replacement material, such as an FDA approved IOL, presently employ a capsulorhexis and/or a capsulotomy. A capsulorhexis generally consists of the removal of a part of the anterior lens capsule and the creation of a hole or opening in the lens capsule, that results at least in part from a tearing action. A capsulotomy generally consists of a cutting of the lens capsule, without or with minimum tearing of the capsule. Thus, to remove the opacified natural lens material, the lens capsule is opened. There are several known techniques for performing a capsulorhexis and a capsulotomy.

One of these capsulorhexis techniques is a can opener approach. This approach uses a small bent needle to make small incisions around the anterior lens capsule to create an opening in the lens through which the lens could be removed. This technique quite often results in the opening in the lens capsule having ragged edges. Another of these techniques is a Continuous Curvilinear Capsulorhexis (CCC). CCC uses the same type of bent needle to begin the tear in the anterior lens capsule and then uses this needle and/or special forceps which are guided under the edge of the cut to create the hole in the lens capsule. CCC, in comparison to the can opener approach, reduces the ragged edge around the opening in the lens that occurred with using the can opener technique. However CCC does not eliminate the formation of these ragged edges and their presence is dependent upon surgical skill and technique.

The use of a Fugo plasma blade to create the hole in the anterior capsule may also be used. This technique is referred to as a capsulotomy. The Fugo plasma blade is a hand held device and was originally utilized in dentistry. It is an electro magnetic device that focuses its energy on a blunt cutting filament. Information regarding the Fugo plasma blade can be found in FDA PMA K063468, K001498, K041019, and K050933.

To date is it believed that all prior techniques and apparatus and in particular all prior FDA approved apparatus for creating an opening in the anterior capsule of the lens, have to varying degrees given rise to surgeon-to-surgeon and patient-to-patient irregularities. These irregularities have given rise to slower or less desirable wound healing and results. The prior techniques and apparatus for creating an opening in the anterior capsule of the lens have further and to varying degrees given rise to irregular shapes, ragged edges, jagged edges, or tags in or along the edge of the opening, and/or combinations of these edge features. Moreover, it is believed that all of these prior techniques and apparatus, which are performed by hand, in general can only produce cuts or holes in the shape of a circle or an ellipse, i.e., they can only be used to provide geometric shapes and cannot be used to provide non-geometric shaped cuts. Further, because these are hand held devices the shape of these cuts varies from patient-to-patient and surgeon-to-surgeon. Thus, it is not believed that these hand held devices and non-automated techniques can provide the precise predetermined capsulotomy of the present invention.

The presence of the above described irregularities can present difficulties and problems. Further the above described edge features, the inability to create precise predetermined and reproducible shaped cuts and the variability associated with prior techniques and apparatus for performing capsulotomies and capsulorhexises are individually and collectively undesirable and can present difficulties and problems, especially with the use of accommodative IOLs. Furthermore, the limited number of shapes for capsulotomies and capsulorhexis and the variability associated with these prior techniques is believed to be an impediment to the development of new accommodative IOLs. It is further believed that this limited number of shapes and variability is an impediment to the amount of accommodation that can be obtained from presently known IOLs and the instances where little to no accommodation is realized by the patient.

SUMMARY

It is desirable to develop systems that would reduce or eliminate these undesirable edge features, provide greater control in the creation of the incisions and to make these improvements patient and surgeon independent, or at least, reduce the variability from patient-to-patient and surgeon-to-surgeon, associated with the formation of these undesirable features that is found with the use of present techniques and tools. The novel and improved methods and systems for the performance of incisions in the natural crystalline human lens, also at times referred to herein as the lens, the natural lens, the human lens, and the crystalline lens, which include aspects of the present inventions and which are set forth in detail in the present patent specification, may provide for better implementation of other methods and systems for delivering laser beams to the lens of the eye, such as those disclosed in published patent applications US 2007/173794A1, US 2007/173795A1, US 2007/185475A1, WO 2007/084694 A2 (now U.S. Ser. No. 12/217,295), and WO 2007/084627A2 (now U.S. Ser. No. 12/217,285) the entire disclosure of each of which is incorporated herein by reference The present invention, among other things, solves this need by providing greater control in the creation of precise and predetermined capsulotomies, which provides benefits including greater precision in determining the position of the edge of the hole, greater uniformity of the edge of the hole, and by providing improvements in the ability to reduce the occurrence of undesirable edge features, and to do so in a manner that is less surgeon and patient dependent. Thus, there is provided herein a system and method to perform the claimed invention.

Thus, there is provided a system for reducing eye-to-eye and surgeon-to-surgeon variability in performing procedures to create cuts in a capsule of a lens of an eye, the system including: a laser for producing a laser beam; an optical path for directing the laser beam from the laser to the lens of the eye; and, a control system for at least directing the laser beam in a predetermined jigsaw capsulotomy pattern having a plurality of laser shots positioned in the x, y and z directions as they are directed toward the lens of the eye. Moreover, in this system the laser beam may include a first power below LIOB and a second power at or above LIOB, the system may further have the first power used as laser radar to determine the position of the anterior capsule of the lens of the eye and the second power is used to cut the lens capsule, whereby the second power performs the capsulotomy, and still further may have the laser beam shots alternated between a series of shots at the first power and a series of shots at the second power along the predetermined jigsaw capsulotomy pattern and still further may have the majority of the second power shots are placed substantially in the area of the anterior portion of the lens capsule.

There is also provided a system for reducing eye-to-eye and surgeon-to-surgeon variability in performing procedures to create cuts in a capsule of a lens of an eye, the system including: a laser for producing a laser beam; an optical path for directing the laser beam from the laser to the lens of the eye; and, a control system for at least directing the laser beam in a predetermined jigsaw capsulotomy pattern having a plurality of laser shots positioned in the x, y and z directions as they are directed toward the lens of the eye in which the predetermined shot pattern includes a first essentially straight section, a second essentially straight section, a first curved section and a second curved section; and, the first essentially straight section is connected to the second and third curved sections, which may still further have the shape of the predetermined shot pattern is based at least in part on the shape of an IOL, the IOL including a hinge, and the pattern essentially following the shape of the IOL.

There is additionally provided a system for reducing eye-to-eye and surgeon-to-surgeon variability in performing procedures to create cuts in the capsule of the lens of the eye, the system including: a laser for producing a laser beam; an optical path for directing the laser beam from the laser to the lens of the eye; the laser beam having a first power below LIOB and a second power above LIOB; a control system for at least directing the laser beam in a predetermined shaped shot pattern on a portion of the anterior capsule of the lens of the eye to create a precise predetermined non-geometric shaped capsulotomy; and, the shot pattern shape being based at least in part on the shape of an IOL.

There is additionally provided a system for reducing eye-to-eye and surgeon-to-surgeon variability in performing procedures to create cuts in the capsule of the lens of the eye, the system including: a therapeutic laser for producing a therapeutic laser beam; an optical path for directing the therapeutic laser beam from the therapeutic laser to the lens of the eye; a control system for at least directing the laser beam in a predetermined jigsaw capsulotomy patterns having a plurality of laser shots positioned in the x, y and z directions as they are directed toward the lens of the eye; a first pattern positioned in a first area of the anterior capsule of the lens of the eye, the first pattern having a z direction sweep range less than about 15 µm; a second pattern positioned in a second area of the anterior capsule of the lens of the eye, the second are is anterior to the first area, the second pattern having a z direction sweep range of less than about 15 µm.

Moreover there is provided a system for reducing eye-to-eye and surgeon-to-surgeon variability in performing procedures to create cuts in the capsule of the lens of the eye, the system including: a therapeutic laser for producing a therapeutic laser beam; an optical path for directing the therapeutic laser beam from the therapeutic laser to the lens of the eye; a control system for at least directing the laser beam in a predetermined jigsaw capsulotomy patterns having a plurality of laser shots positioned in the x, y and z directions as they are directed toward the lens of the eye; and, the pattern consisting essential of a plurality of single z direction sweeps wherein all the shots in each single z direction sweep overlap in the x y dimensions.

Yet further there is provided a system for reducing eye-to-eye and surgeon-to-surgeon variability in performing procedures to create cuts in the capsule of the lens of the eye, the system including: a therapeutic laser for producing a therapeutic laser beam; an optical path for directing the therapeutic laser beam from the therapeutic laser to the lens of the eye; a control system for at least directing the laser beam in a predetermined jigsaw capsulotomy patterns having a plurality of laser shots positioned in the x, y and z directions as they are directed toward the lens of the eye; and, the pattern including a plurality of single z direction sweeps, each single direction z direction sweep consisting essential of shots that overlap in the x-y dimensions.

Still further there is provided a system for reducing eye-to-eye and surgeon-to-surgeon variability in performing procedures to create cuts in the capsule of the lens of the eye, the system including: a therapeutic laser for producing a therapeutic laser beam; an optical path for directing the therapeutic laser beam from the therapeutic laser to the lens of the eye; a control system for at least directing the laser beam in a predetermined jigsaw capsulotomy patterns having a plurality of laser shots positioned in the x, y and z directions as they are directed toward the lens of the eye; and, the pattern including a plurality of single z direction sweeps wherein the shots in a single z direction sweep overlap in the x-y dimensions.

These forgoing systems may further have: the predetermined shot pattern includes at least one essentially straight section; the predetermined shot pattern includes at least two essentially straight sections; the predetermined shot pattern has a first essentially straight section, a second essentially straight section, a first curved section and a second curved section or the predetermined shot pattern includes a first essentially straight section, a second essentially straight section, a first curved section and a second curved section; and, the first essentially straight section is connected to the second and third curved sections; the predetermined shot pattern is a jigsaw pattern; the IOL is an FDA approved accommodating IOL; the IOL is an FDA approved IOL for near, intermediate and distance vision; the IOL is an FDA approved IOL that reduces or eliminates the need for spectacles; the shot patterns shape is based at least in part on the shape of an IOL, the IOL having at least one hinge, and, the shot patterns essentially following the shape of the IOL; the z direction sweep range less than about 10 µm; and/or the z direction sweep range less than about 5 µm.

One of ordinary skill in the art will recognize, based on the teachings set forth in these specifications and drawings, that there are various embodiments and implementations of these teachings to practice the present invention. Accordingly, the embodiments in this summary are not meant to limit these teachings in any way.

DESCRIPTION OF THE DRAWINGS AND THE PREFERRED EMBODIMENTS

In general, the present inventions relates to methods and systems for providing a laser to the natural human crystalline lens to address cataracts, opacifications in the lens, clear lens extraction, removal of natural lens material, replacement of that material with replacement material, and combinations of these. The present invention further relates to systems and techniques to provide other cuts to the structures of the eye, which cuts are associated with the removal and replacement of natural lens material and subsequent treatment of the eye and which systems and methods are disclosed in part in applications, which are incorporated in this specification by reference.

The present methods and systems can be used with the novel and innovative laser system techniques that are the subject of the co-pending patent applications that are cited herein and which have been incorporated herein by reference, and the present methods and systems may possibly be used with other laser delivery systems for the removal of lens material to the extent such systems may be developed in the future. Preferably, the present methods and systems can be incorporated into and used in conjunction with the systems of the co-pending applications that have been incorporated herein by reference. In this way a single system, with a single therapeutic laser, can function as a start to finish device for performing the cuts necessary to remove and replace the natural lens.

Novel and pioneering laser systems and methods for the removal and replace of lens material are disclosed in U.S. provisional and regular applications: Ser. No. 61/228,560, System and Method for Providing Laser Shot Patterns to the Lens of an Eye; Ser. No. 61/228,484, System and Method for Performing and Sealing Limbal Area Incisions in the Eye filed on Jul. 25, 2009; and, Ser. No. 61/228,514, System and Method for Performing Corrective Arcuate Incisions in the Eye; Ser. No. 12/509,412, Method and System for Removal and Replacement of Lens Material from the Lens of an Eye; and, Ser. No. 12/509,211, Method and System for Creating a Bubble Shield for Laser Lens Procedures, which were filed on Jul. 24, 2009, the entire disclosure of each of which is incorporated herein by reference.

Figure 1:
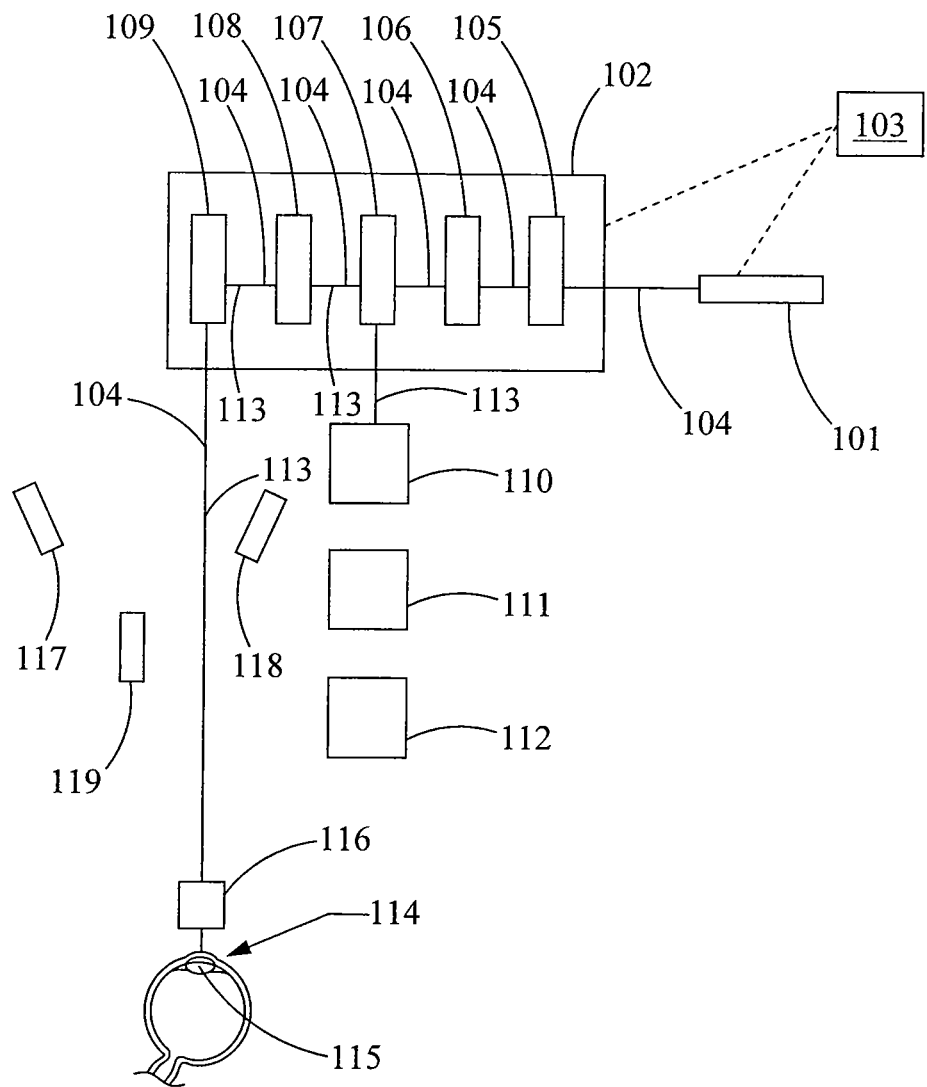
FIG. 1 is a schematic diagram of a type of system for delivering a laser beam shot pattern, such as the shot patterns of FIGS. 3-7 and 12, to the lens of an eye and for performing cuts in capsulotomy, such as shown in FIGS. 8-11.

Thus, in general a laser system, i.e., a laser device, for treating patients is provided as shown by way of example in FIG. 1. In this system there is provided a treatment laser 101; optics 102 for delivering the laser beam 104; a control system for delivering the laser beam to the lens in a particular pattern, which control system 103 is associated with and/or interfaces with the other components of the system, as shown for example by dashed lines in FIG. 1, and/or other control systems not shown in FIG. 1.

In general, the treatment laser 101 should provide a beam 104 that is of a wavelength that transmits through the cornea, aqueous and lens. The beam should be of a short pulse width, together with the energy and beam size, to produce photodisruption. Thus, as used herein, the term laser shot or shot refers to a laser beam pulse delivered to a location that results in photodisruption. As used herein, the term photodisruption essentially refers to the creation of a microscopic shock wave at laser beam focus and conversion of matter to a gas by the laser. The term photodisruption has also been generally associated with Laser Induced Optical Breakdown (LIOB). In particular, wavelengths of about 300 nm to 2500 nm may be employed. Pulse widths from about 1 femtosecond to 100 picoseconds may be employed. Energies from about a 1 nanojoule to 1 millijoule may be employed. The pulse rate (also referred to as pulse repetition frequency (PRF) and pulses per second measured in Hertz) may be from about 1 KHz to several GHz. Generally, lower pulse rates correspond to higher pulse energy in commercial laser devices. A wide variety of laser types may be used to cause photodisruption of ocular tissues, dependent upon pulse width and energy density. Thus, examples of such lasers are disclosed in U.S. Patent Application Publication No. 2007/084694 A2 and WO 2007/084627A2, the entire contents of each of which are incorporated herein by reference. These and other similar lasers may be used a therapeutic lasers.

In general, the optics 102 for delivering the laser beam 104 to the structures of the eye including the natural lens of the eye should be capable of providing a series of shots to the natural lens in a precise and predetermined pattern in the x, y and z dimensions. The z dimension as used herein refers to that dimension which has an axis that corresponds to, or is essentially parallel with the optical (AP) axis of the eye. The optics should also provide a predetermined beam spot size to cause photodisruption with the laser energy reaching the natural lens.

In general, the control system 103 for delivering the laser beam 104 may be any computer, controller, and/or software hardware combination that is capable of selecting and controlling x-y-z scanning parameters and laser firing. These components may typically be associated at least in part with circuit boards that interface to the x-y scanner, the z focusing device and/or the laser. The control system may also, but does not necessarily, have the further capabilities of controlling the other components of the system, as well as, maintaining data, obtaining data and performing calculations. Thus, the control system may contain the programs that direct the laser through one or more laser shot patterns. Similarly, the control system may be capable of processing data from the biometric slit scanned laser and/or from a separate controller for the slit scanned laser system. The slit scanned laser system is a system used to measure the position of optical surfaces within the eye, such as the anterior and posterior lens and corneal surfaces or other eye features such as crystalline lens cataracts. Such measurements are used by the control system to generate patterns of laser shots to perform the desired crystalline lens incisions.

The laser optics 102 for delivering the laser beam 104 includes a beam expander telescope 105, a z focus mechanism 106, a beam combiner 107, an x-y scanner 108, and focusing optics 109. There is further provided relay optics 110, camera optics 111, which include a zoom, and a first ccd camera 112.

Optical images 113 of the eye 114 and in particular optical images of the natural lens 115 of the eye 114 are conveyed along a path 113. This path 113 follows the same path as the laser beam 104 from the natural lens 115 through the laser patient interface 116, the focusing optics 109, the x-y scanner 108 and the beam combiner 107. There is further provided a laser patient interface 116, and a structured light source 117 and a structured light camera 118, including a lens. Examples of patient interface and related apparatus that are useful with the present system are provided in application Ser. No. 12/509,021, Liquid Filled Index Matching Device for Ophthalmic Laser Procedures, Ser. No. 61/228,457, Liquid Holding Interface Device for Ophthalmic Laser Procedures, filed Jul. 24, 2009, and U.S. patent application Ser. No. 12/840,818, filed on Jul. 21, 2010, the entire disclosures of each of which is incorporated herein by reference.

A structured light source 117 may be a slit illumination having focusing and structured light projection optics, such as a Schafter+Kirchhoff Laser Macro Line Generator Model 13LTM+90CM, (Type 13LTM-250S-41+90CM-M60-780-5-Y03-C-6) or a StockerYale Model SNF-501 L-660-20-5, which is also referred to as a slit scanned laser. In this embodiment the structured illumination source 117 also includes slit scanning means 119.

When using a scanned slit illumination the operation includes positioning the slit on one side of the lens, taking an image then moving the slit approximately one slit width, then taking another image, and then repeating this sequence until the entire lens is observed. For example, a 100 µm slit width can scan a nominal 9 mm dilated pupil diameter in 90 images, which takes approximately 3 seconds using a 30 Hz frame rate camera. To obtain images of the anterior surface in a single image without overlap, the slit should be at an angle to the axis of the structured light camera 118, i.e., it should not be parallel to that axis. The nominal slit angle can be approximately 30-60 degrees from the structured light camera axis. Any visible or near IR wavelength source within the sensitivity of the camera may be used. Low coherence length sources are preferable to reduce speckle noise in the structured camera image.

The structured light illumination source 117 and the structured light camera 118 are arranged in an angled relationship. The angled relationship, which may include angling the detector of the structure light camera with respect to the axis of the camera optics, may be but is not required to be in the so-called Scheimpflug configuration, which is well-known. The structured light source 117, in conjunction with the slit scanning means 119, projects a line and or a plurality of lines onto the cornea and crystalline lens 115 at an angle or plurality of angles. The light scattered from these objects is focused by the lens 115 and focused onto the camera system 118. Since the slit illuminated image of the cornea and lens 115 may be at a large angle with respect to the camera 118, this presents a large depth of field to the camera and the entire slit image may not be in sharp focus at the camera. By tilting the camera at an angle or plurality of angles the image along the illuminated plane can be in sharper focus. To the extent that a sharp focus is not obtained, arithmetic data evaluation means are further provided herein to determine a more precise location of the illuminated structures with respect to the laser device.

Alternatively, the structured light illumination source may be a focused beam whose point of focus is scanned throughout the regions of interest within the eye. The scanned path of the beam might simulate the area illuminated by the scanned slit illumination described above by executing a raster scan of a plane of the eye analogous to that illuminated by the slit laser. In this context, raster scan refers to a process in which the beam focus is scanned, row-by-row, to illuminate a section of the eye. In this case, the camera's detector would be exposed to the scattered light from the scanned beam for the whole duration of the raster scan.

The images from the camera 118 may be conveyed to the controller 103 for processing and further use in the operation of the system. They may also be sent to a separate processor and/or controller, which in turn communicates with the controller 103. The structured light source 117, the camera 118 and the slit scanning means 119 include a means for determining the position of the crystalline lens and corneal surfaces in relation to the laser system and thus include a means for determining the position and apex of the lens in relation to the laser system.

In general, the present invention provides for the delivery of the laser beam in patterns that utilize, or are based at least in part on, lens geometry, curvature of the lens and/or the position and location of the lens with respect various apparatus. As part of the present invention the concept of matching and/or compensating for the curvature and position of the capsule of the lens is provided. Anterior and posterior curvatures can be based on Kuszak aged lens models, Burd's numeric modeling, Burd et al. Vision Research 42 (2002) 2235-2251, or on specific lens measurements. Thus, in general, these laser delivery patterns are based in whole and/or in part on the mathematical modeling and actual observation data regarding the shape of the lens, the position of the lens and/or the geometry of the lens.

The delivery of laser shot patterns for the removal of lens material is provided. Thus, there are provided novel methods and systems for producing cuts, i.e., incisions in the anterior lens capsule. These cuts are created by the therapeutic laser beam 104 being delivered to the anterior lens capsule in precise predetermined and highly reproducible patterns, delivery results in precise predetermined and highly reproducible shaped cuts in patterns as described and taught herein, or as may be called for by the use of a particular IOL or other device or material to be inserted within the lens capsule. As used herein, geometric shaped patterns or cuts refer to circular and elliptical shaped patterns or cuts. As used herein, non-geometric shaped patterns or cuts refer to all other shapes that are not circular or elliptical.

The methods and systems to create these cuts in the anterior capsule provide superior results to the handheld methods and apparatus previously known for performing capsulorhexus and capsulotomy, and thus, the methods and systems disclosed herein are considered to be a substantial advancement in these techniques. In addition the delivery of the laser beam shots in a manner that greatly reduces the risk of a missed cut, which depending upon the particular application may be very significant is provided. Moreover, as provided in the following examples, anterior capsule cuts are envisioned and provided that may be a continuous cuts, cuts and lands (uncut capsule portions between cuts) and perforations. Thus, as used herein the terms "missed cut" or "missed cuts" refer to a cut that was intended to be carried out by the delivery of a particular laser shot pattern, but which did not occur because the laser beam missed the lens capsule or targeted lens material or the targeted material was hit but not cut. Thus, in a cut and land pattern the lands would not be considered missed cuts, if they were intended to be left uncut by the laser pattern.

The cuts in the lens anterior surface are for the purpose of creating an opening in the lens capsule for the remove of the interior structures of the lens. To facilitate this removal there are provided various laser shot patterns that cut the interior structure of the lens into small volumes, which volumes can then be removed from the lens capsule. These small volumes can range from about 1 mm$^3$ to about 16 mm$^3$ and more preferably from about 2.5 mm$^3$ to about 4 mm$^3$. Thus a grid laser shot pattern within the interior structures of the lens, which creates cube shaped volumes of interior lens material, can be employed. These cubes can range in size from a side having a length of about 100 µm to about 3 mm, to about 4 mm, with about 500 µm to 2 mm being a preferred size. An ideal size for the volumetric shapes is one in which the dimensions of the volumetric shape roughly match the size of the opening at the distal end of the aspiration tube. This enables the individual volumetric shape pieces to be easily aspirated into the aspiration tube without or with minimal use of ultrasound energy. Volumetric shape pieces that are substantially smaller than the opening in the aspiration tube require more laser shots without added significant benefit. Additionally, this invention is not limited to the formation of cubes and other volumetric shapes of similar general size may be employed. For example arrangement of other shapes such as triangles and pie sliced volumes may be employed.

The laser cut in the anterior capsule is used to create a small opening in the lens anterior surface of the lens capsule for removal of the sectioned volumes of interior material. Thus, this procedure may be used to treat cataracts. This procedure may also be used to remove a lens having opacification that has not progressed to the point of being cataractous. This procedure may further be used to remove a natural lens that is clear, but which has lost its ability to accommodate. In all of the above scenarios, it being understood that upon removal of the lens material the lens capsule would subsequently house a suitable replacement, such as an IOL, accommodative IOL, or synthetic lens refilling materials. Moreover, the size and the shape of the opening is variable and precisely controlled and preferably for presently know lens refilling materials and IOLs is 2 mm or less diameter for lens refilling applications and about 5 mm for IOLs.

The order in which these activities are performed may depend upon the particular characteristics of the internal lens structure, the density of the cataract, the position of the cataract, the type of device used to remove the internal lens material once it has been sectioned into small volumes, the type and power of the laser used, the amount and size of gas bubbles that are produced by the laser, and other factors. Thus, although the examples herein provide for an order of performing the activity of cutting the anterior surface of the lens and sectioning the interior structures of the lens, it should be recognized that this order can be changed, as well as, performed essentially simultaneously or simultaneously.

The laser system for treating patients of the present invention is capable of making precise and predetermined cuts in the capsule of the lens thus giving rise to capsulotomies that are of precise and predetermined shapes. Thus, there is provided the method of obtaining and analyzing the shape and structure of an IOL, and in particular obtaining and analyzing the shape and structure of an accommodating IOL, an IOL that reduces and/or eliminates the need for spectacles, and/or an IOL for near, intermediate and distance vision, including but limited to FDA approved versions of said IOLs. Based upon this analysis an optimized shape and position for the capsulotomy for use with a particular IOL, or grouping of similarly shaped IOLs, is determined. A predetermined shot pattern for making this optimized shaped capsulotomy is then provided to the laser system, preferably by providing the shot pattern to the control system 103. The laser system can then be used for an one or all of the following procedures, determining the shape and position of the anterior surface of the lens, and in particular the anterior surface of the lens capsule, determining the apex of the lens capsule in relation to the laser system, performing a laser capsulotomy having the precise and predetermined shape selected for a particular type of IOL, and removal of the natural lens material.

Figure 3:
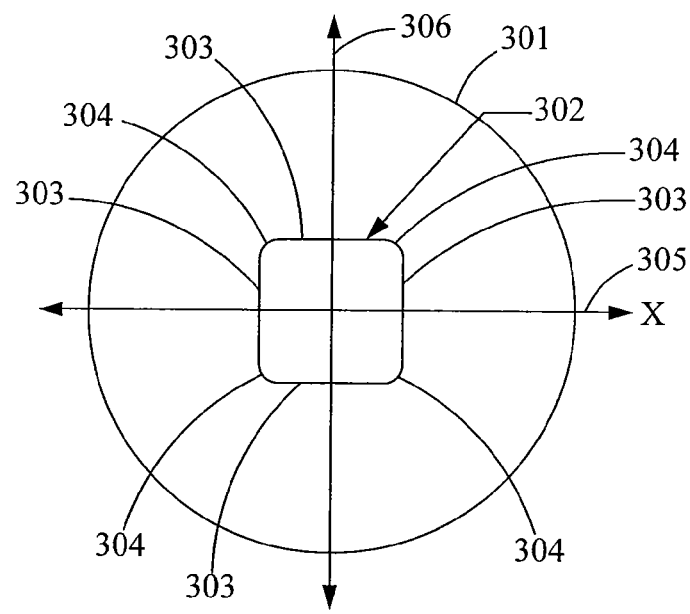
FIGS. 3 and 4 are diagrams of shot patterns.

Thus, for example, the shape of a precise capsulotomy and its corresponding shot pattern may consist of essentially straight sides, which each side being connected by curved or rounded sections. An example of this type of predetermined cut is illustrated in FIG. 3. Thus, there is provided in FIG. 3 a lens capsule 301, which x and y axis 305 and 306 respectively, shown in this figure for reference purposes. There is further illustrated a predetermined shot pattern 302 having essentially straight sections 303, which are connected by curved sections 304. The shot pattern of FIG. 3 would be an example of a non-geometric shaped pattern as that term is used herein. This shot pattern when implemented by the laser system provides a precise predetermined cut in the lens capsule, a precise predetermined opening in the lens capsule and a precise predetermined capsulotomy of the shape illustrated in this figure. The essentially straight sections of the predetermined shot pattern may be from about 0.25 mm to about 4.5 mm. As used herein, any section of an opening, capsulotomy, cut or shot pattern that is essentially straight for a length of more that 0.2 mm is considered to be an essentially straight section of a cut or pattern.

Figure 4:
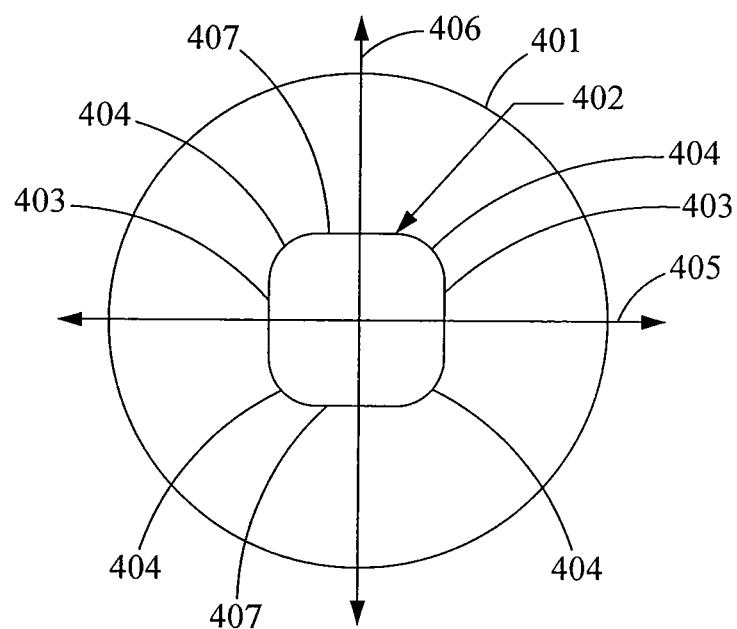

The precise and predetermined shot pattern, opening, capsulotomy and cut may have only a single straight section or it may have two, three, four, five, or more. Moreover, in addition to essentially straight sections, there may be sections in which the radius of curvature is substantially reduced in comparison to other section of the pattern, opening, capsulotomy or cut. Thus, for example, as shown in FIG. 4 there is provided a lens capsule 401, which x and y axis 405 and 406 respectively, shown in this figure for reference purposes. There is further illustrated a predetermined shot pattern 402, which when implemented by the laser system will create a precise predetermined cut, i.e., capsulotomy, having two essentially straight sections 403, four curved sections 404 and two section having a substantially increased radius of curvature 407. Accordingly, each essentially straight section 403 is connected to a substantially increased radius of curvature section 407 by a curved section 404.

Figure 2:
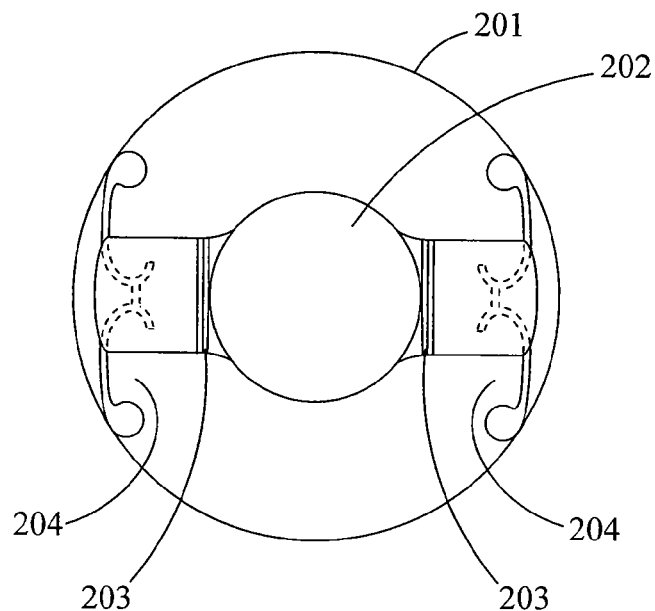
FIG. 2 is a diagram of an accommodating IOL.
Figure 5:
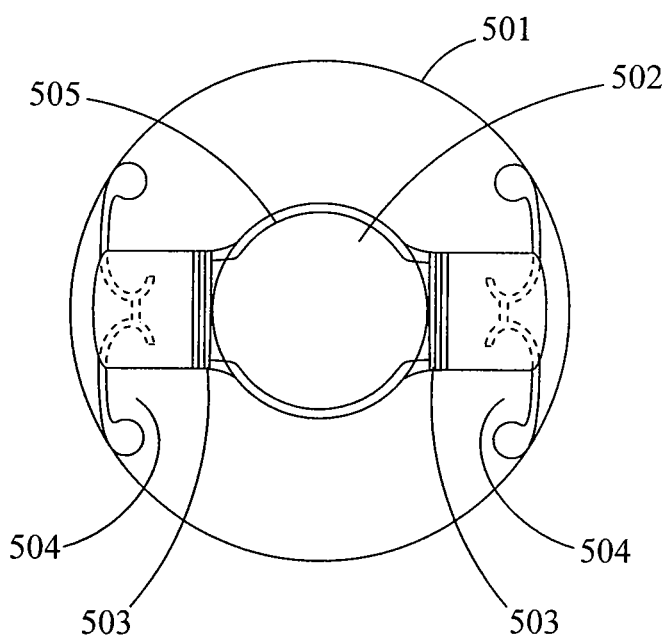
FIG. 5 is a diagram showing the shot pattern of FIG. 4 positioned on the lens of the eye in relation to the accommodating IOL of FIG. 2.

FIG. 5 illustrates a precise predetermine non-geometric cut that can be created by implementing the predetermined shot pattern in relation to the type of IOL shown in FIG. 2. Thus, there is provided an IOL lens structure 502, hinges 503 located adjacent to the lens structure 502, and haptics 504, which contact the lens capsule 501. There is further provided a precise predetermined non-geometric capsulotomy 505, having two curved section and two essentially straight sections. The positioning of these sections is further illustrated in FIG. 5, with the essentially straight sections being positioned inside of the hinges, i.e., toward the lens structure. This cut and pattern would be an example of a cut, opening, capsulotomy and pattern that essentially follow the shape of an IOL, this cut has been referred to as an ALL-ON cut, because it leaves lens capsule material that is on all of the IOL.

Figure 6:
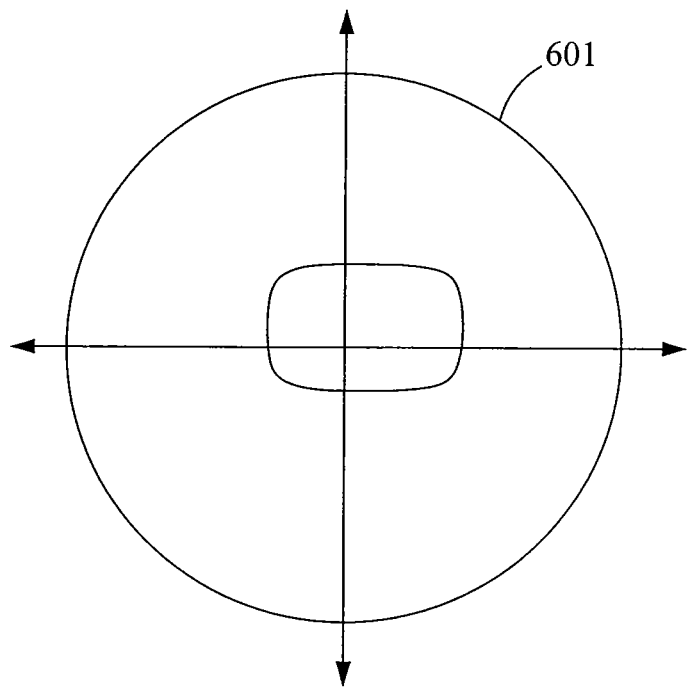
FIG. 6 is a diagram of a shot pattern.

FIG. 6 is an illustrative example showing that the pattern and cut can be move off center with respect to the capsule 601.

Thus, there is provided techniques, systems and apparatus to deliver laser beam in a shot pattern to the lens of the eye and in particular to the capsule of the lens of the eye in a precise and predetermined manner to provided for a precise predetermined capsulotomy. The shape of these patterns may be delivered using either the jigsaw or ring delivery sequences provided herein.

When performing laser assisted cataract surgery the process of cutting the nucleus with a photodisruption laser can cause a buildup of gas bubbles sufficiently near the soft cortex to allow the gas bubbles to propagate toward the capsule. In those situations where bubbles collect in close proximity to the anterior capsule, when the laser attempts to cut the capsulotomy, the sudden release of bubbles my change the position of the anterior capsule during the delivery of the laser shot pattern causing the laser to miss the capsule resulting in missed cuts, at least partially around the circumference of the capsulotomy. To solve this problem, there is provided herein a special cutting pattern that is less dependent of capsule position versus time and provides cutting of the capsule despite position changes of the capsule during the laser capsulotomy procedure. Thus, resulting in substantially reduced or no missed cuts.

There is provided herein the use of laser shot patterns having a large range of Z swept at a high rate of speed, while the X-Y position is moved in a circular, or elliptical or other pattern or desired shape, more slowly so that the laser cutting action occurs multiple times over essentially the same X-Y position. Thus, it could be envisioned that the laser beam is operating like the tip of a jigsaw blade moving up and down rapidly compared to the X-Y positioning to create the cut shape. In this way, if the anterior capsule shifts during the cut, due to gas bubble propagation or any other reason, the cut will still be made to the capsule, albeit perhaps outside the center region of the z direction up-down distribution of shots, and more to the anterior or posterior ends of that distribution. For laser cutting of the nucleus where a great deal of bubble buildup is created, a Z range, or up-down range of the cut should be approximately 1 mm in extent, nominally centered on the anterior capsule which would allow approximately +/−475 µm of capsule movement and still provide cutting of a 25 µm thick capsule.

In addition to enabling cutting of a capsule that moves move during the procedure, this procedure can be used to compensate for static errors in capsule position due to for example measurement errors. In this way the extent of the Z range may be increased by the known error of the system.

In addition to the large Z range sweeps disclosed herein, there is also contemplated the use of a smaller Z range of cut motion for the case where the uncertainty in capsule position from both static measurement error and anticipated change in position might be smaller, perhaps in the range of hundreds of µm or in the case of highly precise measurement data and near zero movement of the capsule during surgery. In such a case the Z range could be tens of µm—enough range to cut through the capsule thickness.

The Z range sweep in the capsulotomy shot pattern provides for the ability to optimize laser surgery efficiency in cataract removal procedures. Thus, the nucleus of the lens can be sectioned into small volumes before the capsulotomy is performed. In this way any gas bubbles that are formed by the sectioning of the nucleus will be trapped within the capsule. By keeping the gas bubbles inside of the capsule, their effect on laser delivery is reduced, when compared to their effect if they escape from the capsule and migrate into the aqueous or collect and build up next to the posterior of the cornea. The detrimental effect of shooting the laser beam through a bubble increases as the distance that the beam has to travel after passing through the bubble before reaching its intended point increases. Thus, by trapping the bubble in the capsule this distance is keep to an absolute minimum and thus the detrimental effect of shooting through the bubbles is similarly minimized.

The accumulation of bubbles within the capsule, however, increases the likelihood that the lens and/or capsule will shift during the capsulotomy as the bubbles escape through the cuts in the lens capsule. As noted above this shifting could result in missed cuts and an incomplete capsulotomy. Thus, the Z range sweep avoids any missed cuts from lens or capsule movement and accordingly provides the synergistic advantages of increased laser efficiency, reduced detrimental effect of gas bubbles, and reduced missed cuts in the capsulotomy.

Thus, there is provided a system and method to optimize laser surgery efficiency in an embodiment of the present invention by allowing the nucleus to be cut first, and the gas bubbles formed from such cutting contained within the capsule, until the capsulotomy is performed. The containing of the gas bubbles within the capsule avoids having to shoot through bubbles in the anterior chamber caused but creating the capsulotomy first. This solution, however, can lead to the accumulation of bubbles inside the fibrous mass of the lens, which may cause the capsule to move during capsulotomy. To address this potential movement the invention further provides for the varying z direction movement of the laser beam. However, it is also understood that, one case where the uncertainty of capsule movement is small is the case where the capsulotomy is laser cut prior to the cutting of the nucleus material and no bubbles have been placed in the lens. In this case if the uncertainty in position is sufficiently small that the extent of the z range is sufficiently small, so that only a superficial amount of bubbles may be present in the anterior chamber which may not interfere with laser cutting of the nucleus. It should further be understood that when referring to a sequence of cutting structures, such as described in this paragraph, that the sequence is meet when a substantial majority of the cuts are performed in the one structure before another structure, i.e., the placement of a few laser shots in an other structures during delivery of the shot pattern to the first structure will not prevent the first structure from being considered the first structure in the sequence.

Further methods and systems to define a high accuracy position measurement of structures of the eye and in particular the anterior capsule, so as to provide in general greater accuracy, precisions and reproducibility from patient-to-patient for procedures on the eye and in particular capsulotomies, is provided in U.S. patent application Ser. No. 12/509,412 (Method and System for Removal and Replacement of Lens Material from the Lens of an Eye) filed on Jul. 24, 2009, the entire disclosure of which is incorporated herein by reference.

A further optimization of the method and system to enhance flexibility regarding the aspiration of lens material from the lens capsule is provided. In sectioning the lens material it is possible that the some of the cut fragments of the fibrous mass may escape the capsular bag, either by floating or because of gas bubbles or just naturally, unless means of preventing such escape are provided. Therefore another aspect of the present method and system is to provide a means to restrain these fragments until they are ready to be aspirated out. Such a means is provided by performing only a partial cut of the capsule, leaving the capsule flap attached to serve as a restraint preventing and/or reducing the escape of sectioned lens material. Once aspiration is called for the partial cut to the capsule can be completed, i.e., the capsulotomy is completed, and the section lens material aspirated out of the lens capsule.

In all of the laser shot patterns provided herein it is preferred that the laser shot patterns generally follow the shape of the lens and placement of individual shots with respect to adjacent shots in the pattern are sufficiently close enough to each other, such that when the pattern is complete a sufficiently continuous layer and/or line and/or volume of lens material has been removed. Shot spacing of lesser or greater distances are contemplated herein and including overlap as necessary to obtain the desired results. Shot spacing considerations include gas bubble dissipation, volume removal efficiency, sequencing efficiency, scanner performance, and cleaving efficiency among others. For example, by way of illustration, for a 5 µm size spot with an energy sufficient to cause photodisruption, a spacing of 20 µm or greater results in individual gas bubbles, which are not coalesced and dissipate more quickly, than with close shot spaces with the same energy, which result in gas bubble coalescence. As the shot spacing gets closer together volume efficiency increases. As shot spacing gets closer together bubble coalescence also increases. Further, there comes a point where the shot spacing becomes so close that volume efficiency dramatically decreases. For example, by way of illustration, for a 450 femtosecond pulse width and 2 microjoules energy and about a 5 µm spot size with a 10 µm separation results in cleaving of transparent ocular tissue. As used herein, the term cleaving means to substantially separate the tissue. Moreover, the foregoing shot spacing considerations are interrelated to a lesser or greater extent and one of skill in the art will know how to evaluate these conditions based upon the teachings of the present disclosure to accomplish the objectives herein. Finally, it is contemplated that the placement of individual shots with respect to adjacent shots in the pattern may in general be such that they are as close as possible, typically limited by the size and time frame of photodisruption physics, which would include among other things gas bubble expansion of the previous shot. As used herein, the time frame of photodisruptive physics refers to the effects that take place surrounding photodisruption, such as plasma formation and expansion, shock waive propagation, and gas bubble expansion and contraction. Thus, the timing of sequential pulses such that they are timed faster than some of, elements of, or all of those effects, can increase volumetric removal and/or cleaving efficiency. Accordingly, we propose using pulse repetition frequencies from 50 MHz to 5 GHz, which could be accomplished by a laser with the following parameters: a mode lock laser of cavity length from 3 meters to 3 cm. Such high PRF lasers can more easily produce multiple pulses overlapping a location allowing for a lower energy per pulse to achieve photodisruption.

The terms first, second, third, etc. as used herein are relative terms and must be viewed in the context in which they are used. They do not relate to timing, unless specifically referred to as such. Thus, a first cut may be made after a second cut. In general, it is preferred to fire laser shots in general from posterior points in the laser pattern to anterior points, to avoid and/or minimize the effect of the gas bubbles resulting from prior laser shots. However, because of the varied laser shot patterns that are provided herein, it is not a requirement that a strict posterior to anterior shot sequence be followed. Moreover, in the case of cataracts it may be advantageous to shoot from anterior to posterior, because of the inability of the laser to penetrate substantially beyond the cataract.

Thus, there is provided a method for the structural modification of the lens material to make it easier to remove while potentially increasing the safety of the procedure by reducing and/or eliminating the need to use high frequency ultrasonic energy used in Phaco emulsification. In general, the use of photodissruption cutting in a specific shape patterns is utilized to create sectioned lens material, i.e., to carve up the lens material into sectioned volumetric shapes, such as the tiny cube like structures shown in FIG. 7, which are small enough to be aspirated away with 1 to 2 mm sized aspiration needles.

Figure 7:
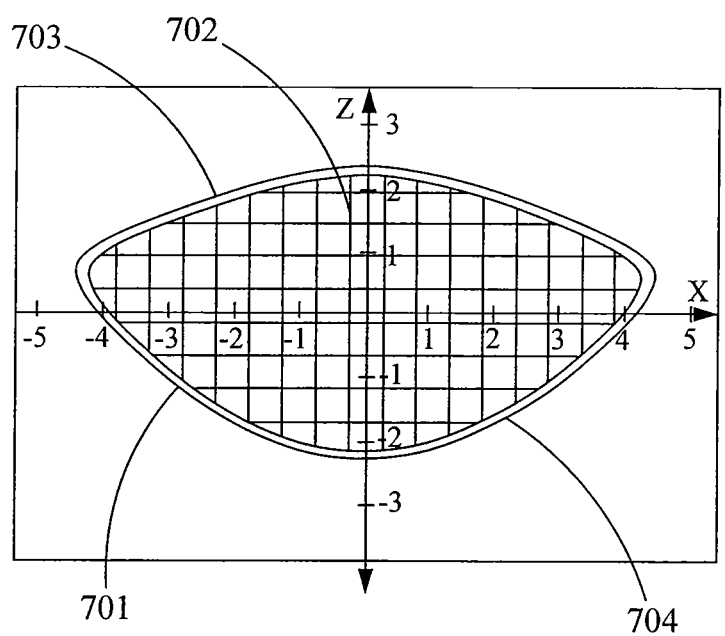
FIG. 7 is a diagram showing a shot pattern for the sectioning and removal of lens material.
Figure 8A:
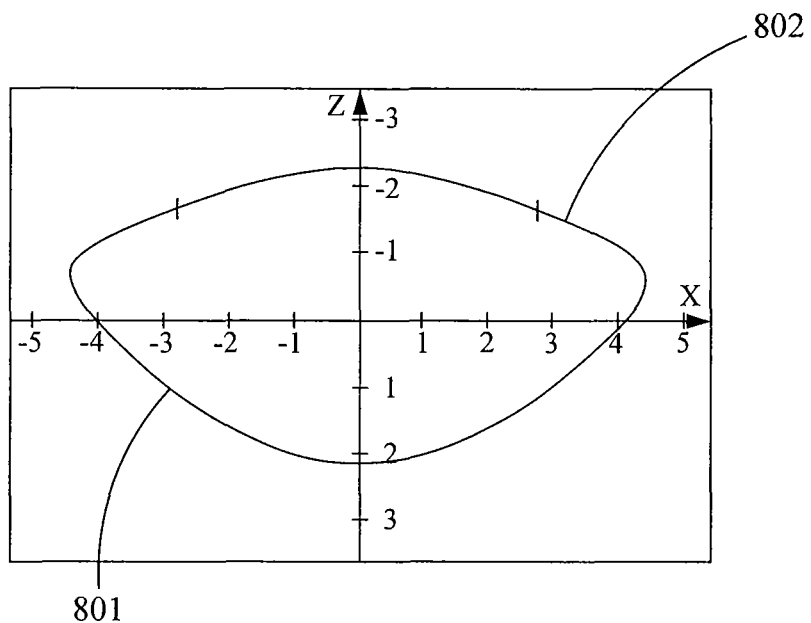
FIGS. 8 A-D are diagrams illustrating a band cut circular capsulotomy.
Figure 8B:
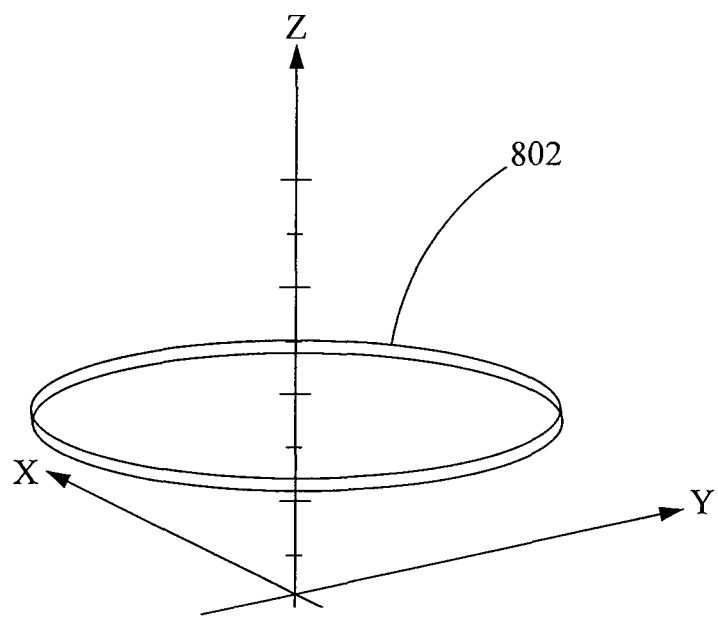
Figure 8C:
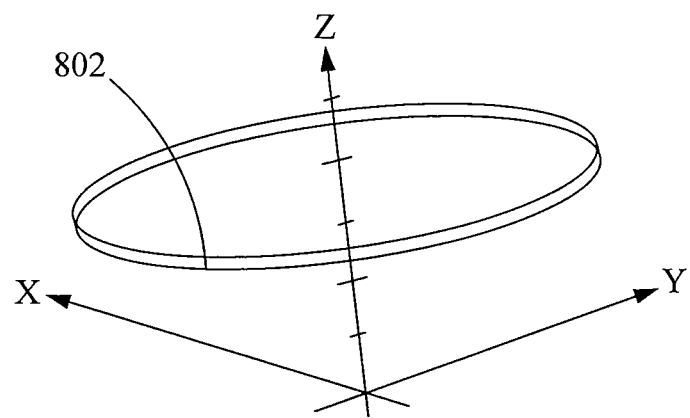
Figure 8D:
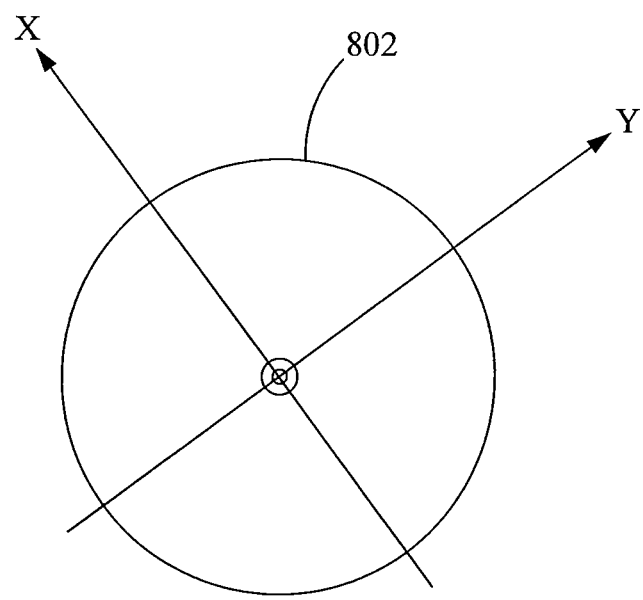

As illustrated in FIG. 7, there is provided a shot pattern to create 0.5 mm sized cubes out of the lens material. Thus, there is provided an outer lens surface 701, which is formed by the lens capsule and thus an outer shape of the lens. There is further provided a shot pattern 702 that creates grid like cuts, the end of which cuts 703 essentially follows the shape of the lens. There may be further provided one shell cut 704, which is integral with the grid like cuts. The sequence of laser shots in the pattern in FIG. 7 may be executed from posterior to anterior, as in most of the patterns disclosed herein, to obtain more predictable results by reducing the variation caused by shooting through gas bubbles. However, it may be desirable to shoot cataracts from the anterior to the posterior for the purpose of choosing the lesser of two undesirable effects. Thus, it may be advantageous to shoot through the gas bubbles, or let them dissipate, rather than shooting through cataractous tissue, which much more severely scatters the light and more quickly prevents photodisruption compared to gas bubble interference. Accordingly, it is proposed to photodisrupt the most anterior sections of the cataract first, then move posteriorly, shooting through gas bubble remnants of cataractous tissue, to the next layer of cataract tissue below. In addition to shooting the laser in anterior z planes then moving posterior, it is further provided to essentially drill down anterior to posterior, which we call the z axis throughout this document and then move in x/y and drill down again. The shot pattern of FIG. 7 may also be applied to a clear lens and that lens material is subsequently removed. It is desirable when dealing with a clear lens that shooting from posterior to anterior is utilized.

The creation of capsulotomy for the surgeon to access the lens to remove the lens material is illustrated in FIGS. 8 A-D. In these figures there is provided an outer surface 801, which surface is formed by the lens capsule, and thus an outer shape of the lens. There is further provided a ring shaped band cut 802 and shot pattern. This shot pattern is provided by placing the laser beam in a series of tightly placed shots around the ring at the deepest depth (most posterior ring) and then continuing that sequence as the depth of the ring is decreased. Thus, in general the shot will be distributed entirely around the ring at a particular depth before moving to a shallower depth. Thus, the figure shows the cross section view of cylindrical incision and accordingly provides for two sides 802 of the ring. The ring shaped capsulotomy cuts of 100 μm deep, approximately centered on the apex as determined by the above referenced method of the anterior lens capsule surface and precisely 5 mm in diameter. The diameter of the capsulotomy can be varied between about 0.1 mm to about 9 mm diameter.

Since the lens capsule is approximately 5 to 15 μm thick, it is desirable for the depth of the cut to be typically between 5 and several hundred um, although there is not much penalty for cutting several millimeters. With greater precision regarding the location and shape of the lens and lens apex the thickness of the band and in particular the amount of the band that is above the lens capsule and in the aqueous can be reduced. The shape of the capsulotomy can be elliptical with the x axis different then the y axis or other shapes. Thus, the shape of the capsulotomy can be any shape that provides a benefit for a particular IOL, for example the shape of the capsulotomy can be circular, elliptical, square, rectangular, or a non-geometric shape. The shape will be based at least in part upon and be determined at least in part by, the aspects of IOLs and in particular accommodating IOLs and IOLs that reduce and/or eliminate the need for spectacles. A particular IOL, such as FDA approved IOLs discussed herein, may benefit from and/or may require a particular capsulotomy shape and opening smoothness.

Figure 9A:
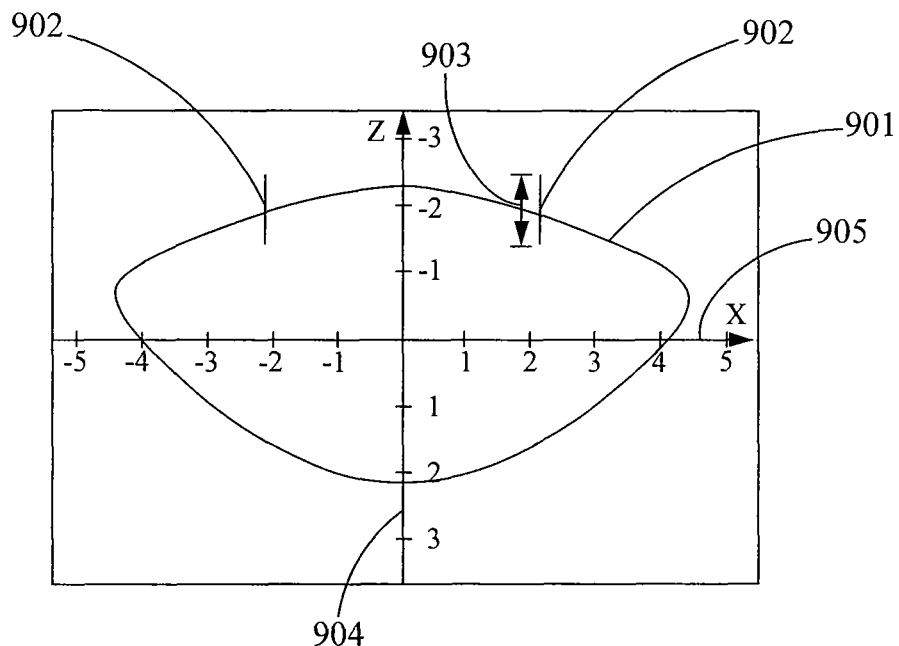
FIGS. 9 A-C are diagrams illustrating a jigsaw cut circular shaped capsulotomy.
Figure 9B:
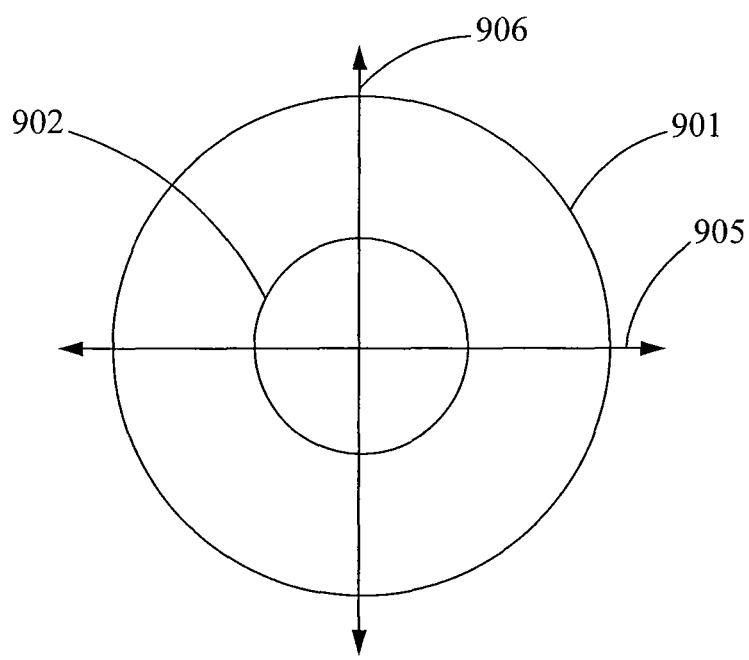
Figure 9C:
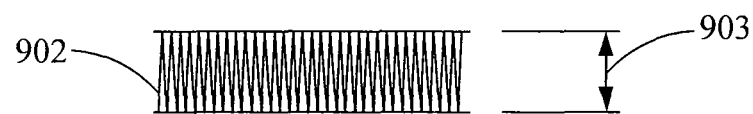

A jigsaw delivery sequence or pattern for performing a precision capsulotomy is further provided herein. As illustrated in FIGS. 9 A-C, there is provided an outer surface 901, which surface is formed by the lens capsule, and thus an outer shape of the lens. FIG. 9A is a cross section of the lens with an X axis 905 and a Z axis 904. FIG. 9B is a top view of the lens down the Z axis and has X axis 905 and Y axis 906. There is further provided a jigsaw cut 902 and shot pattern, in the shape of a circle on the plane of the X axis 905 and the Y axis 906, when viewed down the Z axis 904. The laser shot pattern is delivered in a series of tightly spaced vertical sweeps over the same X-Y point of the pattern. Thus, the Z position will change many times relative to the change in X-Y position as the shots are delivered. This rapidly changing Z position relative to the X-Y position is referred to as the vertical sweep of pattern 902 and the range of this sweep is shown by arrow 903. A particular IOL, such as FDA approved IOLs discussed herein, may benefit from and/or may require a particular capsulotomy shape and opening smoothness.

Figure 10A:
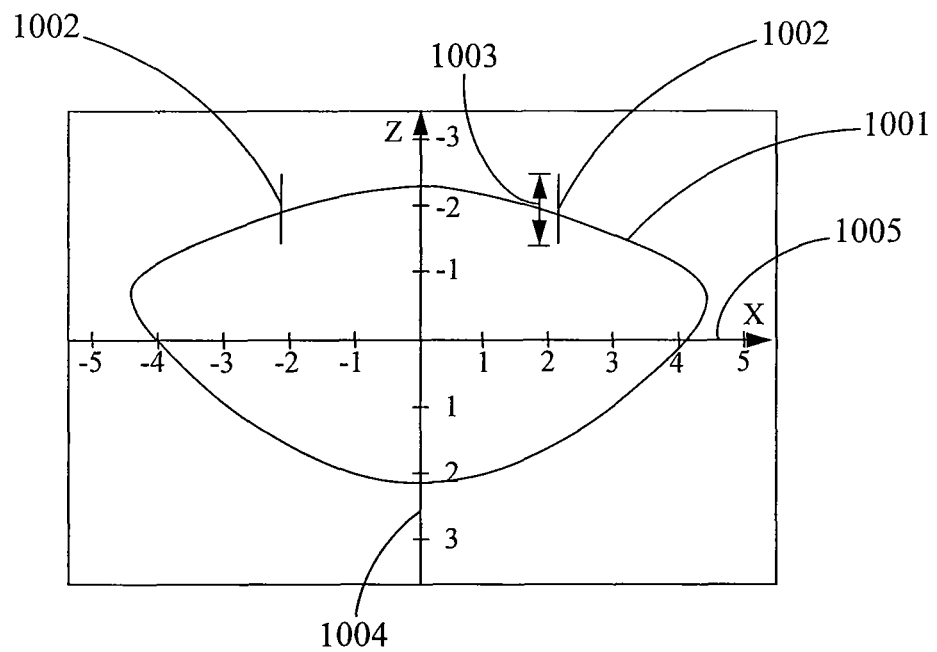
FIGS. 10 A-C are diagrams illustrating a jigsaw cut elliptical shaped capsulotomy.
Figure 10B:
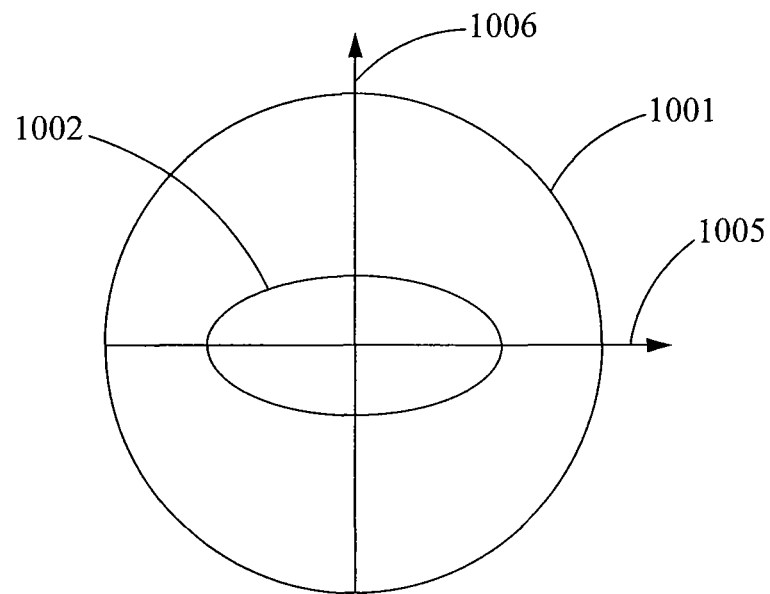
Figure 10C:
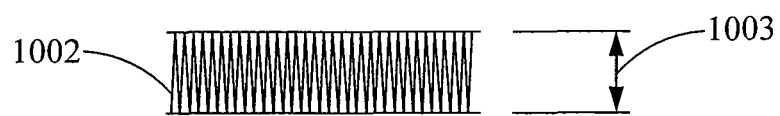

As illustrated in FIGS. 10 A-C, there is provided an outer surface 1001, which surface is formed by the lens capsule, and thus an outer shape of the lens. FIG. 10A is a cross section of the lens with an X axis 1005 and a Z axis 1004. FIG. 10B is a top view of the lens down the Z axis and has X axis 1005 and Y axis 1006. There is further provided a jigsaw cut 1002 and shot pattern, in the shape of an ellipse on the plane of the X axis 1005 and the Y axis 1006, when viewed down the Z axis 1004. The laser shot pattern is delivered in a series of tightly spaced vertical sweeps over the same X-Y point of the pattern. Thus the Z position will change many times relative to the change in X-Y position as the shots are delivered. This rapidly changing Z position relative to the X-Y position is referred to as the vertical sweep of pattern 1002 and the range of this sweep is shown by arrow 1003. A particular IOL, such as FDA approved IOLs discussed herein, may benefit from and/or may require a particular capsulotomy shape and opening smoothness.

Figure 11A:
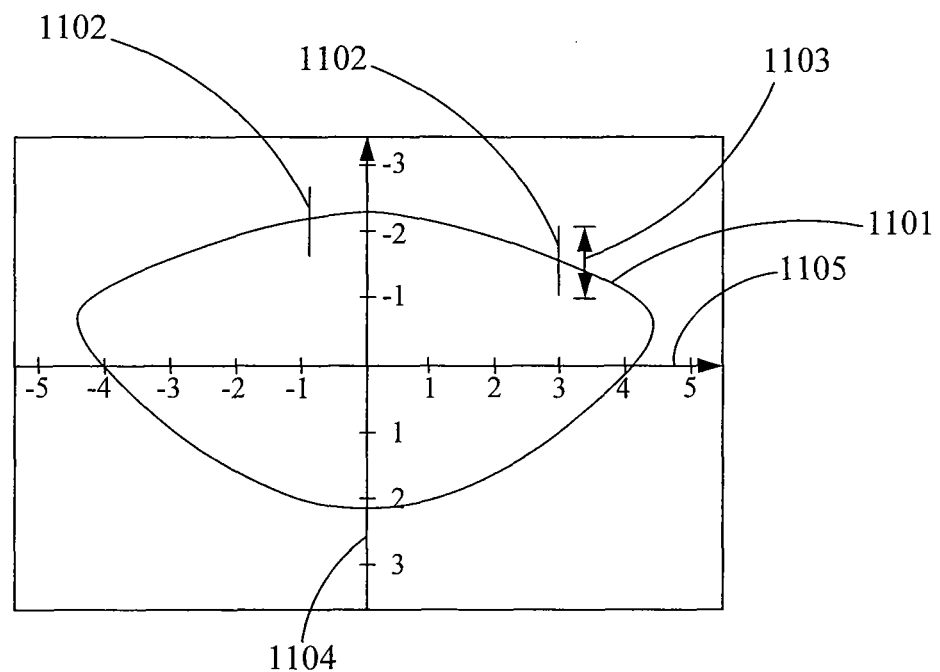
FIGS. 11A-C are diagrams illustrating a non-centered jigsaw cut circular shaped capsuolomy.
Figure 11B:
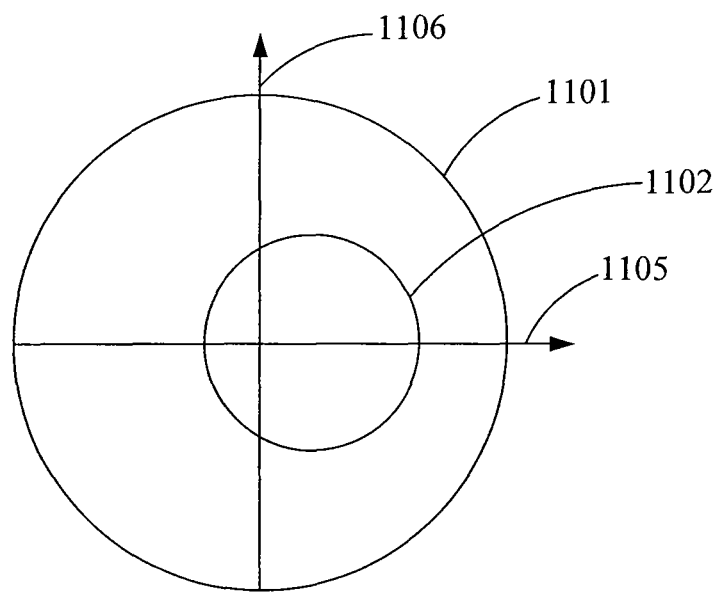
Figure 11C:
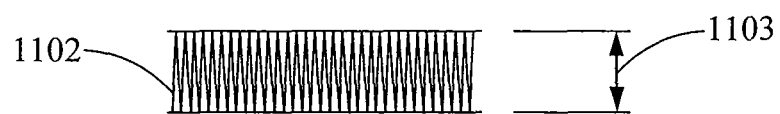

FIGS. 11A-C provide a circular shaped jigsaw cut of example 3 which has been placed off the center of the X-Y axis. Thus, there is provided an outer surface 1101, which surface is formed by the lens capsule, and thus an outer shape of the lens. There is provided an X axis 1105, a Y axis 1106 and a Z axis 1104. There is further provided a jigsaw cut 1102 and shot pattern, in the shape of a circle on the plane of the X axis 1105 and the Y axis 1106, when viewed down the Z axis 1104. The center of the circle of this shot pattern 1102 is not center upon the lens, i.e., the X-Y intersection, rather it is placed to right of center by about 1 mm.

Figure 12A:
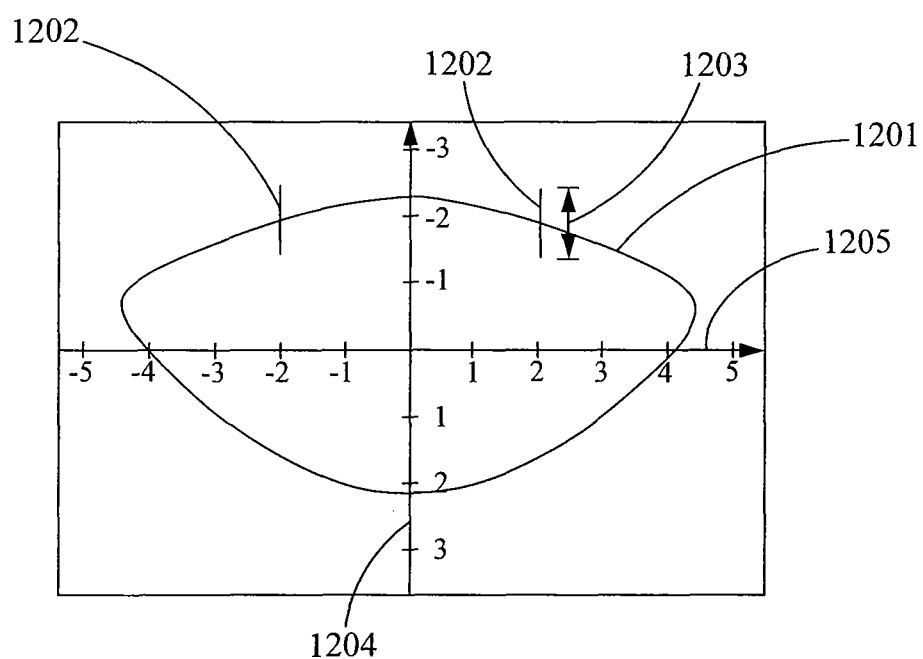
FIGS. 12 A-C are diagrams illustrating a shot pattern having cuts and lands.
Figure 12B:
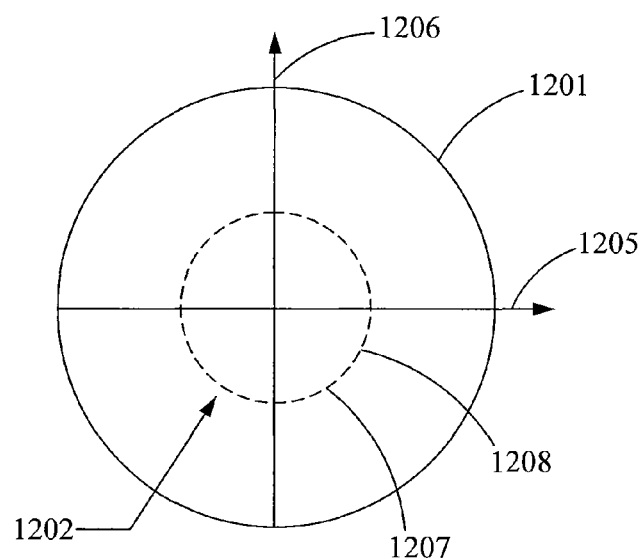
Figure 12C:
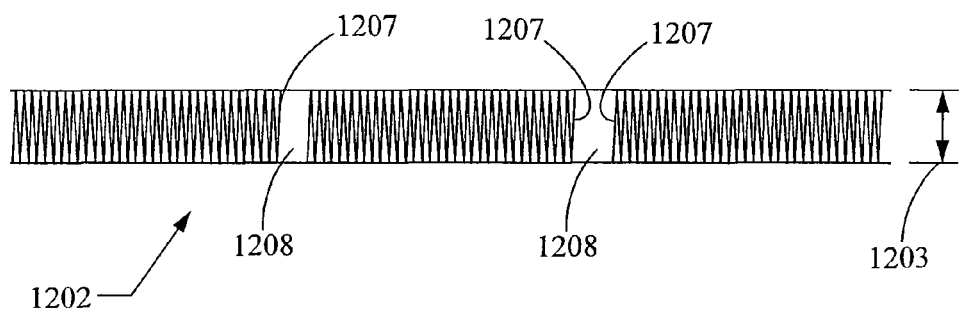

FIGS. 12A-C provide a circular cut and jigsaw cut. Thus, there is provided an outer surface 1201, which surface is formed by the lens capsule, and thus an outer shape of the lens. There is provided an X axis 1205, a Y axis 1206 and a Z axis 1204. There is further provided a jigsaw cut 1202 and shot pattern, in the shape of a circle on the plane of the X axis 1205 and the Y axis 1206, when viewed down the Z axis 1204. The shot pattern 1202 has cuts 1207, i.e., lens material and in particular lens capsule material are cut/removed, and lands 1208 where no material is removed.

The jigsaw type cuts set forth herein can further be accomplished by a fast small amplitude z scan, from the posterior position to an to anterior position, that is a scan having a z direction amplitude that is slightly larger than the thickness of the capsule and a high Pulse Rate Frequency (PRF), so that all the pulses of a "single z direction sweep" down the z-axis overlap in two dimensions when viewing the pattern along the anterior to posterior axis. A "single z direction sweep" is defined as a scan from the lowest (most posterior) point to the highest (most anterior) point along the jigsaw shot pattern, or alternatively, from the highest to the lowest point. Thus, to use a sine curve as a analogy, a "single z direction sweep" would be that portion of the curve from peak to trough or from trough to peak and "a full wave z direction sweeps" would be that continuous portion of the curve from peak to peak or from trough to trough. For purposes of illustration, the wavelength of the jigsaw cut is defined as the distance in the horizontal direction from one peak to the next.

Thus, for example, such overlap can be obtained by a shot pattern with a z direction amplitude of about 10-20 µm. More specifically, one example of such a shot pattern would have a z direction amplitude of +/−7.5 µm, a wavelength of 2.5 µm with three equally spaced pulses for each single z direction sweep of the jigsaw pattern. For a PRF of 100 kHz there are 10 µsec between shots, such a shot pattern would require 6000 full wave z direction sweeps to cut a single vertical ring of a capsulotomy of diameter 5 mm. The 36,000 total pulses for this full circular mini-jigsaw pattern would require 0.36 second to complete.

A complete capsulotomy would comprise a stacked series of circular mini-jigsaw patterns of the same diameter, with each mini-jigsaw pattern having a vertical extent of 15 µm and with overlapping in the z direction with the adjacent mini-jigsaw patterns to ensure a complete cut at each z level. The mini-jigsaw patterns would be cut starting with the most posterior mini-jigsaw pattern; when that pattern was cut, the next most anterior pattern would be added until the height of the stacked mini-jigsaw patterns was sufficient to cut from below (posterior to) the anterior lens capsule position, through the capsule and into the anterior chamber. The composite form of the stacked patterns is in the shape of an annulus. The height of the annulus needed to ensure a z extent large enough to guarantee that the annulus cuts through the anterior lens capsule depends on the thickness of the capsule, but also the accuracy and precision of the positioning of laser pulses. Such accuracy and precision can be characterized by a standard deviation which includes variations, from all sources, in the actual versus desired z position of laser shots.

Using this pattern and rate the first pattern (mini-jigsaw pattern) could be delivered at the most posterior position for 3 to 5 sigma accuracy. Thus, for a nominal 50 µm z standard deviation (sigma) the first pattern would start at about 150 to 250 µm below the nominal estimated position of the capsule and then after each pattern is completed the next pattern would be moved anteriorly by an amount that is smaller than the extent, thus for example the pattern can move anteriorly by 10 µm (e.g., 33% or 5 µm out of the 15 µm nominal extent) for each subsequent pattern after the first until the capsulotomy is completed. Thus, for example a capsulotomy using this mini-jigsaw technique can be completed in about 11 seconds—nominal 3 sigma treatment, +/−150 µm total pattern, 30 mini-jigsaw cuts; 29 anterior 10 µm moves; 0.36 sec/mini-jigsaw pattern.

A variation of and optimization of the jigsaw type patterns and cuts is provided. Thus, the treatment laser is used as position determining laser, i.e., as laser radar (LADAR), as well as, for performing the capsulotomy.

Figure 14:
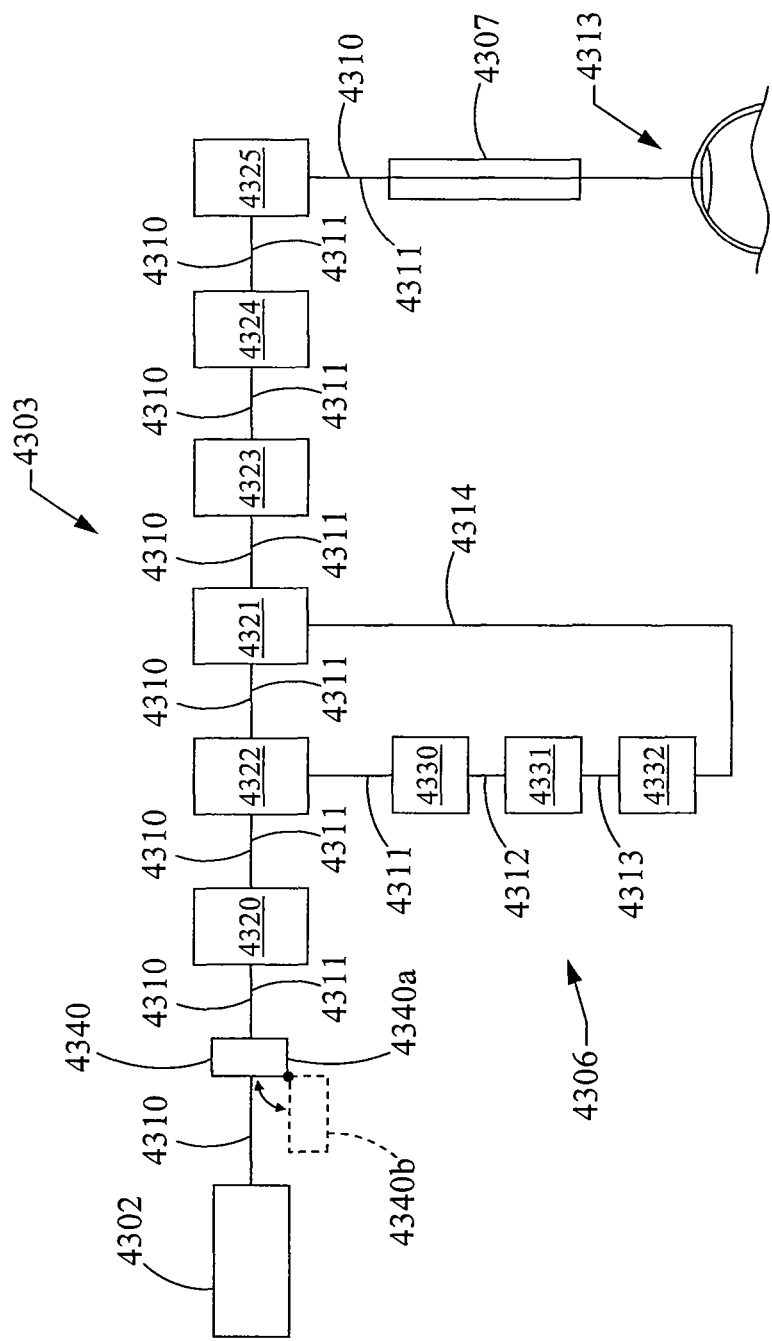
FIG. 14 is a schematic block diagram of a laser delivery and finder system.

An illustrative system utilizing by way of example specific optics for delivering the laser beam and a means for determining the position of the lens, and in particular the anterior and posterior capsule of the lens, is shown in FIG. 14. Thus, the example of FIG. 14 provides a laser 4302, laser optics 4303, which optics includes a beam expander telescope 4320, a polarizing beam splitter 4322, a z focus module or mechanism 4321, a polarizer ¼ wave plate 4323, an x-y scanner 4324, and imaging or focusing optics 4325. Thus, as set forth in FIG. 14, the laser beam path 4310, in part, passes from beam expander telescope 4320 to polarizing beam splitter 4322 to z focus module or mechanism 4321 to polarizer ¼ wave plate 4323, to x-y scanner 4324, and then to imaging or focusing optics 4325. There is further provided range detector components 4306, including an optical detector 4330, which receives return laser beam along path 4311 and produces analog input signal 4312, analog electronics 4331, which receives analog input signal 4312 and produces analog output signal 4313, and digital electronics and control 4332, which receives analog output signal 4313 and produces control signal 4314, which control signal is received by z focus module or mechanism 4321. There is also provided a laser beam path 4311 for the range detector. An attenuator 4340 is provided and can be moved between two positions 4340*a*, in which the laser is attenuated and 4340*b* in which the laser is not attenuated. A laser patient interface 4307 is provided.

FIG. 14 is a block schematic diagram and thus the relative positions and spacing of the components illustrated therein are by way of example. Accordingly, the relative placements of these components with respect to one another may be varied, and all or some of their functions and components may be combined.

This approach utilizes an attenuated version of the treatment laser to be used as a transmitter/illuminator. There is provided an optical receiver which is polarization duplexed 4322 together into a single transceiver path 4311/4310, which utilizes the same optical path to the eye as the treatment laser. In this way, the transceiver path looks through the Z focus mechanism 4321 and the imaging optic 4325 that provide a small spot size for photodisruption, but will not photodisrupt because of the attenuator. The transceiver beam is therefore scanable throughout the full lens volume.

Figure 15:
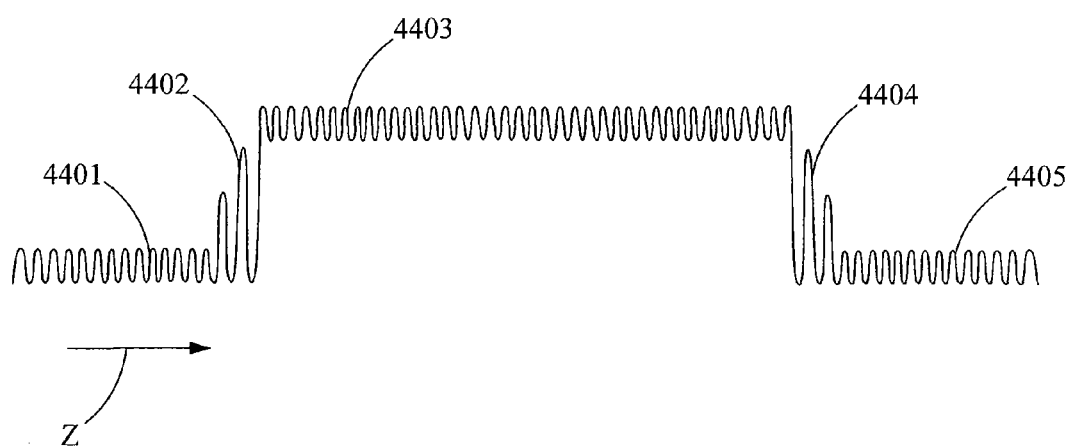
FIG. 15 is an illustration of a return signal for the system of FIG. 14.

With the attenuator in place 4340*a*, an AC periodic dither is applied to Z amplitude vs time. The focus point, keeping the x and y coordinates the same, is then moved from above the anterior surface of the lens, through the lens to the posterior surface and then slightly beyond. In this way for any x-y coordinate there will be a noticeable change in the amplitude of the laser beam that is returned, which change will be detected by the optical detector 4330. Thus, there will be provided an analog input signal 4312, an analog output signal 4313 and a control signal 4314. This change will correspond to the lens outer surfaces. An example of this change is provided in FIG. 15, in which 4401 represents the returned signal when the focus is above the anterior surface of the lens, 4402 represents the signal as the focus moves through the anterior lens capsule, 4403 represents the signal as the focus is in the lens, 4404 represents the signal as the focus moves through the posterior lens capsule, and 4405 represents the signal as the focus is beyond (posterior to) the lens. Further, as described in greater detail in the following paragraphs, a servo can be utilized to lock the z direction focus for any x y coordinate of the lens at predetermined offset to prevent the treatment laser from disrupting material at or near the lens capsule.

The dither could be a ramp or saw tooth or a simple sine wave of Z amplitude vs time dither, approximately 10's to 100's of μm in amplitude, to the Z focus assembly. To initially find the position of the anterior capsule, an offset is applied to the Z focus module with the focus starting just posterior to the cornea and then proceeding posteriorly to the anterior capsule in Z (typically mm's) until the transceiver 4330 receives an increasingly strong periodic signal return 4402 from the anterior capsule. The change in index between the aqueous humor and the lens capsule as well as scattering from the capsule or fibrous tissue, compared to the uniform aqueous provides the optical return signal, which is sensed by the optical receiver. The periodic signal detected in the receiver will increase as the dithered and focused transceiver is Z offset downward and approaches the edge of the capsule. As the Z focus is pushed into the fibrous mass, the dithered signal will reach a maximum and then begin to decrease. The direction of the Z focus offset and leading edge of the signal "S-Curve" are used to form a discriminator function, which can provide a directionally dependent error signal, to drive the Z-Focus offset, to maximize the dithered signal return at the edge of the capsule, through closed loop servo techniques. Once the Z Offset loop, which is essentially a range servo, is closed, then the transceiver focus will track, in Z-offset, any location on the anterior capsule. After the Z-offset loop is closed and tracking, X and Y scanning can now be accomplished and the recording of the tracked Z-offset position for every x,y location will essentially create a 3D map of the anterior surface. An X-Y scan pattern, slow enough to not break lock on the Z-Offset tracker could scan in a spiral or other pattern from the anterior pole outward to approximately just less than the pupil diameter to create a 3 D map of reasonably uniform sampling over the pupil limited lens diameter. Once this anterior data is captured, the X-Y could return to 0,0 and then the loop opened and the Z offset commanded further down toward the posterior pole and again a signal increase will occur at the interface between the posterior capsule and the vitreous humor, albeit a sign change may occur. Likewise the Z-offset loop can now lock onto and track the posterior capsule and a similar x-y scan can be used to map out the posterior lens shape.

The significant advantages of this technique is that the unknown gradient refractive index of the lens and as well as the refractive index of the cornea do not contribute uncertainly to this measurement, as we are not recording the absolute, laboratory fixed, Cartesian X-Y-Z position and shape of the lens surfaces, but instead the Z offset command necessary at each X-Y position to position the beam at the anterior capsule. Since the treatment beam is at the same wavelength as the attenuated probe beam used to find the position of the lens capsule, the mapping of z offset to the beam focus required to focus the attenuated beam at the lens capsule, as a function of x,y position also provides the z offset necessary for the treatment beam to cut at the lens capsule as a function of the x, y position, independent of the refractive index of the cornea and lens and any inhomogeneities therein. This means the shape of the lens is being defined in the exact same coordinate system as used by the treatment laser with no systematic error; the attenuated laser is being used as the transmitter, with the same Z-focus assembly and the same imaging optics as the treatment beam.

Figure 16:
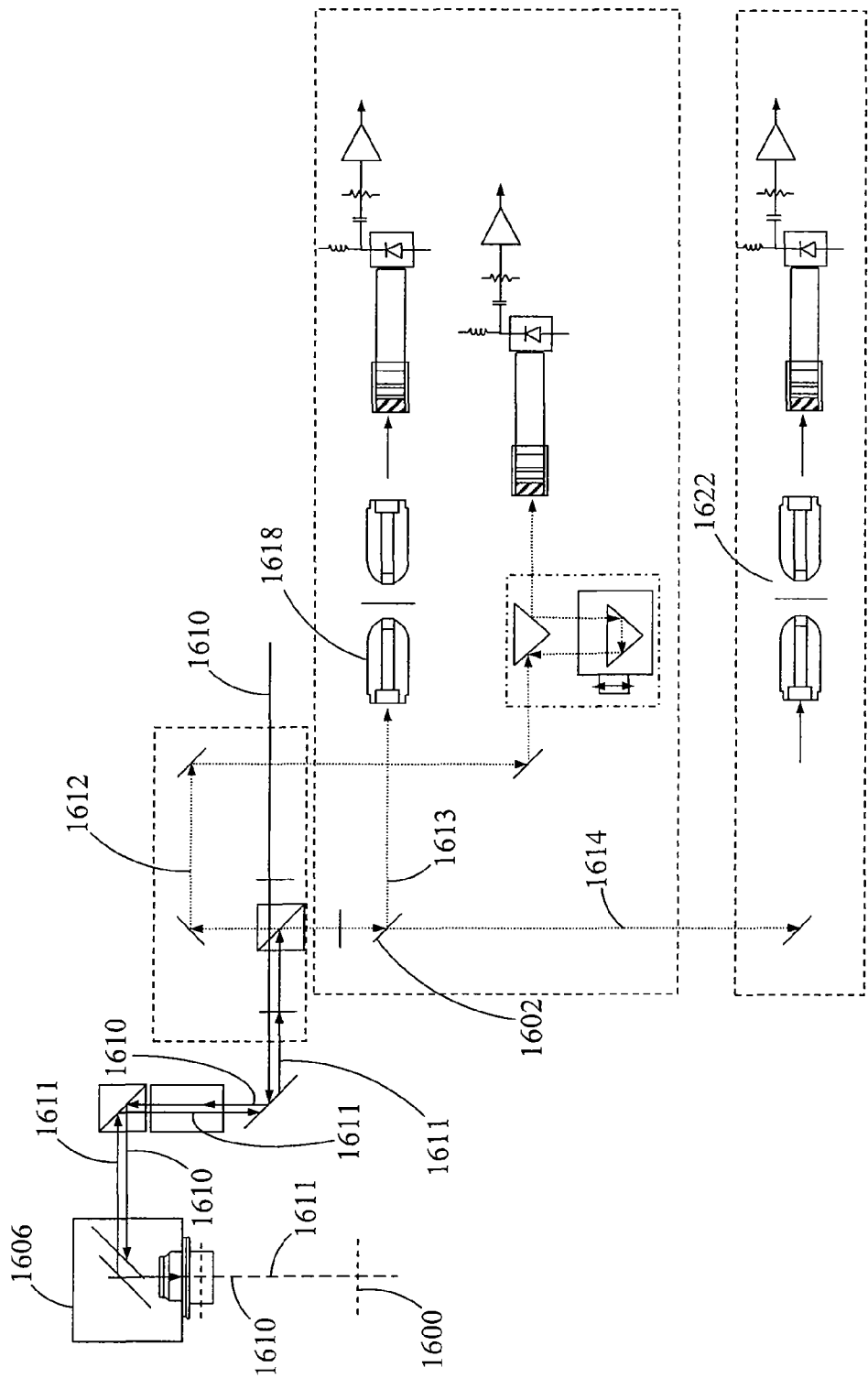
FIG. 16 is an illustration of an EO Modular.

In a more preferred configuration an EO modulator is used as an alternative to the attenuator. Thus as illustrated by way of example in FIG. 16 system that is has targeting plan 1600 that would correspond to, or be positioned on or within the natural crystalline lens of the patent. There is a laser beam path 1610 from the laser (not shown) to the target plane 1600. There is provided a second laser beam path 1611 in which reflected laser light is transmitted back from the eye. This return path is then divided by beam splitter means 1601 and 1602 into three laser beam return paths 1612, 1613, and 1614. The first return beam path 1612 provides a reference signal, or channel. This beam path is travels through the illustrated components and the resultant signal is then sent to a master computer for processing.

The second return beam path 1613 provides a signal, or channel, for a near spatial filter assembly 1618. This beam path travels through the illustrated components and the resultant signal is then sent to a master computer for processing.

The third return beam path 1614, provides a signal, or channel, for a far spatial filter assembly 1622. The beam path travels through the illustrated components and the resultant signal is then sent to a master computer for processing.

There is further provided a scanner 1606 and the illustrated components.

In this way the use of the far and near spatial filters 1622 and 1618 provides for a gating effect that eliminates a large amount of the stray backscatter light and only lets the scattered or reflected light from the focus of the scanned transceiver beam through for processing. This provides a heightened sensitivity in the z direction and results in enhanced ability to determine the position of the lens capsule.

Figure 13:
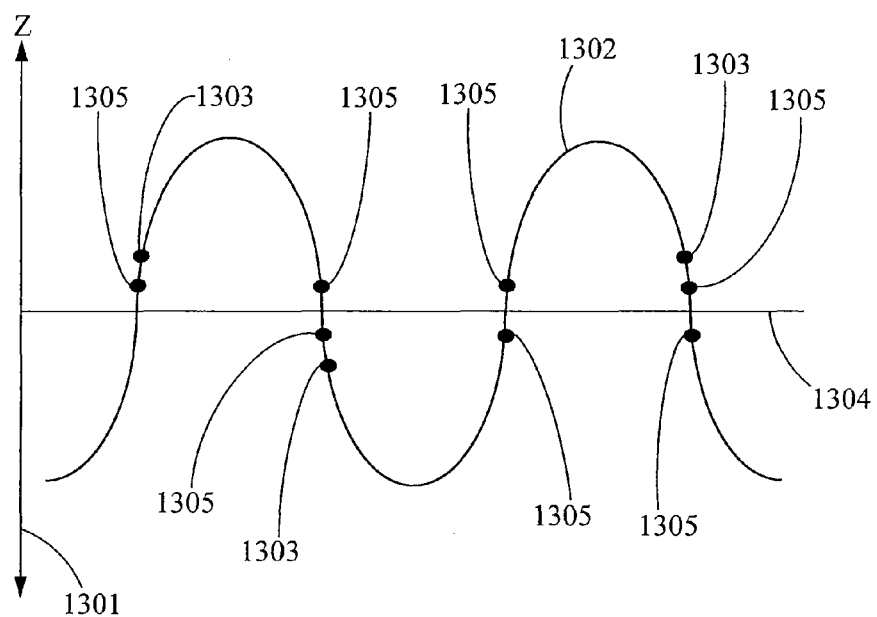
FIG. 13 is a diagram illustrating a pattern of tracking and cutting with the therapeutic laser.

As shown in FIG. 13 there is provided an illustration of a laser pattern having a changing z focus. For purposes of illustration in this figure movement is shown in only the x and z directions for simplification, it being readily understood that movement in both the x and y direction would take place, would be preferable, and would be needed to perform a capsulotomy and in particular any of the capsulotomies provided herein. Thus, there is shown a z axis 1301 (which coincides with the anterior-posterior A/P axis of the lens), a laser shot pattern 1302, specific sets of shots 1303 and 1305 that achieve Laser Induced Optical Breakdown (LIOB), in the area of the anterior surface of the lens 1304, which the remaining shots in pattern 1302 are below LIOB threshold. The set of laser shots 1305 are within 10-15 μm of the anterior surface of the capsule. Preferably the majority of the shots exceeding LIOB in the pattern should be in this area of the pattern, i.e., the majority of the shots that exceed LIOB should be in the range of from −5 to 15 μm of the anterior surface of the capsule. More preferably the majority of the shots exceeding LIOB should be in range of from about 0 to about 15 μm above the surface of the capsule and even more preferably the range should be from about 0 to about 10 μm. It is theorized, and applications provide this theory to further the teaching of the art but are in no way bound by this theory, that the reaction of the laser shot in the area slightly above the capsule creates in function a touch like effect where by way of analogy, the cutting flame of the touch, would extend away from the shot location in a posterior direction along the general path of the laser beam delivering the shot.

The treatment laser is used as a source for laser radar that measures and tracks the position of the anterior lens capsule using a range servo system, as described above by way of example. Initially laser energy/power below LIOB threshold is utilized to determine the position of the anterior capsule of the lens. This is achieved by scanning the laser in an x, y pattern, such as an ellipse, a circle or any other predetermined shape for a capsulotomy, and varying the z focus. In this way the position of the anterior surface of the lens along the location for the capsulotomy can be determined. As the location is determined, this scanning can be continued with the energy/power of the laser being increased to LIOB for those shots that are in very close proximity to the anterior surface of the lens. In this manner tracking, location determination and cutting can be simultaneously accomplished. This provides the added benefit of reduced bubble formation because essentially only the shots needed to accomplish the capsulotomy are above LIOB threshold and thus bubble formation is reduced and minimized.

Thus, it is preferred to use a z dithered ranger loop to locate the lens surface. In such a loop, the laser beam is oscillated in the z direction (along the lens anterior-posterior axis) to allow a tracker loop to detect the return signal from the anterior capsule by the use of an optical receiver path that contains a small F# spatial filter so that the return signal is sensitive to the z position of the system and therefore a hill-climbing servo, a well known servo control algorithm, can be used to track the anterior surface of the capsule. When the z dithered ranger loop is closed and stable during a predetermined scan the laser energy is raised to above LIOB threshold and the cutting action will take place. Thus, there is provided a jigsaw type cut of the types disclosed herein, with reduced bubble formation.

The combination of the patterns and types of cuts provided herein can be interchanged and other shapes of patterns and positions relative to the X-Y center of the lens may be employed. Moreover, because there is a greater likelihood for a missed laser shot with the band cut, i.e., the ring delivery sequence or pattern, such as shown in FIGS. 8A-D, than the jigsaw sequence, the use of the technique to determine the location, apex and shape of the lens is important, but not as critical, as when the ring sequence is being employed.

From the foregoing description, one skilled in the art can readily ascertain the essential characteristics of this invention, and without departing from the spirit and scope thereof, can make various changes and/or modifications of the invention to adapt it to various usages and conditions. Accordingly, the present invention may be embodied in other forms than those specifically disclosed herein without departing from its spirit or essential characteristics. The described embodiments are to be considered in all respects only as illustrative and not restrictive, and the scope of the invention is commensurate with the appended claims rather than the foregoing description.

What is claimed:

1. A system for reducing eye-to-eye and surgeon-to-surgeon variability in performing procedures to create cuts in a capsule of a lens of an eye, the system comprising:
 a laser for producing a laser beam;
 an optical path for directing the laser beam from the laser to a lens of an eye; and
 a control system for at least directing the laser beam in a predetermined jigsaw capsulotomy pattern comprising a plurality of laser shots positioned in x, y and z directions as they are directed toward the lens of the eye, wherein the predetermined jigsaw capsulotomy pattern is formed by directing the plurality of shots along a planar pattern contained in an x-y plane, and performing, for each x-y position of the planar pattern, a series of tightly spaced full wave sweeps in the z-direction.

2. The system of claim 1 wherein: the predetermined jigsaw capsulotomy pattern comprises a first essentially straight section, a second essentially straight section, a first curved section and a second curved section; and the first essentially straight section is connected to the first and second curved sections.

3. The system of claim 1 wherein a shape of the predetermined jigsaw capsulotomy pattern is based at least in part on a shape of an IOL, the IOL comprising a hinge, and the predetermined jigsaw capsulotomy pattern essentially following the shape of the IOL.

4. The system of claim 1 wherein the laser beam comprises a first power below LIOB and a second power at or above LIOB.

5. The system of claim 4 wherein the first power is used as laser radar to determine a position of an anterior lens capsule of the lens of the eye and the second power is used to cut the anterior lens capsule of the lens of the eye, whereby the second power performs capsulotomy.

6. The system of claim 5 wherein the plurality of laser shots are alternated between a series of shots at the first power and a series of shots at the second power along the predetermined jigsaw capsulotomy pattern.

7. The system of claim 6 wherein a majority of the series of shots at the second power are placed substantially in an area of an anterior portion of the anterior lens capsule.

8. A system for reducing eye-to-eye and surgeon-to-surgeon variability in performing procedures to create cuts in a capsule of a lens of an eye, the system comprising:
 a laser for producing a laser beam;
 an optical path for directing the laser beam from the laser to a lens of an eye;
 the laser beam having a first power below LIOB and a second power above LIOB;
 a control system for at least directing the laser beam in a predetermined shaped shot pattern on a portion of an anterior capsule of the lens of the eye to create a precise predetermined non-geometric shaped capsulotomy; and
 a shape of the predetermined shaped shot pattern being based at least in part on a shape of an IOL.

9. The system of claim 8 wherein the predetermined shaped shot pattern comprises at least one essentially straight section.

10. The system of claim 8 wherein the predetermined shaped shot pattern comprises at least two essentially straight sections.

11. The system of claim 8 wherein the predetermined shaped shot pattern comprises a first essentially straight section, a second essentially straight section, a first curved section and a second curved section.

12. The system of claim 8 wherein: the predetermined shaped shot pattern comprises a first essentially straight section, a second essentially straight section, a first curved section and a second curved section; and, the first essentially straight section is connected to the first and second curved sections.

13. The system of claim 8 wherein the predetermined shaped shot pattern is a jigsaw pattern.

14. The system of claim 8 wherein the IOL is an FDA approved accommodating IOL.

15. The system of claim 8 wherein the IOL is an FDA approved IOL for near, intermediate and distance vision.

16. The system of claim 8 wherein the IOL is an FDA approved IOL that reduces or eliminates a need for spectacles.

17. The system of claim 8, wherein the first power is used as laser radar to determine a position of the anterior lens capsule of the lens of the eye and the second power is used to cut the anterior lens capsule of the lens of the eye to create the precise predetermined non-geometric shaped capsulotomy.

18. The system of claim 17, wherein a plurality of laser shots from the laser are alternated between a series of shots at the first power and a series of shots at the second power along a pattern to create the precise predetermined non-geometric shaped capsulotomy.

19. The system of claim 18, wherein a majority of the series of shots at the second power are placed substantially in an area of an anterior portion of the anterior lens capsule.

20. A system for reducing eye-to-eye and surgeon-to-surgeon variability in performing procedures to create cuts in a capsule of a lens of an eye, the system comprising:
a therapeutic laser for producing a therapeutic laser beam;
an optical path for directing the therapeutic laser beam from the therapeutic laser to a lens of an eye;
a control system for at least directing the laser beam in a predetermined jigsaw capsulotomy pattern comprising a plurality of laser shots positioned in x, y and z directions as they are directed toward the lens of the eye, wherein the predetermined jigsaw capsulotomy pattern is formed by directing the plurality of shots along a planar pattern contained in an x-y plane, and performing, for each x-y position of the planar pattern, a series of tightly spaced full wave sweeps in the z-direction;
a first pattern positioned in a first area of an anterior capsule of the lens of the eye, the first pattern having a z direction sweep range less than about 15 µm;
a second pattern positioned in a second area of the anterior capsule of the lens of the eye, the second area is anterior to the first area, the second pattern having a z direction sweep range of less than about 15 µm.

21. The system of claim 20 wherein a shape of the predetermined jigsaw capsulotomy pattern is based at least in part on a shape of an IOL, the IOL having at least one hinge, and, the predetermined jigsaw capsulotomy pattern essentially follows the shape of the IOL.

22. The system of claim 20 wherein the z direction sweep ranges of both the first pattern and the second pattern are less than about 10 µm.

23. The system of claim 20 where in the z direction sweep ranges of both the first pattern and the second pattern are less than about 5 µm.

24. A system for reducing eye-to-eye and surgeon-to-surgeon variability in performing procedures to create cuts in a capsule of a lens of an eye, the system comprising:
a laser for producing a laser beam;
an optical path for directing the laser beam from the laser to a targeting plane positioned within a lens of an eye;
a first return beam path that receives a first portion of light transmitted from the eye and directs the first portion of light to a near spatial filter assembly which generates a first signal;
a second return beam path that receives a second portion of light transmitted from the eye and directs the second portion of light to a far spatial filter assembly which generates a second signal; and
a computer that receives and processes the first signal and the second signal so that a large amount of backscatter light is eliminated.

25. The system of claim 24, further comprising a third return beam path that receives a third portion of light transmitted from the eye which is generated into a third signal that is received by the computer and processed by the computer to generate a reference signal.

* * * * *